US008821486B2

(12) United States Patent
Toth et al.

(10) Patent No.: US 8,821,486 B2
(45) Date of Patent: Sep. 2, 2014

(54) TISSUE ABLATION SYSTEMS AND METHODS

(75) Inventors: Akos Toth, Cupertino, CA (US); Csaba Truckai, Saratoga, CA (US)

(73) Assignee: Hermes Innovations, LLC, Cupertino, CA (US)

( * ) Notice: Subject to any disclaimer, the term of this patent is extended or adjusted under 35 U.S.C. 154(b) by 965 days.

(21) Appl. No.: 12/944,466

(22) Filed: Nov. 11, 2010

(65) Prior Publication Data

US 2011/0282340 A1 Nov. 17, 2011

Related U.S. Application Data

(60) Provisional application No. 61/307,362, filed on Feb. 23, 2010, provisional application No. 61/261,246, filed on Nov. 13, 2009.

(51) Int. Cl.

| A61B 18/18 | (2006.01) |
|---|---|
| A61B 18/04 | (2006.01) |
| A61B 18/00 | (2006.01) |
| A61B 19/00 | (2006.01) |
| A61B 18/14 | (2006.01) |

(52) U.S. Cl.
CPC ..... *A61B 18/042* (2013.01); *A61B 2018/00214* (2013.01); *A61B 2018/00821* (2013.01); *A61B 2018/00083* (2013.01); *A61B 2019/302* (2013.01); *A61B 2018/00797* (2013.01); *A61B 2018/00898* (2013.01); *A61B 2018/143* (2013.01); *A61B 2018/00648* (2013.01); *A61B 2018/00702* (2013.01); *A61B 2018/00744* (2013.01); *A61B 18/1492* (2013.01); *A61B 2018/00136* (2013.01); *A61B 2018/147* (2013.01); *A61B 18/1442* (2013.01); *A61B 2018/1427* (2013.01)

USPC .............................................. 606/33; 606/41

(58) Field of Classification Search
USPC ...................................................... 606/32–41
See application file for complete search history.

(56) References Cited

U.S. PATENT DOCUMENTS

| 3,903,891 A | 9/1975 | Brayshaw |
|---|---|---|
| 4,949,718 A | 8/1990 | Neuwirth et al. |
| 4,979,948 A | 12/1990 | Geddes et al. |
| 5,045,056 A | 9/1991 | Behl |
| 5,078,717 A | 1/1992 | Parins |
| 5,084,044 A | 1/1992 | Quint |
| 5,191,883 A | 3/1993 | Lennox et al. |

(Continued)

FOREIGN PATENT DOCUMENTS

| EP | 1236440 A1 | 9/2002 |
|---|---|---|
| EP | 1595507 A2 | 11/2005 |

(Continued)

OTHER PUBLICATIONS

Office action dated Mar. 12, 2012 for U.S. Appl. No. 12/541,043.

(Continued)

*Primary Examiner* — Linda Dvorak
*Assistant Examiner* — Amanda Scott
(74) *Attorney, Agent, or Firm* — Wilson Sonsini Goodrich & Rosati

(57) ABSTRACT

Tissue is treated using a radiofrequency power supply connected to an applicator having a chamber filled with an electrically non-conductive gas surrounded by a thin dielectric wall. A radiofrequency voltage is applied at a level sufficient to ionize the gas into a plasma and to capacitively couple the ionized plasma with the tissue to deliver radiofrequency current to ablate or otherwise treat the tissue.

26 Claims, 53 Drawing Sheets

(56) References Cited

U.S. PATENT DOCUMENTS

| | | |
|---|---|---|
| 5,242,390 A | 9/1993 | Goldrath |
| 5,248,312 A | 9/1993 | Langberg |
| 5,277,201 A | 1/1994 | Stern |
| 5,344,435 A | 9/1994 | Turner et al. |
| 5,374,261 A | 12/1994 | Yoon |
| 5,401,272 A | 3/1995 | Perkins |
| 5,441,498 A | 8/1995 | Perkins |
| 5,443,470 A | 8/1995 | Stern et al. |
| 5,501,681 A | 3/1996 | Neuwirth et al. |
| 5,505,730 A | 4/1996 | Edwards |
| 5,558,672 A | 9/1996 | Edwards |
| 5,562,703 A | 10/1996 | Desai |
| 5,562,720 A | 10/1996 | Stern et al. |
| 5,575,788 A | 11/1996 | Baker et al. |
| 5,584,872 A | 12/1996 | LaFontaine et al. |
| 5,653,692 A | 8/1997 | Masterson et al. |
| 5,681,308 A | 10/1997 | Edwards et al. |
| 5,697,281 A | 12/1997 | Eggers |
| 5,697,882 A | 12/1997 | Eggers |
| 5,713,942 A | 2/1998 | Stern et al. |
| 5,769,846 A | 6/1998 | Edwards et al. |
| 5,769,880 A | 6/1998 | Truckai et al. |
| 5,800,493 A | 9/1998 | Stevens et al. |
| 5,827,273 A | 10/1998 | Edwards |
| 5,843,020 A | 12/1998 | Tu et al. |
| 5,846,239 A | 12/1998 | Swanson et al. |
| 5,860,974 A | 1/1999 | Abele |
| 5,876,340 A | 3/1999 | Tu et al. |
| 5,891,094 A | 4/1999 | Masterson et al. |
| 5,891,134 A | 4/1999 | Goble et al. |
| 5,891,136 A | 4/1999 | McGee |
| 5,902,251 A | 5/1999 | vanHooydonk |
| 5,904,651 A | 5/1999 | Swanson et al. |
| 5,925,038 A | 7/1999 | Panescu et al. |
| 5,954,714 A | 9/1999 | Saadat et al. |
| 5,964,755 A | 10/1999 | Edwards |
| 5,976,129 A | 11/1999 | Desai |
| 5,997,534 A | 12/1999 | Tu et al. |
| 6,024,743 A | 2/2000 | Edwards |
| 6,026,331 A | 2/2000 | Feldberg et al. |
| 6,041,260 A | 3/2000 | Stern et al. |
| 6,053,909 A | 4/2000 | Shadduck |
| 6,057,689 A | 5/2000 | Saadat |
| 6,086,581 A | 7/2000 | Reynolds et al. |
| 6,113,597 A | 9/2000 | Eggers |
| 6,139,570 A | 10/2000 | Saadat et al. |
| 6,146,378 A | 11/2000 | Mikus et al. |
| 6,149,620 A | 11/2000 | Baker et al. |
| 6,228,078 B1 | 5/2001 | Eggers et al. |
| 6,254,599 B1 | 7/2001 | Lesh et al. |
| 6,283,962 B1 | 9/2001 | Tu et al. |
| 6,296,639 B1 | 10/2001 | Truckai et al. |
| 6,302,904 B1 | 10/2001 | Wallsten et al. |
| 6,315,776 B1 | 11/2001 | Edwards et al. |
| 6,366,818 B1 | 4/2002 | Bolmsjo |
| 6,387,088 B1 | 5/2002 | Shattuck et al. |
| 6,395,012 B1 | 5/2002 | Yoon et al. |
| 6,416,508 B1 | 7/2002 | Eggers et al. |
| 6,416,511 B1 | 7/2002 | Lesh et al. |
| 6,443,947 B1 | 9/2002 | Marko et al. |
| 6,508,815 B1 | 1/2003 | Strul et al. |
| 6,551,310 B1 | 4/2003 | Ganz et al. |
| 6,589,237 B2 | 7/2003 | Woloszko et al. |
| 6,602,248 B1 | 8/2003 | Sharps et al. |
| 6,607,545 B2 | 8/2003 | Kammerer et al. |
| 6,635,054 B2 | 10/2003 | Fjield et al. |
| 6,635,055 B1 | 10/2003 | Cronin |
| 6,663,626 B2 | 12/2003 | Truckai et al. |
| 6,673,071 B2 | 1/2004 | Van Dusseldorp et al. |
| 6,699,241 B2 | 3/2004 | Rappaport et al. |
| 6,726,684 B1 | 4/2004 | Woloszko et al. |
| 6,736,811 B2 | 5/2004 | Panescu et al. |
| 6,746,447 B2 | 6/2004 | Davison et al. |
| 6,758,847 B2 | 7/2004 | Maguire |
| 6,780,178 B2 | 8/2004 | Palanker et al. |
| 6,802,839 B2 | 10/2004 | Behl |
| 6,813,520 B2 | 11/2004 | Truckai et al. |
| 6,814,730 B2 | 11/2004 | Li |
| 6,832,996 B2 | 12/2004 | Woloszko et al. |
| 6,837,887 B2 | 1/2005 | Woloszko et al. |
| 6,840,935 B2 | 1/2005 | Lee |
| 6,872,205 B2 | 3/2005 | Lesh et al. |
| 6,896,674 B1 | 5/2005 | Woloszko et al. |
| 6,923,805 B1 | 8/2005 | LaFontaine et al. |
| 6,929,642 B2 | 8/2005 | Xiao et al. |
| 6,949,096 B2 | 9/2005 | Davison et al. |
| 6,951,569 B2 | 10/2005 | Nohilly et al. |
| 6,954,977 B2 | 10/2005 | Maguire et al. |
| 6,960,203 B2 | 11/2005 | Xiao et al. |
| 7,074,217 B2 | 7/2006 | Strul et al. |
| 7,083,614 B2 | 8/2006 | Fjield et al. |
| 7,087,052 B2 | 8/2006 | Sampson et al. |
| 7,118,590 B1 | 10/2006 | Cronin |
| 7,179,255 B2 | 2/2007 | Lettice et al. |
| 7,186,234 B2 | 3/2007 | Dahla et al. |
| 7,192,430 B2 | 3/2007 | Truckai et al. |
| 7,238,185 B2 | 7/2007 | Palanker et al. |
| 7,270,658 B2 | 9/2007 | Woloszko et al. |
| 7,276,063 B2 | 10/2007 | Davison et al. |
| 7,294,126 B2 | 11/2007 | Sampson et al. |
| 7,297,143 B2 | 11/2007 | Woloszko et al. |
| 7,326,201 B2 | 2/2008 | Fjield et al. |
| 7,331,957 B2 | 2/2008 | Woloszko et al. |
| RE40,156 E | 3/2008 | Sharps et al. |
| 7,371,231 B2 | 5/2008 | Rioux et al. |
| 7,371,235 B2 | 5/2008 | Thompson et al. |
| 7,381,208 B2 | 6/2008 | van der Walt et al. |
| 7,387,628 B1 | 6/2008 | Behl et al. |
| 7,407,502 B2 | 8/2008 | Strul et al. |
| 7,419,500 B2 | 9/2008 | Marko et al. |
| 7,452,358 B2 | 11/2008 | Stern et al. |
| 7,462,178 B2 | 12/2008 | Woloszko et al. |
| 7,500,973 B2 | 3/2009 | Vancelette et al. |
| 7,512,445 B2 | 3/2009 | Truckai et al. |
| 7,530,979 B2 | 5/2009 | Ganz et al. |
| 7,549,987 B2 | 6/2009 | Shadduck |
| 7,556,628 B2 | 7/2009 | Utley et al. |
| 7,566,333 B2 | 7/2009 | Van Wyk et al. |
| 7,572,251 B1 | 8/2009 | Davison et al. |
| 7,604,633 B2 | 10/2009 | Truckai et al. |
| 7,625,368 B2 | 12/2009 | Schechter et al. |
| 7,674,259 B2 | 3/2010 | Shadduck |
| 7,678,106 B2 | 3/2010 | Lee |
| 7,708,733 B2 | 5/2010 | Sanders et al. |
| 7,717,909 B2 | 5/2010 | Strul et al. |
| 7,736,362 B2 | 6/2010 | Eberl et al. |
| 7,749,159 B2 | 7/2010 | Crowley et al. |
| 7,824,405 B2 | 11/2010 | Woloszko et al. |
| 7,846,160 B2 | 12/2010 | Payne et al. |
| 7,879,034 B2 | 2/2011 | Woloszko et al. |
| 7,918,795 B2 | 4/2011 | Grossman |
| 7,985,188 B2 | 7/2011 | Felts et al. |
| 8,197,476 B2 | 6/2012 | Truckai |
| 8,197,477 B2 | 6/2012 | Truckai |
| 8,540,708 B2 | 9/2013 | Truckai et al. |
| 2002/0022870 A1 | 2/2002 | Truckai et al. |
| 2002/0068934 A1 | 6/2002 | Edwards et al. |
| 2002/0082635 A1 | 6/2002 | Kammerer et al. |
| 2003/0130655 A1 | 7/2003 | Woloszko et al. |
| 2003/0153905 A1 | 8/2003 | Edwards et al. |
| 2003/0171743 A1 | 9/2003 | Tasto et al. |
| 2003/0208200 A1 | 11/2003 | Palanker et al. |
| 2004/0002702 A1 | 1/2004 | Xiao et al. |
| 2004/0010249 A1 | 1/2004 | Truckai et al. |
| 2004/0087936 A1 | 5/2004 | Stern et al. |
| 2004/0215180 A1 | 10/2004 | Starkebaum et al. |
| 2004/0215182 A1 | 10/2004 | Lee |
| 2004/0215296 A1 | 10/2004 | Ganz et al. |
| 2004/0230190 A1 | 11/2004 | Dahla et al. |
| 2005/0075630 A1 | 4/2005 | Truckai et al. |
| 2005/0165389 A1 | 7/2005 | Swain et al. |
| 2005/0182397 A1 | 8/2005 | Ryan |
| 2005/0192652 A1 | 9/2005 | Cioanta et al. |
| 2005/0228372 A1 | 10/2005 | Truckai et al. |

(56) References Cited

U.S. PATENT DOCUMENTS

| | | |
|---|---|---|
| 2005/0240176 A1 | 10/2005 | Oral et al. |
| 2005/0251131 A1 | 11/2005 | Lesh |
| 2006/0009756 A1 | 1/2006 | Francischelli et al. |
| 2006/0052771 A1 | 3/2006 | Sartor et al. |
| 2006/0089637 A1 | 4/2006 | Werneth et al. |
| 2006/0189971 A1 | 8/2006 | Tasto et al. |
| 2006/0189976 A1 | 8/2006 | Karni et al. |
| 2006/0224154 A1 | 10/2006 | Shadduck et al. |
| 2006/0259025 A1 | 11/2006 | Dahla |
| 2007/0021743 A1 | 1/2007 | Rioux et al. |
| 2007/0083192 A1 | 4/2007 | Welch |
| 2007/0161981 A1 | 7/2007 | Sanders et al. |
| 2007/0213704 A1 | 9/2007 | Truckai et al. |
| 2007/0282323 A1 | 12/2007 | Woloszko et al. |
| 2007/0287996 A1 | 12/2007 | Rioux |
| 2007/0288075 A1 | 12/2007 | Dowlatshahi |
| 2007/0293853 A1 | 12/2007 | Truckai et al. |
| 2008/0058797 A1 | 3/2008 | Rioux |
| 2008/0097425 A1 | 4/2008 | Truckai |
| 2008/0125765 A1 | 5/2008 | Berenshteyn et al. |
| 2008/0125770 A1 | 5/2008 | Kleyman |
| 2008/0154238 A1 | 6/2008 | McGuckin |
| 2008/0208189 A1 | 8/2008 | Van Wyk et al. |
| 2008/0221567 A1 | 9/2008 | Sixto, Jr. |
| 2008/0249518 A1 | 10/2008 | Warnking et al. |
| 2009/0048593 A1 | 2/2009 | Ganz et al. |
| 2009/0054888 A1 | 2/2009 | Cronin |
| 2009/0054892 A1 | 2/2009 | Rioux et al. |
| 2009/0076494 A1 | 3/2009 | Azure |
| 2009/0105703 A1 | 4/2009 | Shadduck |
| 2009/0131927 A1 | 5/2009 | Kastelein et al. |
| 2009/0149846 A1 | 6/2009 | Hoey et al. |
| 2009/0163908 A1 | 6/2009 | MacLean et al. |
| 2009/0209956 A1 | 8/2009 | Marion |
| 2009/0306654 A1 | 12/2009 | Garbagnati |
| 2010/0004595 A1 | 1/2010 | Nguyen et al. |
| 2010/0036372 A1 | 2/2010 | Truckai et al. |
| 2010/0042095 A1 | 2/2010 | Bigley et al. |
| 2010/0042097 A1 | 2/2010 | Newton et al. |
| 2010/0049190 A1 | 2/2010 | Long et al. |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114089 A1 | 5/2010 | Truckai et al. |
| 2010/0121319 A1 | 5/2010 | Chu et al. |
| 2010/0125269 A1 | 5/2010 | Emmons et al. |
| 2010/0137855 A1 | 6/2010 | Berjano Zanon et al. |
| 2010/0137857 A1 | 6/2010 | Shiroff et al. |
| 2010/0152725 A1 | 6/2010 | Pearson et al. |
| 2010/0185191 A1 | 7/2010 | Carr et al. |
| 2010/0198214 A1 | 8/2010 | Layton et al. |
| 2010/0204688 A1 | 8/2010 | Hoey et al. |
| 2010/0217256 A1 | 8/2010 | Strul et al. |
| 2010/0228239 A1 | 9/2010 | Freed |
| 2010/0228245 A1 | 9/2010 | Sampson et al. |
| 2010/0286680 A1 | 11/2010 | Kleyman |
| 2011/0004205 A1 | 1/2011 | Chu et al. |
| 2011/0060391 A1 | 3/2011 | Unetich et al. |
| 2011/0112524 A1 | 5/2011 | Stern et al. |
| 2012/0116384 A1 | 5/2012 | Truckai |
| 2012/0130361 A1 | 5/2012 | Toth et al. |
| 2013/0345705 A1 | 12/2013 | Truckai et al. |

FOREIGN PATENT DOCUMENTS

| | | |
|---|---|---|
| WO | WO 00/53112 A2 | 9/2000 |
| WO | WO 2005/122938 A1 | 12/2005 |
| WO | WO 2006/001455 A1 | 1/2006 |
| WO | WO2008/083407 A1 | 7/2008 |
| WO | WO 2011/053599 A1 | 5/2011 |

OTHER PUBLICATIONS

Office action dated Mar. 12, 2012 for U.S. Appl. No. 12/541,050.
Office action dated Sep. 28, 2012 for U.S. Appl. No. 12/541,043.
Office action dated Sep. 28, 2012 for U.S. Appl. No. 12/541,050.
Office action dated Sep. 28, 2012 for U.S. Appl. No. 12/605,929.
Office action dated Dec. 6, 2011 for U.S. Appl. No. 13/281,846.
Office action dated Dec. 22, 2011 for U.S. Appl. No. 13/281,856.
U.S. Appl. No. 13/938,032, filed Jul. 9, 2013, Truckai et al.
U.S. Appl. No. 13/975,139, filed Aug. 23, 2013, Truckai et al.
Office action dated Nov. 6, 2013 for U.S. Appl. No. 13/938,032.
International search report and written opinion dated Dec. 10, 2009 for PCT/US2009/060703.
International search report and written opinion dated Dec. 14, 2010 for PCT/US2010/054150.
International Search Report and Written Opinion of PCT Application No. PCT/US2010/056591, mailed Feb. 2, 2011, 9 pages total.
U.S. Appl. No. 13/857,068, filed Apr. 4, 2013, Shadduck et al.
European search report and search opinion dated Apr. 16, 2013 for EP Application No. 09822443.
European search report and search opinion dated. Jul. 10, 2013 for EP Application No. 10827399.

CONTAINING A NON-CONDUCTIVE GAS WITHIN AN INTERIOR CHAMBER OF AN APPLICATOR HAVING A THIN DIELECTRIC WALL

ENGAGING AN EXTERNAL SURFACE OF THE THIN DIELECTRIC WALL AGAINST A TARGET REGION OF TISSUE

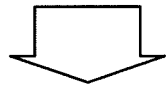

APPLYING RF VOLTAGE ACROSS THE GAS AND DIELECTRIC WALL SUFFICIENT TO INITIATE A PLASMA IN THE GAS AND TO CAPACITIVELY COUPLE CURRENT IN THE GAS ACROSS THE DIELECTRIC WALL INTO TISSUE

FIG. 13

PROVIDING AN APPLICATOR WITH FIRST GAS DIELECTRIC AND SECOND NON-GAS DIELECTRIC IN A SERIES CIRCUIT
ENGAGING THE NON-GAS DIELECTRIC WITH TISSUE
APPLYING SUFFICIENT RF VOLTAGE ACROSS THE CIRCUIT TO CAUSE DIELECTRIC BREAKDOWN IN THE GAS DIELECTRIC TO THEREBY APPLY ABLATIVE ENERGY TO THE TISSUE
FIG. 15

```
┌─────────────────────────────────────────────────────────────────────┐
│ POSITIONING A DIELECTRIC STRUCTURE ENCLOSING AN INTERIOR CHAMBER IN │
│                  CONTACT WITH TARGETED TISSUE                       │
└─────────────────────────────────────────────────────────────────────┘
                                   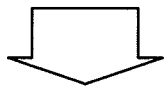
┌─────────────────────────────────────────────────────────────────────┐
│    PROVIDING A GAS MEDIA IN THE INTERIOR CHAMBER HAVING A DEGREE OF │
│                     IONIZATION OF AT LEAST 0.01%                    │
└─────────────────────────────────────────────────────────────────────┘
┌─────────────────────────────────────────────────────────────────────┐
│    APPLYING RF CURRENT THROUGH THE GAS MEDIA TO CAUSE CAPACITIVE    │
│       COUPLING OF ENERGY THROUGH THE DIELECTRIC STRUCTURE           │
└─────────────────────────────────────────────────────────────────────┘
```

FIG. 16

CONTACTING TISSUE WITH A THIN-WALL ENERGY-DELIVERY CONSTRUCT

CAUSING SPATIOTEMPORAL SWITCHING OF FOCAL POINTS OF ENERGY APPLICATION ABOUT THE CONSTRUCT BY COUPLING ENERGY TO SAID FOCAL POINTS WITH TRANSITORY PLASMA STREAMERS

FIG. 44

CONTACTING TISSUE WITH A THIN WALL ENERGY-DELIVERY CONSTRUCT

COUPLING ENERGY THROUGH THE WALL WITH TRANSITORY PLASMA STREAMERS THAT PROVIDE ELECTRON-PERMEABLE FOCAL POINTS IN THE WALL AND CURRENT PATHS AND JOULE HEATING IN THE TISSUE

TISSUE ABLATION SYSTEMS AND METHODS

CROSS-REFERENCES TO RELATED APPLICATIONS

This present application is a non-provisional and claims the benefit of Provisional Application No. 61/307,362, filed on Feb. 23, 2010, and Provisional Application No. 61/261,246, filed on Nov. 13, 2009, the full disclosures of which are incorporated herein by reference. This application is also related to Ser. No. 12/541,043 filed on Aug. 13, 2009 and to Ser. No. 12/541,050 filed on Aug. 13, 2009, both of which are incorporated herein by reference.

BACKGROUND OF THE INVENTION

1. Field of the Invention

The present invention relates to electrosurgical devices and related methods for rapid, controlled ablation of tissue. More particularly, the present invention relates to treating tissue with a radiofrequency current delivered through an electrically non-conductive gas which is ionized to capacitively couple to surrounding tissue through a thin dielectric layer surrounding the gas.

The treatment of diseased organs, such as the uterus and the gallbladder, by ablation of an endometrial or mucosal layer surrounding the interior of the organ has long been proposed. Such internal surface ablation can be achieved by heating the surface, treating the surface with microwave energy, treating the surface with cryoablation, and delivering radiofrequency energy to the surface. Of particular interest to the present invention, a variety of radiofrequency ablation structures have been proposed including solid electrodes, balloon electrodes, metalized fabric electrodes, and the like. While often effective, at least most of the prior electrode designs have suffered from one or more deficiencies, such as relatively slow treatment times, incomplete treatments, non-uniform ablation depths, and risk of injury to adjacent organs.

For these reasons, it would be desirable to provide methods and apparatus for the radiofrequency ablation of internal tissue surfaces which are rapid, provide for uniform ablation depths, which assure complete ablation over the entire targeted surface, and which reduce the risk of injury to adjacent organs. At least some of these objectives will be met by the inventions described hereinbelow.

2. Description of the Background Art

U.S. Pat. No. 4,979,948, describes a balloon filled with an electrolyte solution for distributing radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. Nos. 6,736,811 and 5,925,038 show an inflatable conductive electrode.

BRIEF SUMMARY OF THE INVENTION

The present invention provides methods, apparatus, and systems for treating tissue of a patient. The treatment generally comprises delivering a radiofrequency current to the tissue in order to heat and usually ablate the tissue to a desired depth. Current is delivered to the tissue from a radiofrequency energy source through a first dielectric medium and a second dielectric medium in series with the first medium. The first dielectric medium will usually comprise an electrically non-conductive gas which may be ionized to form a plasma, typically by application of a high voltage radiofrequency voltage, but optionally by the direct application of heat to the gas, further optionally by the application of both the high radiofrequency voltage and heat to the gas. The second dielectric medium will separate the first medium from the target tissue, typically comprising a thin dielectric material, such as silicone or a silicone-based material, more typically comprising a thin dielectric wall which defines an interior chamber which contains the electrically non-conductive gas. The radiofrequency current is thus delivered to the tissue by applying a radiofrequency voltage across the first and second dielectric media so that the first dielectric becomes ionized, typically forming a gas plasma, and the second dielectric allows current flow to the tissue via capacitive coupling.

Methods for treating tissue of a patient in accordance with the present invention comprise containing an electrically non-conductive gas in an interior chamber of an applicator having a thin dielectric wall surrounding at least a portion of the interior chamber. An external surface of the thin dielectric wall is engaged against a target region of the tissue, and a radiofrequency voltage is applied across the gas and thin wall, where the voltage is sufficient to ionize the gas to initiate a plasma in the gas and to capacitively couple the current in the gas plasma across the dielectric wall and into the engaged tissue.

The electrically non-conductive gas may be held statically within the chamber, but will more often be actively flowing through the chamber of the applicator. The flow rate of the non-conductive gas will typically be in the range from about 1 ml/sec to 50 ml/sec, preferably from 10 ml/sec to 30 ml/sec. The interior chamber will have a volume in the range from 0.01 ml to 100 ml, typically from 2 ml to 10 ml. Usually, the electrically non-conductive gas will be argon or another noble gas or mixture of noble gases.

The dielectric wall of the applicator may assume a variety of configurations. In a first embodiment, the dielectric wall will have a generally fixed shape that will remain constant regardless of the internal pressurization of the contained gas. Alternatively, the dielectric wall may be elastic, conformable, slack, or otherwise having a changeable shape which can conform to the engaged tissue surface. In some examples, the thin dielectric wall will comprise a balloon or other inflatable structure which is expanded by increasing an internal pressure of the electrically non-conductive gas or other medium. Alternatively, a separate frame, cage, spring, or other mechanical deployment structure could be provided within an elastic or non-elastic conformable thin dielectric wall. In the latter case, the frame or other structure can be configured and reconfigured to shape the thin dielectric wall as desired in the method.

The voltage is applied to the tissue by providing a first electrode surface coupled to the non-conductive gas and a second electrode surface coupled to the patient tissue. A radiofrequency voltage is then applied across the first and second electrodes in order to both ionize the electrically non-conductive gas (forming a plasma) within the interior chamber and to capacitively couple the charged plasma with tissue across the thin dielectric wall.

The voltage applied to the first and second dielectric media will depend on the distance between the first electrode surface and the dielectric wall as well as the resistance between the dielectric wall and the second electrode which is in contact with the tissue, typically being in the range between 500V (rms) and 2500V (rms). In the exemplary embodiments, the first electrode surface will usually be in or on the interior chamber or a gas flow path leading to the interior chamber, and the second electrode surface will be in contact with the patient's tissue, often being disposed on a shaft or other external surface of the treatment device.

In a second aspect of the present invention, apparatus for delivering radiofrequency current to tissue comprises a body having a support end, a working end, and an interior chamber. A thin dielectric wall surrounds at least a portion of the interior chamber and has an external surface disposed at the working end of the body. A gas inlet will be provided to connect to the chamber for delivery of an electrically non-conductive gas, either in a continuously flowing mode or in a static mode. A first electrode structure is provided which has a surface exposed to either the interior chamber or the gas inlet. A second electrode structure is also provided and has a surface adapted to contact tissue, typically being somewhere on the body, more typically being on a handle or shaft portion of the device. The apparatus further includes a radiofrequency power supply connected to apply a radiofrequency voltage across the first and second electrode structures, wherein the voltage is sufficient to initiate ionization of the gas into a plasma within the chamber. The voltage will further be sufficient to capacitively couple the current in the plasma across the dielectric wall and into tissue adjacent the external surface.

The specific structure of the body may vary. In a first example, the dielectric wall may comprise a rigid material, typically selected from the group consisting of a ceramic, glass, and polymer. The rigid material may be formed into a variety of geometries, including a tube, sphere, or the like. Usually, the dielectric wall will have a thickness in the range from about 0.002 in to 0.1 in, usually from 0.005 in to 0.05 in.

In alternative embodiments, the dielectric wall may comprise a conformable material, typically a silicone. Such conformable dielectric walls will typically have a thickness in the range from about 0.004 in to 0.03 in, usually from 0.008 in to 0.015 in. The conformable wall may be non-distensible or may be elastic so that the wall structure may be inflated. For either non-distensible or elastic dielectric walls, the device may further comprise a frame which supports the conformable material, usually where the frame can be expanded and contracted to open and close the dielectric wall.

The apparatus of the present invention will typically also include a shaft or other handle structure connected to the support end of the body. Usually, the shaft will have a lumen which extends into the gas inlet of the body to deliver the electrically non-conductive gas to the chamber. The shaft or handle may also include at least a second lumen for removing the electrically non-conductive gas from the chamber so that the gas may be recirculated in a continuous flow. Often, the first electrode will be at least partly in the first lumen of the device, although it may also be within the chamber or within both the first lumen and the chamber. The second electrode will usually be disposed at least partly over an exterior surface of the device, typically over the shaft, although in certain systems the second electrode could be disposed on a separate dispersal pod.

Apparatus according to the present invention will have an interior chamber volume in the range from 0.01 ml to 20 ml, typically from 1 ml to 10 ml. The dielectric wall will have an area in the range from 1 $mm^2$ to 100 $mm^2$, typically from 5 $mm^2$ to 50 $mm^2$. The first electrode surface will have an area in contact with the electrically non-conductive gas in the range from 0.01 $mm^2$ to 10 $mm^2$, typically from 1 $mm^2$ to 5 $mm^2$. Additionally, the second electrode structure will have an area available to contact tissue in the range from 0.5 $mm^2$ to 50 $mm^2$, usually from 1 $mm^2$ to 10 $mm^2$.

The radiofrequency power supply may be of general construction as often used in electrosurgery. The power supply will typically be configured to deliver a voltage in the range from 500 V (rms) to 2500 V (rms), usually from 600 V (rms) to 1200V (rms), typically at a current in the range from 0.1 A to 1 A, typically from 0.2 A to 0.5 A, and at a frequency in the range from 450 kHz to 550 MHz, usually from 480 kHz to 500 MHz.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 13 is a block diagram of one method corresponding to the invention.

FIG. 15 is a block diagram of another method corresponding to the invention.

FIG. 16 is a block diagram of another method corresponding to the invention.

FIG. 44 is a block diagram of one method corresponding to the invention.

DETAILED DESCRIPTION OF THE INVENTION

Figure 1:
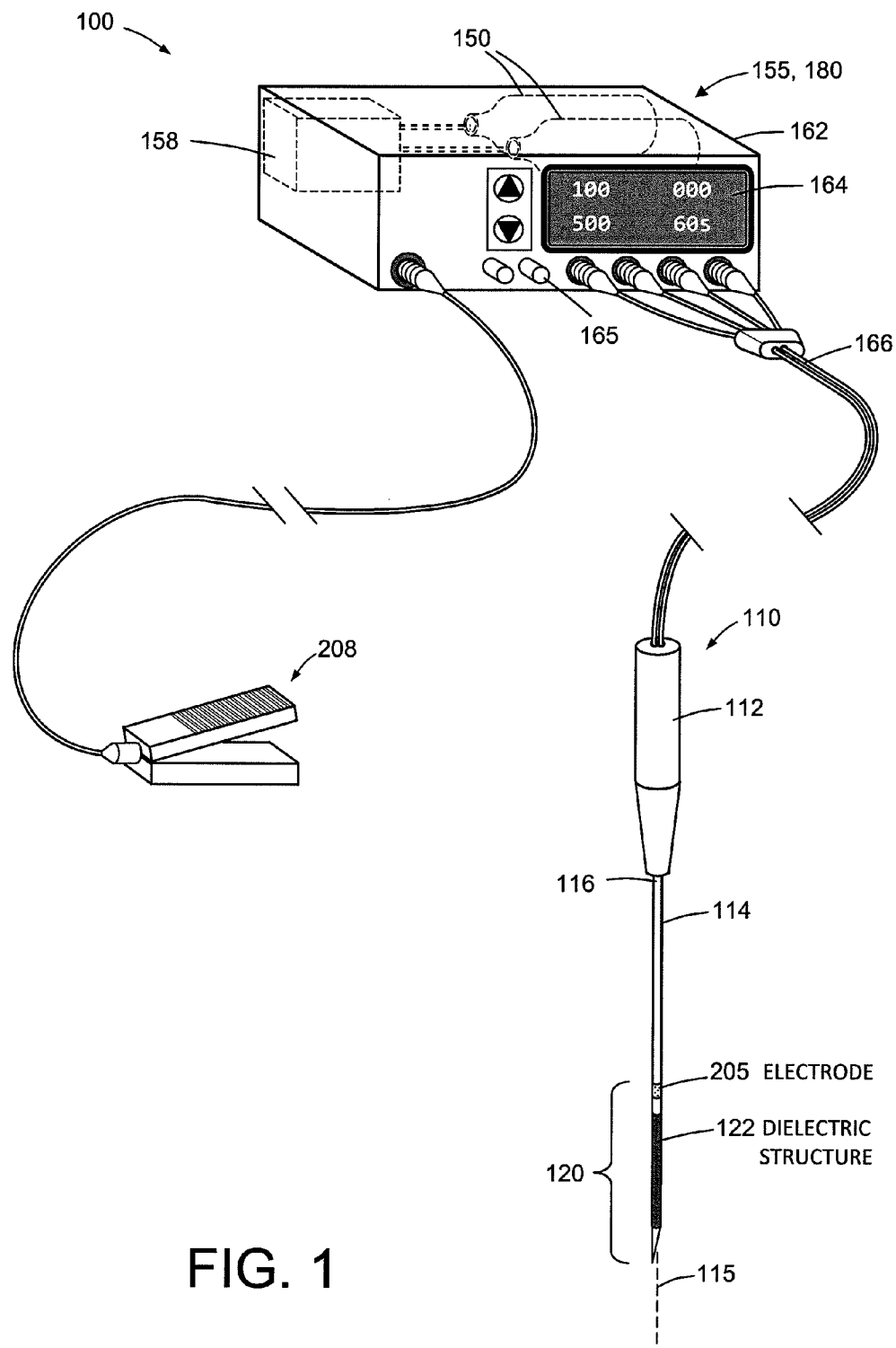
FIG. 1 is a schematic view of an ablation system corresponding to the invention, including an electrosurgical ablation probe, RF power source and controller.

Several embodiments of ablation systems useful for practicing ablation methods corresponding to the present invention are shown in the drawings. In general, each of these embodiments utilizes a neutral gas contained within a chamber that is at least partly enclosed by thin-wall dielectric enclosure, wherein the dielectric wall provides for capacitive coupling of RF current from the gas to through the dielectric to contacted tissue. A second electrode is in contact the tissue at an exterior of the dielectric enclosure. The system embodiments typically include an instrument with a working end including the thin-wall dielectric enclosure for containing an ionizable gas. Current flow to the tissue initiates when sufficient voltage is applied to ionize the contained gas into a plasma and the contemporaneous capacitive coupling through the surrounding dielectric structure occurs. The invention thus provides a voltage-based electrosurgical effect that is capable of ablating tissue to a controlled depth of 1 mm to 5 mm or more very rapidly, wherein the depth of ablation is very uniform about the entire surface of the dielectric enclosure. The instrument working end and dielectric enclosure can take a variety of forms, including but not limited to an elongated shaft portion of a needle ablation device, a dielectric expandable structure, an articulating member, a deflectable member, or at least one engagement surface of an electrosurgical jaw structure. The system embodiments and methods can be used for interstitial tissue ablation, intraluminal tissue ablation or topical tissue ablation.

The system embodiments described herein utilize a thin-wall dielectric structure or wall at an instrument working end that contains an electrically non-conductive gas as a dielectric. The thin-wall dielectric structure can be a polymer, ceramic or glass with a surface configured for contacting tissue. In one embodiment, an interior chamber within the interior of the thin-wall dielectric structure carries a circulating neutral gas or static neutral gas such as argon. An RF power source provides current that is coupled to the neutral gas flow or static gas volume by an electrode disposed within the interior of the working end. The gas flow or static gas contained within the dielectric enclosure is of the type that is non-conductive until it has been transformed to a conductive plasma by voltage breakdown. The threshold voltage for breakdown of the gas will vary with variations in several parameters, including the gas pressure, the gas flow rate, the type of gas, and the distance from the interior electrode across the interior chamber to the dielectric structure. As will be seen in some of the embodiments, the voltage and other operational parameters can be modulated during operation by feedback mechanisms.

The gas, which is ionized by contact with a conductive electrode in the instrument working end, functions as a switching mechanism that only permits current flow into targeted tissue when the voltage across the combination of the gas, the dielectric structure and the contacted tissue reaches a predetermined threshold potential that causes capacitive coupling across the dielectric structure. By this means of permitting current flow only at a high threshold voltage that capacitively couples current to the tissue, the invention allows a substantially uniform tissue effect within all tissue in contact with the dielectric structure. Further, the invention allows the ionized gas to be created contemporaneously with energy application to tissue by the conversion of a non-conductive gas to a plasma.

In one embodiment of the apparatus, the ionized gas functions as an electrode and comprises a gas flow that can conduct current across an internal contained volume of the gas within a dielectric structure, typically from an electrode at an interior of a working end in contact with the gas flow. The gas flow is configured for the purpose of coupling energy to the dielectric structure uniformly across the surface of the dielectric structure, but that will only conduct such energy when the non-conductive gas media has been transformed to a conductive plasma by having been raised to a threshold voltage.

Definitions

Plasma. In general, this disclosure may use the terms "plasma" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, an acts as a conductor which supports electric currents and can form spark or arc. Due to their lower mass, the electrons in a plasma accelerate more quickly in response to an electric field than the heavier positive ions, and hence carry the bulk of the current. A variety of terms are known in the literature to describe a transient plasma discharge across a gas such as plasma filament, plasma streamer, plasma microstreamer, plasma wire or plasma hair. In this disclosure, the terms plasma filament and plasma streamer are used interchangeably herein to describe visible plasma discharges within and across a gas volume. A plasma filament may also be called a dielectric barrier discharge herein when describing a plasma filament generated adjacent to, and as a function of, high voltage current coupling through a dielectric wall.

Dielectric and dielectric loss. The term dielectric is used in its ordinary sense meaning a material that resists the flow of electric current, that is, a non-conducting substance. An important property of a dielectric is its ability to support an electrostatic field while dissipating minimal energy in the form of heat. The lower the dielectric loss (the proportion of energy lost as heat), the more effective is a dielectric material.

Dielectric constant or relative permittivity. The dielectric constant (k) or relative static permittivity of a material under given conditions is a measure of the extent to which it concentrates electrostatic lines of flux, or stated alternatively is a number relating the ability of the material to carry alternating current to the ability of vacuum to carry alternating current. The capacitance created by the presence of a material is directly related to its dielectric constant. In general, a material or media having a high dielectric constant breaks down more easily when subjected to an intense electric field than do materials with low dielectric constants. For example, air or another neutral gas can have a low dielectric constant and when it undergoes dielectric breakdown, a condition in which the dielectric begins to conduct current, the breakdown is not permanent. When the excessive electric field is removed, the gas returns to its normal dielectric state.

Dielectric breakdown. The phenomenon called dielectric breakdown occurs when an electrostatic field applied to a material reaches a critical threshold and is sufficiently intense so that the material will suddenly conduct current. In a gas or liquid dielectric medium, this condition reverses itself if the voltage decreases below the critical point. In solid dielectrics, such a dielectric breakdown also can occur and couple energy through the material. As used herein, the term dielectric breakdown media refers to both solid and gas dielectrics that allow current flow across the media at a critical voltage.

Degree of ionization. Degree of ionization describes a plasma's proportion of atoms which have lost (or gained) electrons, and is controlled mostly by temperature. For example, it is possible for an electrical current to create a degree of ionization ranging from less than 0.001% to more than 50.0%. Even a partially ionized gas in which as little as 0.1% or 1.0% of the particles are ionized can have the characteristics of a plasma, that is, it can strongly respond to magnetic fields and can be highly electrically conductive. For the purposes of this disclosure, a gas may begin to behave like conductive plasma when the degree of ionization reaches approximately 0.1%, 0.5% or 1.0%. The temperature of a plasma volume also relates to the degree of ionization. In particular, plasma ionization can be determined by the electron temperature relative to the ionization energy. A plasma is sometimes referred to as being "hot" if it is nearly fully ionized, or "cold" or a "technological plasma" if only a small fraction (for example, less than 5% or less than 1%) of the gas molecules are ionized. Even in such a cold plasma, the electron temperature can still be several thousand degrees Celsius. In the systems according to the present invention, the plasmas are cold in this sense because the percentage of ionized molecules is very low. Another phrase used herein to describe a "cold" plasma is "average mass temperature" of the plasma which relates to the degree of ionization versus non-ionized gas and which averages the temperatures of the two gas volume components. For example, if 1% of a gas volume is ionized with an electron temperature of 10,000° C., and the remaining 99% has a temperature of 150° C., then the mass average temperature will be 149.5° C. It has been found that measuring the plasma temperature can be used to determine an approximate degree of ionization which can be used for feedback control of applied power, and as a safety mechanism for preventing unwanted high temperatures within a thin-wall dielectric structure.

Referring to FIG. 1, a first embodiment of a tissue ablation system 100 utilizing principles of the present invention is shown. The system 100 includes a probe 110 having a proximal handle 112 and an elongated shaft or extension member 114 that extends along axis 115. The handle 110 is fabricated of an electrically insulative material such as a plastic, ceramic, glass or combination thereof. The extension member 114 has a proximal end 116 coupled to handle 112. The extension member 114 extends to a distal working end 120 that includes a dielectric member or structure 122 that is configured for contacting tissue that is targeted for ablation.

Figures 2A, 2B:
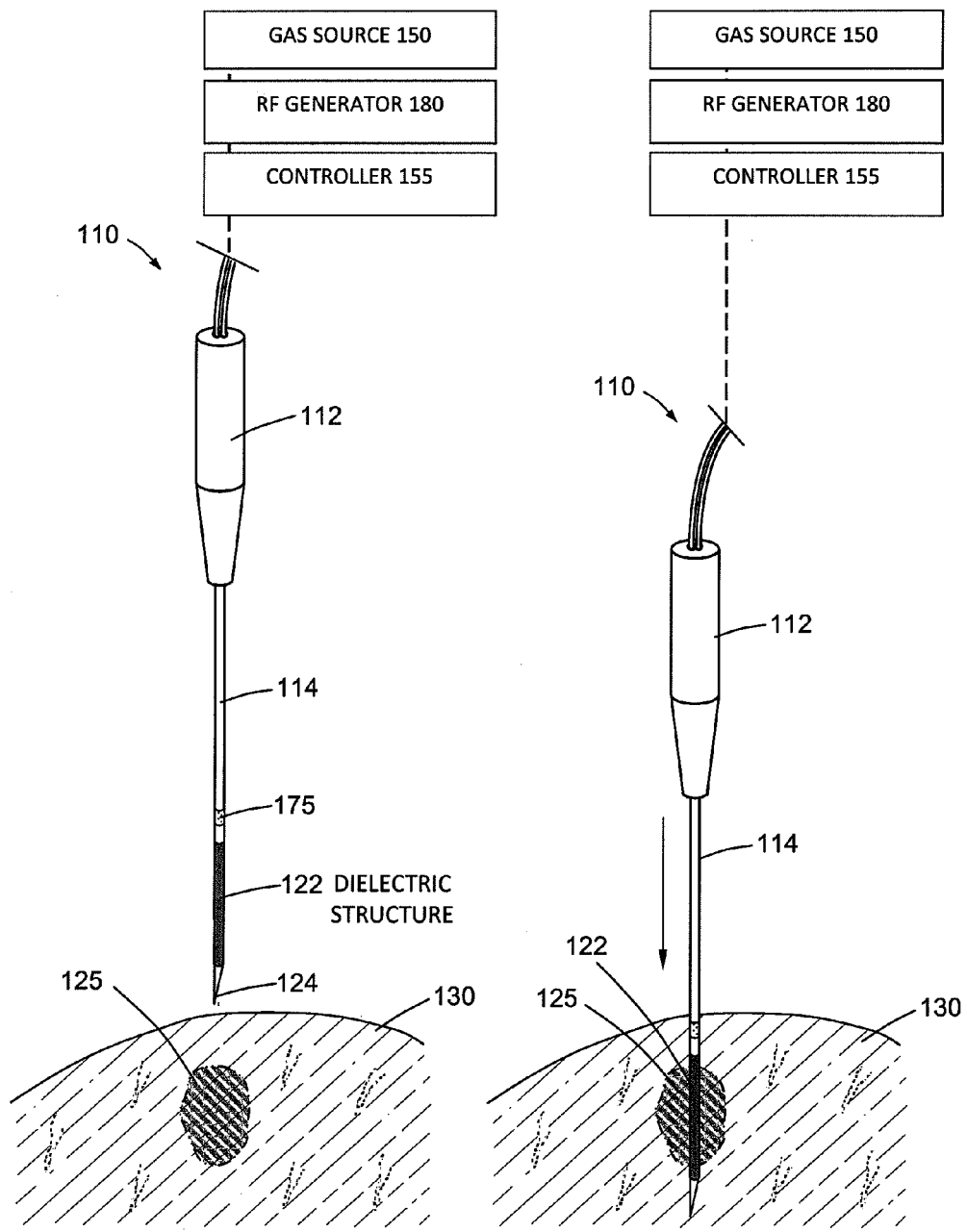
FIG. 2A is a view of the ablation probe of FIG. 1 configured with a sharp tip for ablation of a tumor.
FIG. 2B is another view of the probe of FIG. 2A after being penetrated into the tumor.

In the embodiment of FIG. 1, the working end 120 and dielectric structure 122 is elongated and cylindrical with a cross-section ranging from about 0.5 mm to 5 mm or more with a length ranging from about 1 mm to 50 mm. The cross-section of the working end 120 can be round, oval, polygonal, rectangular or any other cross-section. As can be seen in FIGS. 2A-2B, in one embodiment, the working end 120 has a sharp tip 124 for penetrating tissue to perform an ablation procedure, such as ablating a tumor indicated at 125 in a tissue volume 130. In other embodiment, the distal tip of a working end 120 can be blunt. In yet other embodiment, the entire working end can have a guide channel therein for advancing the working end over a guide wire.

Figure 3:
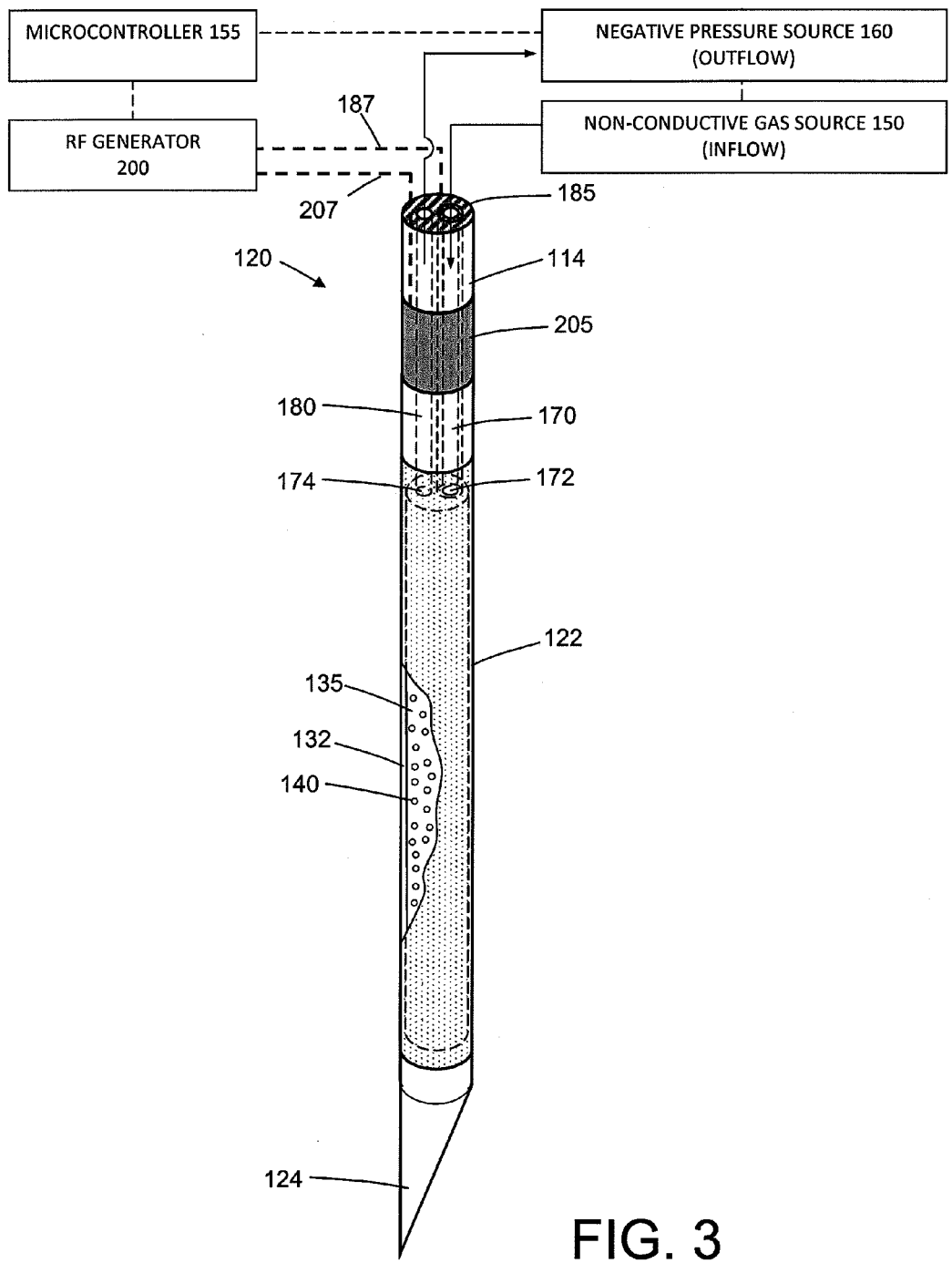
FIG. 3 is an enlarged schematic view of the working end of the probe of FIG. 1 that provides a gas electrode within an interior of a thin-wall dielectric structure.
Figure 4A:
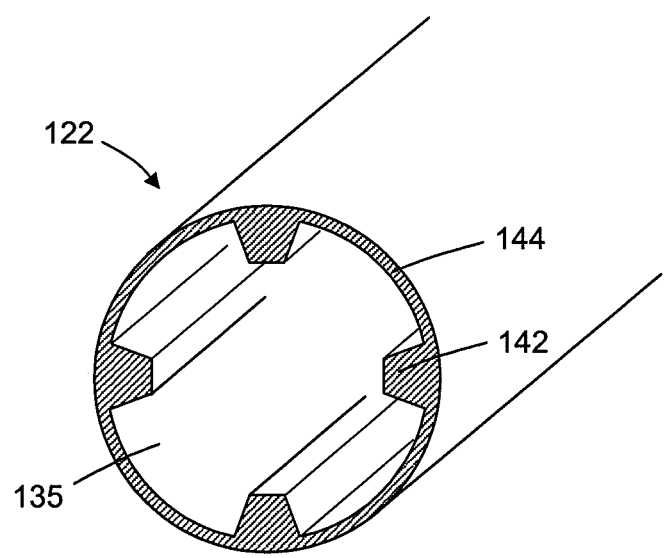
FIG. 4A is a sectional view of an alternative thin-wall cylindrical dielectric structure in which support elements are formed within the dielectric structure.
Figure 4B:
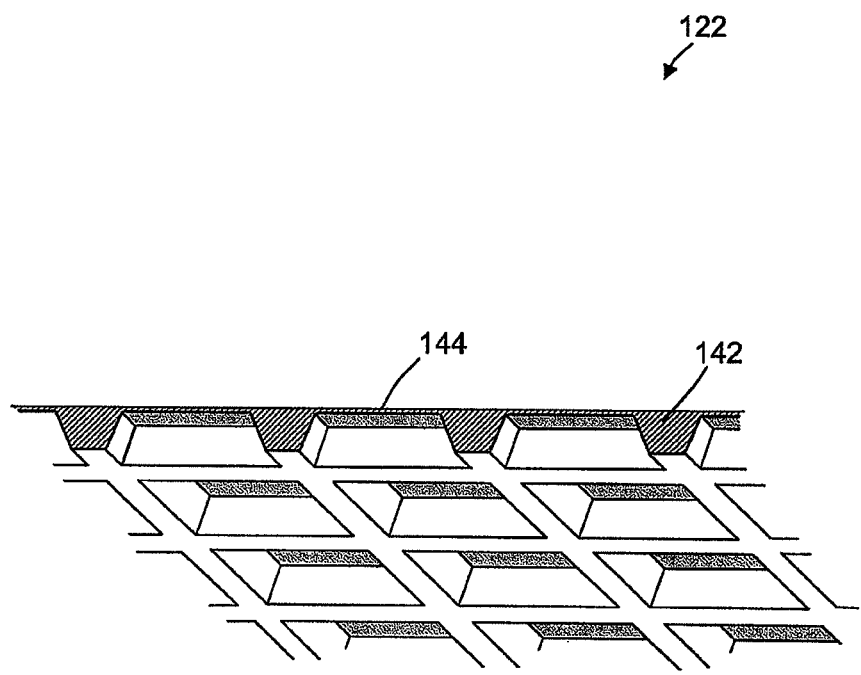
FIG. 4B is a sectional view of a portion of another thin-wall planar dielectric structure in which support elements are in a waffle-like configuration.
Figure 5A:
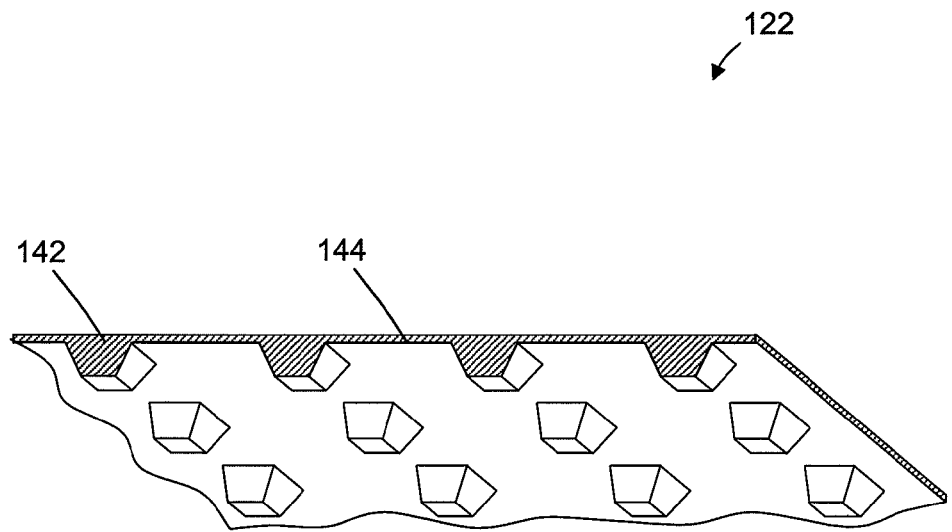
FIG. 5A is a sectional view of a portion of another thin-wall planar dielectric structure in which support elements comprise post-like elements.
Figure 5B:
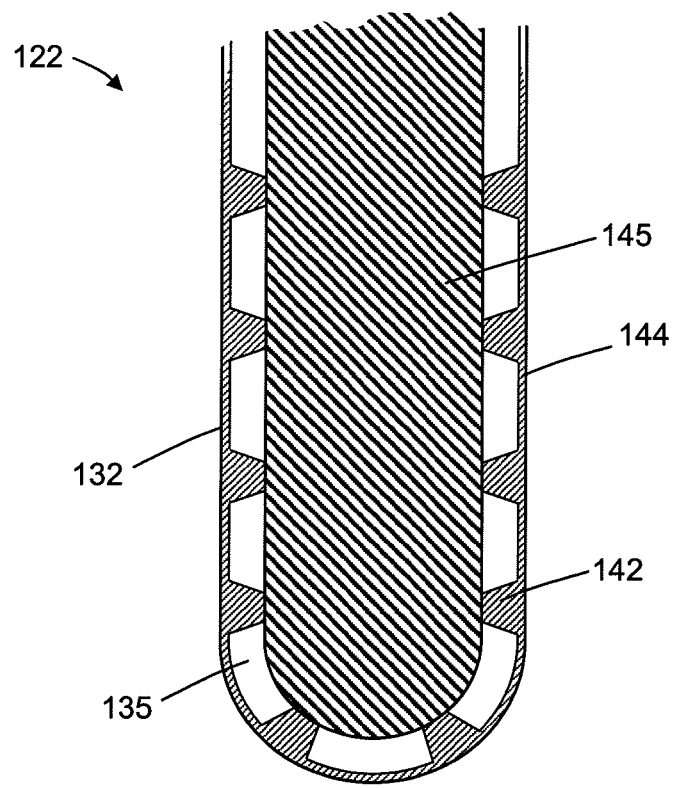
FIG. 5B is a sectional view of a probe working end in which a thin-wall dielectric structure with post-like support elements are provided around core electrode.

Now turning to FIG. 3, an enlarged view of the working end 120 of FIGS. 1, 2A and 2B is shown. It can be seen that the dielectric structure 122 has a thin wall 132 that provides an enclosure about an interior chamber 135 that contains a gas media indicated at 140 in FIG. 3. In one embodiment, the dielectric structure 122 can comprise a ceramic (e.g., alumina) that has a dielectric constant ranging from about 3 to 4. The thickness of wall 132 can range from 0.002" to 0.10" depending on the diameter, or more typically 0.005" to 0.050" in a diameter ranging from 1 to 4 mm. In other embodiment shown in FIG. 4A, the dielectric structure 122 can comprise a ceramic, glass or polymer in a molded form with strengthening support portions 142 or ribs that end axially, radially, helically or a combination thereof. The support portions 142 alternatively can comprise members that are independent of a thin-wall 132 of a dielectric material. In such an embodiment (FIG. 4A) as will be described below, the thin wall portions 144 of the dielectric structure 122 permit capacitive coupling of current to tissue while the support portions 142 provide structural strength for the thin-wall portions 144. In another embodiment, a portion of which is shown in FIG. 4B, the dielectric structure 122 has support portions 142 in a waffle-like configuration wherein thin-wall portions 144 are supported by thicker wall support portions 142. The waffle-like structure can be substantially planar, cylindrical or have any other suitable configuration for containing a gas dielectric in a chamber indicated at 135 on one side of the dielectric structure 122. In another embodiment of FIGS. 5A and 5B, the dielectric structure 122 can have support portions 142 comprising posts that support the thin-wall portions 144 over another supporting member 145. The planar dielectric structure 122 can be used, for example, in planar jaw members for applying RF energy to seal tissue. In another example, FIG. 5B shows a blunt-tipped, cylindrical thin wall 132 of a dielectric structure 122 supported by a core supporting member 145. In the embodiment of FIG. 5B, the interior chamber 135 which can contain a plasma comprises a space between the thin wall portions 144 and the core support member 145.

Figure 6:
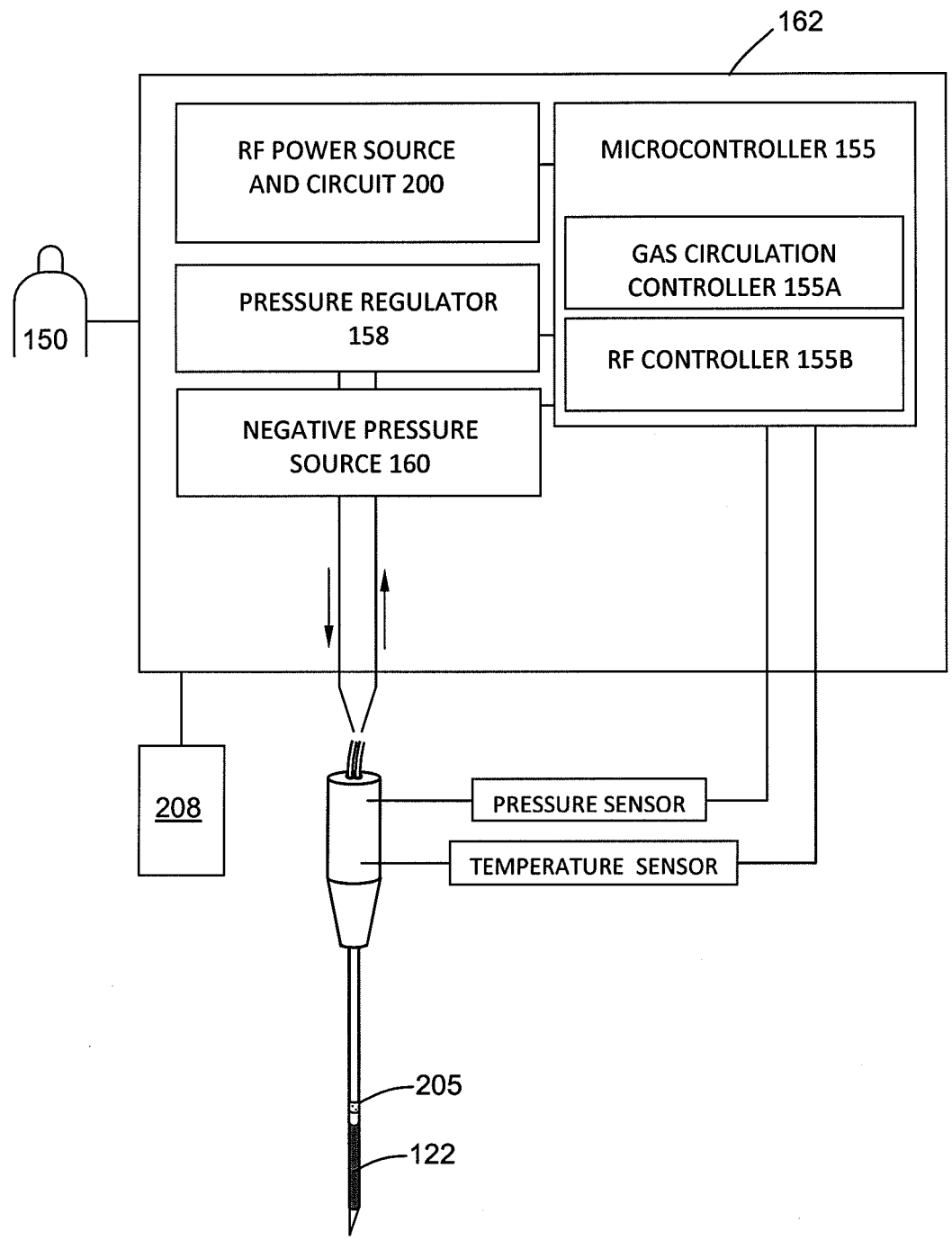
FIG. 6 is a block diagram of components of one an electrosurgical system corresponding to the invention.

Referring again to FIG. 3, the extension member 114 is fabricated of an electrically non-conductive material such as polymer, ceramic, glass or a metal with an insulative coating. The dielectric structure 122 can be bonded to extension member 114 by glues, adhesives or the like to provide a sealed, fluid-tight interior chamber 135. In one embodiment, a gas source 150 can comprise one or more compressed gas cartridges (FIGS. 1 and 6). As will be described below (FIG. 6), the gas source is coupled to a microcontroller 155 that includes a gas circulation subcontroller 155A which controls a pressure regulator 158 and also controls an optional negative pressure source 160 adapted for assisting in circulation of the gas. The RF and controller box 162 in FIG. 1 can include a display 164 and input controls 165 for setting and controlling operational parameters such as treatment time intervals, gas flows, power levels etc. Suitable gases for use in the system include argon, other noble gases and mixtures thereof.

Referring to FIG. 3, the gas source 150 provides a flow of gas media 140 though a flexible conduit 166 to a first flow channel 170 in extension member 114 that communicates with at least one inflow port 172 interfacing with interior chamber 135. The interior chamber 135 also interfaces with an outflow port 174 and second flow channel 180 in extension member 114 to thereby allow a circulating flow of gas media 140 within the interior of dielectric structure 122.

Still referring to FIG. 3, a first polarity electrode 185 is disposed about flow channel 170 proximate to the inflow port 172 thus being in contact with a flow of gas media 140. It should be appreciated that electrode 185 can be positioned in any more proximal location in channel 170 in contact with the gas flow, or the electrode 185 can be within interior chamber 135 of dielectric structure 122. The electrode 185 is electrically coupled to a conductor or lead 187 that extends through the extension member and handle 112 and is coupled to a first pole of a high frequency RF generator 200 which is controlled by controller 155 and RF subcontroller 155B. An opposing polarity electrode 205 is disposed on the exterior surface of extension member 114 and is electrically coupled by lead 207 to a second pole of RF generator 200.

Figure 7:
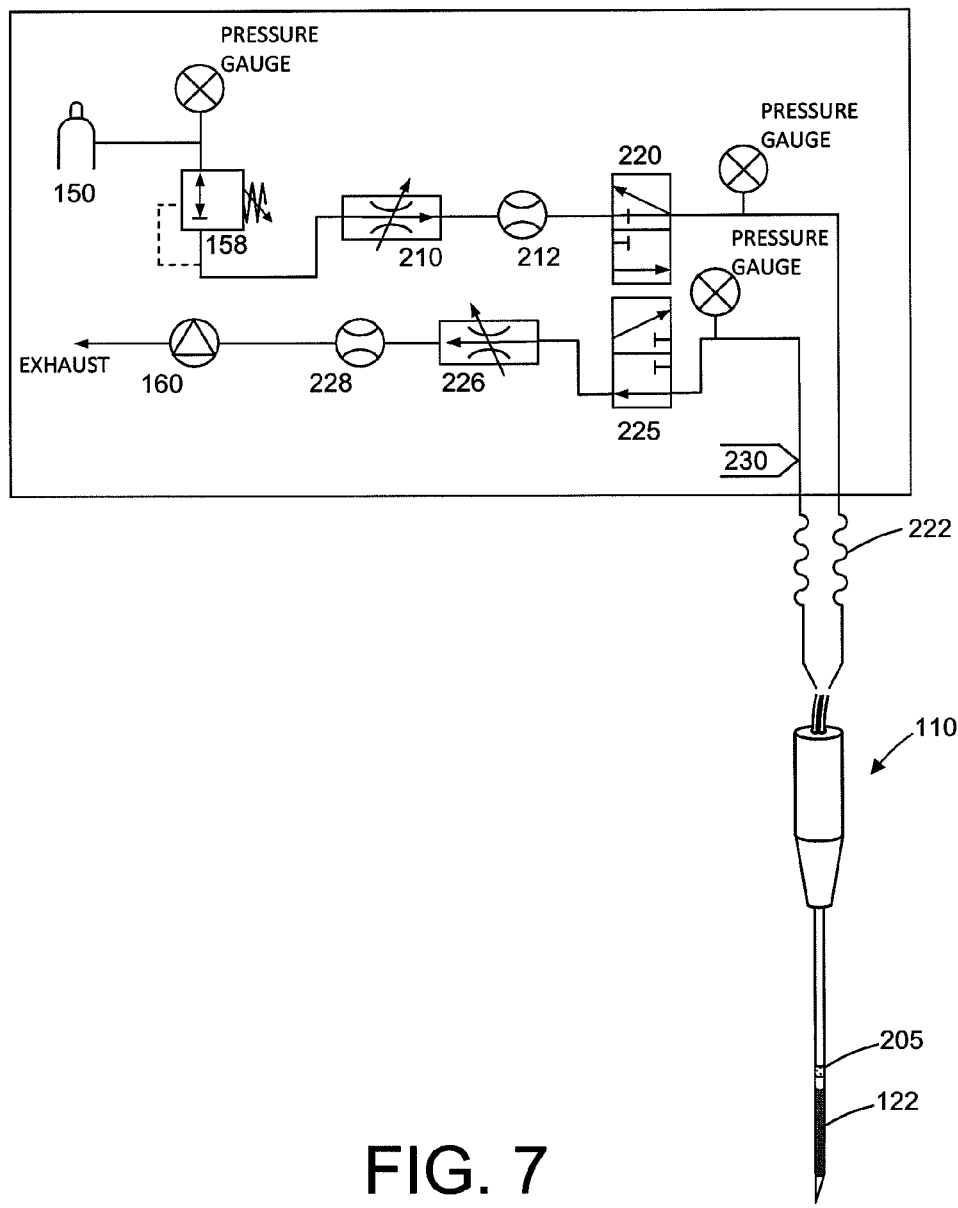
FIG. 7 is a block diagram of gas flow components of an electrosurgical system corresponding to the invention.

The box diagrams of FIGS. 6 and 7 schematically depict the system, subsystems and components of one embodiment that is configured for delivering ablative electrosurgical energy to tissue. In the box diagram of FIG. 6, it can be seen that an RF power source 200 and circuit is controlled by RF subcontroller 155B. Feedback control subsystems (described below) based on systems and probe pressure feedback, probe temperature feedback, and/or gas flow rate feedback are also operatively coupled to controller 155. The system can be actuated by footswitch 208 or another suitable switch. FIG. 7 shows a schematic of the flow control components relating to the flow of gas media through the system and probe 110. It can be seen that a pressurized gas source 150 in linked to a downstream pressure regulator 158, an inflow proportional valve 210, flow meter 212 and normally closed solenoid valve 220. The valve 220 is actuated by the system operator which then allows a flow of gas media 140 to circulate through flexible conduit 166 and probe 110. The gas outflow side of the system includes a normally open solenoid valve 225, outflow proportional valve 226 and flowmeter 228 that communicate with negative pressure source 160. The exhaust of the gas can be into the environment or into a containment system. A temperature sensor 230 (e.g., thermocouple) is shown in FIG. 7 for monitoring the temperature of outflow gases.

Figure 8:
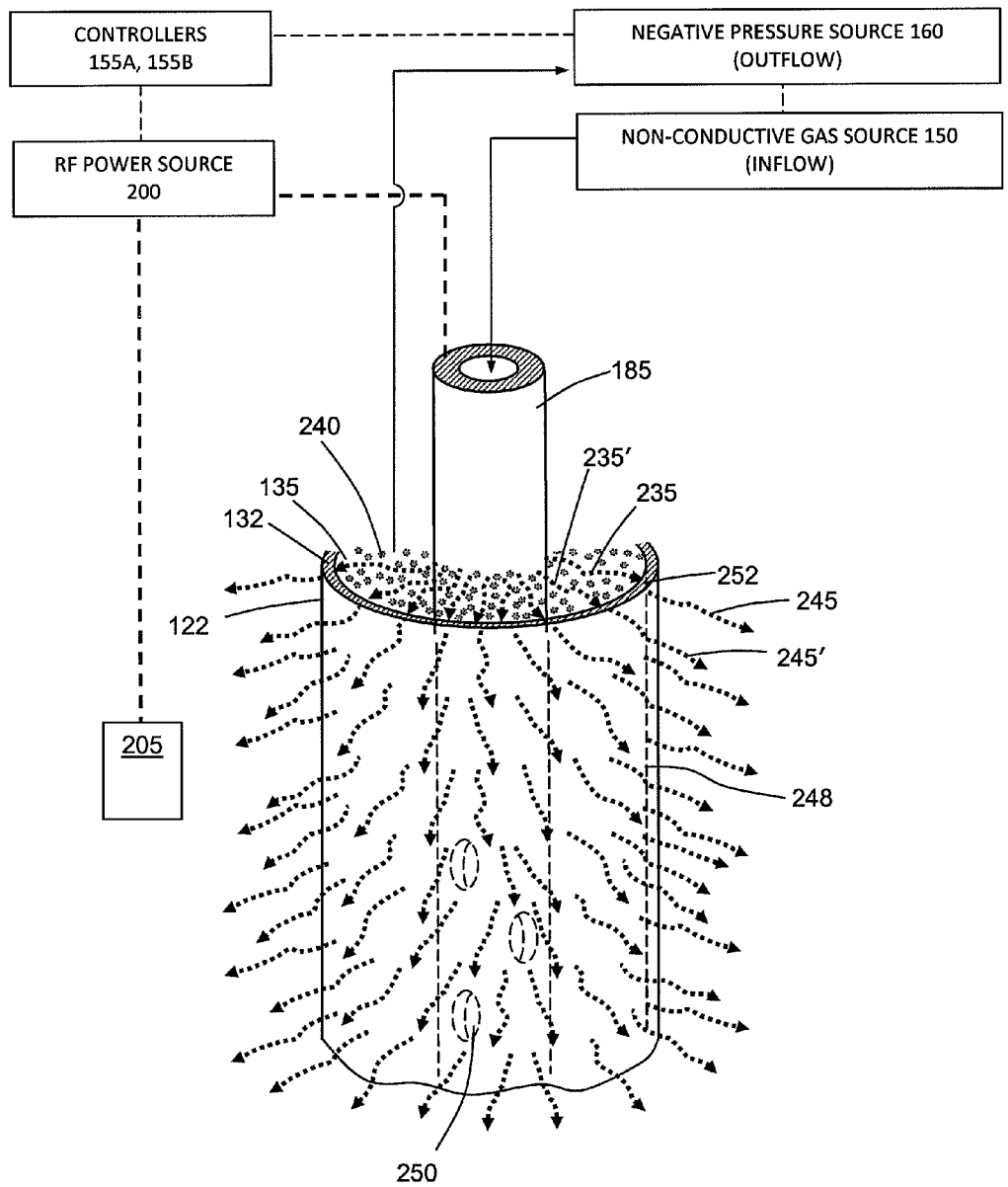
FIG. 8 is a cut-away schematic view of a working end as in FIG. 3 illustrating a step in a method of the invention wherein current is coupled to tissue via a spark gap (or gas electrode) and capacitive coupling through a thin-wall dielectric structure.

FIGS. 8 and 9A-9D schematically illustrate a method of the invention wherein (i) the dielectric structure 122 and (ii) the contained neutral gas volume 140 function contemporaneously to provide first and second dielectric media that cooperatively function as independent mechanisms to couple high voltage current to tissue in contact with the thin-wall dielectric 132. The two dielectric components can be characterized as having complementary voltage thresholds levels at which only high voltage current can couple through a plasma filament or streamer 235 in plasma 240 within chamber 135 and capacitively couple through the thin-wall dielectric 132 to allow a current to further pass through a least resistive path 245 in the engaged tissue. In FIG. 8, the engaged tissue is assumed to be surrounding the dielectric structure 122 and is transparent. In the embodiment of FIG. 8, the electrode 185 is tubular and functions and a gas delivery sleeve wherein a neutral gas 140 can exit ports 250 in chamber 135. The high voltage current paths 245 in plasma filaments scan or move across and about the inner surface 248 of the dielectric structure 122 and within paths in the contacted tissue which can deliver a voltage-maximized current causing Joule heating in the tissue. FIG. 8 provides a schematic view of what is meant by the terminology or plasma filament "scanning" the interior surface of the dielectric 132 wherein high intensity electrical fields are produced in interior chamber 135 of dielectric structure 122 by capacitive coupling through the dielectric wall 132 until a voltage threshold is reached in the neutral gas media 140 to convert the gas into a plasma 240 (see FIG. 8) which in turn allows plasma filaments 235 to form within the chamber 135 which randomly move or scan about the interior surface 248 of the dielectric wall. In one embodiment, movement or scanning of such plasma filaments 235 within the chamber 135 (from electrode 185 to inner surface 248 of dielectric wall 132) is spatiotemporally chaotic and the discharge occurs where there is a transient, reversible voltage breakdown in a localized portion 252 of the dielectric wall 132, which is determined by a transient highest conduction path 240 in engaged tissue to the second polarity electrode 205 (FIG. 3). An instant after the flow of current through the plasma 240 and path 245 in tissue, the localized portion 252 dissipates the electrical field and another capacitive coupling occurs through another plasma filament 235' and current path 245' in tissue to cause electrosurgical ablation in another random, discrete location. In another embodiment, the plasma filaments can be very fine resulting in the appearance of a glow discharge within chamber 135 instead of spaces apart discrete plasma filaments.

Figure 9A:
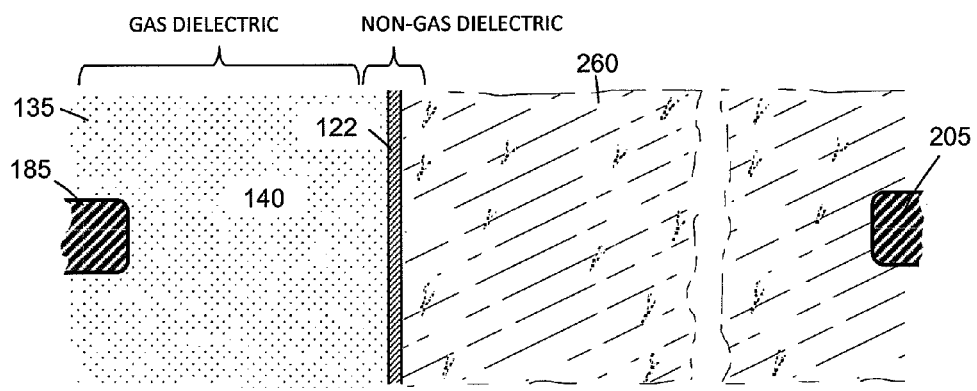
FIG. 9A is an enlarged schematic view of an aspect of the method of FIG. 3 illustrating the step positioning an ionized gas electrode and thin-wall dielectric in contact with tissue.

FIGS. 9A-9D are enlarged schematic illustrations of the electrosurgical ablation method of FIG. 8 that depict other aspects of the ablation method. In FIG. 9A, it can be seen that the system and method is generalized to show clearly the first and second dielectric current transmission mechanisms characterized by selected voltage parameters to cause an electron avalanche in the gas and capacitive coupling in the thin-wall enclosure to optimize and maximize a form of high voltage current delivery to an exemplary tissue 260. As described previously, the voltage threshold or dielectric breakdown mechanisms occur within (i) the gas dielectric or neutral gas volume 140 that is contained within an interior chamber 135 of dielectric structure 122 and (ii) the non-gas dielectric or structure 122 shown as a plane in FIGS. 9A-9D.

FIG. 9A illustrates the working end components and tissue 260 prior to the actuation and delivery of energy to the tissue. It can be seen that the gas media 140 is neutral and not yet ionized. The first polarity electrode 185 positioned in the interior chamber 135 in contact with neutral gas 140 is shown schematically. The second polarity electrode 205 in contact with tissue is also shown schematically, but the illustration represents another aspect of the invention in that the second electrode 205 can have a small surface area compared to the surface areas of return electrodes/ground pads as in conventional electrosurgical systems. It has been found that the capacitively coupled energy delivery mechanism of the invention does not cause tissue heating at or about the surface of the second polarity electrode 205 as would be expected in a conventional electrosurgical device. As will be described below, it is believed that the constant flux in voltage breakdown-initiated and capacitive coupling-initiated current paths in the tissue 260 greatly reduces heat built up at or about the return electrode 205.

Figure 9B:
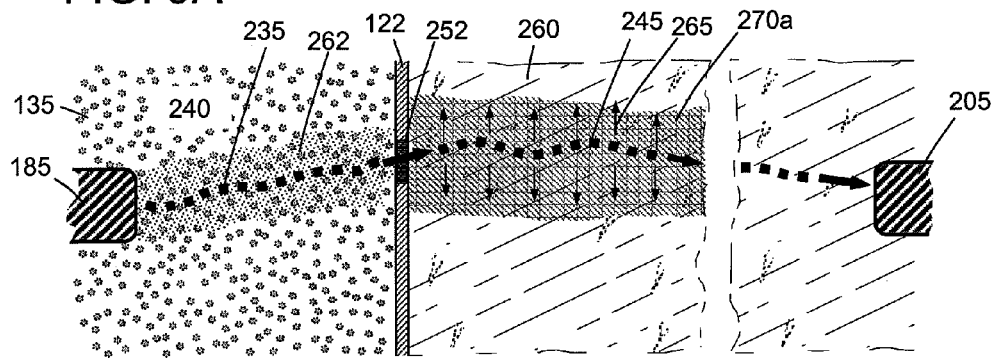
FIG. 9B is a schematic view of a subsequent step of applying RF energy to create an arc across a gas and capacitive coupling through the thin-wall dielectric to cause current flow in a discrete path in tissue.

FIG. 9B illustrates the working end components and tissue 260 at an instant in time immediately after the operator actuates the system and delivers power to the probe working end. Several aspects of the voltage-initiated breakdown ablation method are represented in FIG. 9B, including (i) in one aspect of the instant in time, the neutral gas 140 is converted to a plasma 240 by potential between the first and second polarity electrodes 185 and 205; and contemporaneously (ii) current flow defines a least resistive path 245 in the tissue 260; (iii) a portion 252 of dielectric structure 122 adjacent current path 245 allows capacitive coupling to the tissue; (iv) the plasma filament 235 arcs across a high intensity plasma stream 262 between electrode 185 and the portion 252 of the dielectric structure. In other words, when the a selected voltage potential is reached, the voltage breakdown of the gas 140 and capacitively coupling through the dielectric 122 causes a high voltage current to course through path 245 in the tissue 260. An instant later, thermal diffusion indicated by arrows 265 causes thermal effects in a tissue volume 270a outward from the transient current path 245. The thermal effects in and about path 245 elevates tissue impedance, which thus causes the system to push a conductive path to another random location.

Figure 9C:
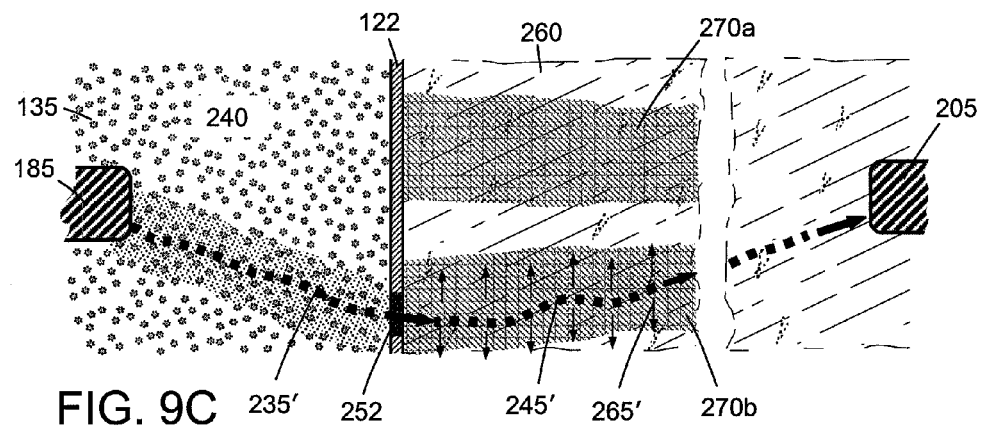
FIG. 9C is a schematic view similar to FIG. 9B depicting the scanning of current flow to another random path in the tissue.

FIG. 9C illustrates the working end components and tissue 260 an instant after that of FIG. 9B when continued voltage potential causes voltage breakdown in plasma filament 235' together with capacitively coupling through dielectric 122 to provide another high voltage current to course through path 245' after which heat diffusion 265' causes thermal effects indicated at 270b. The "scanning" aspect of the ablation method can be understood from FIGS. 9A-9B wherein the plasma filaments 235, 235' and current paths very rapidly jump or scan about the interior chamber 135 to thereby deliver current in a path of least resistance 245, 245' in the tissue 260.

Figure 9D:
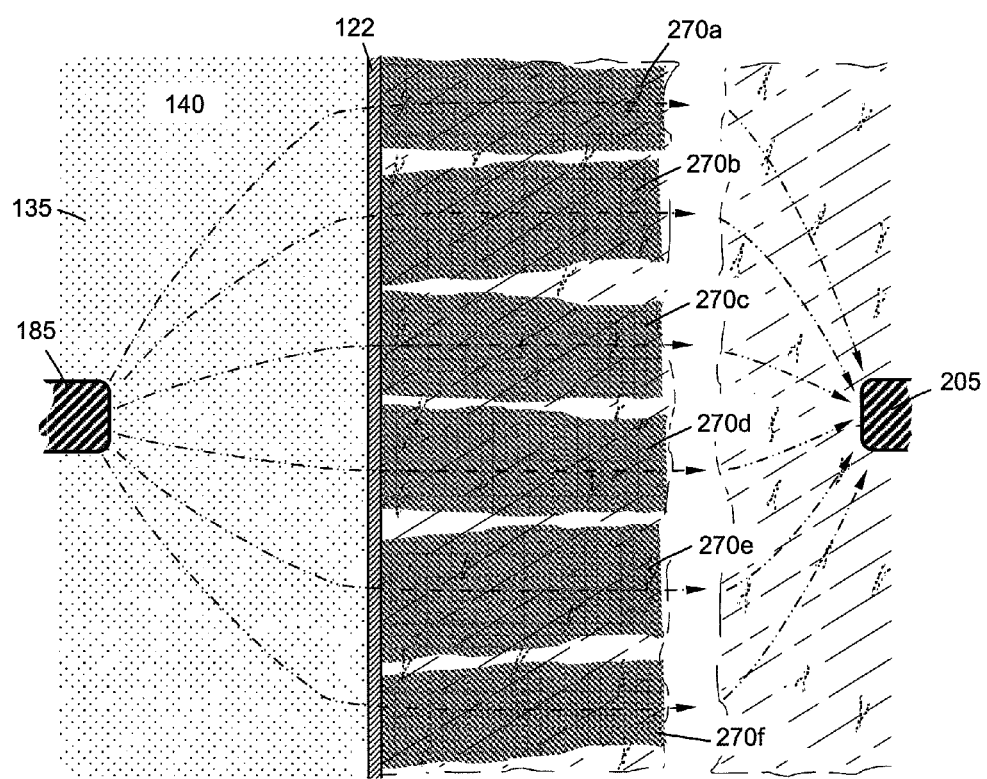
FIG. 9D is a schematic view similar to FIGS. 9A-9C depicting the thermal diffusion from the plurality of scanned current flows in the tissue.

Now turning to FIG. 9D, another schematic is shown following an interval of energy delivery in which a multiplicity of current paths through the pre-existing plasma and dielectric 122 have provided thermal effects diffused throughout a multiplicity of regions indicated at 270a-270f. By this method, it has been found that ablation depths of 3 mm to 6 mm can be accomplished very rapidly, in for example 30 seconds to 90 seconds dependent upon the selected voltage.

Figure 10:
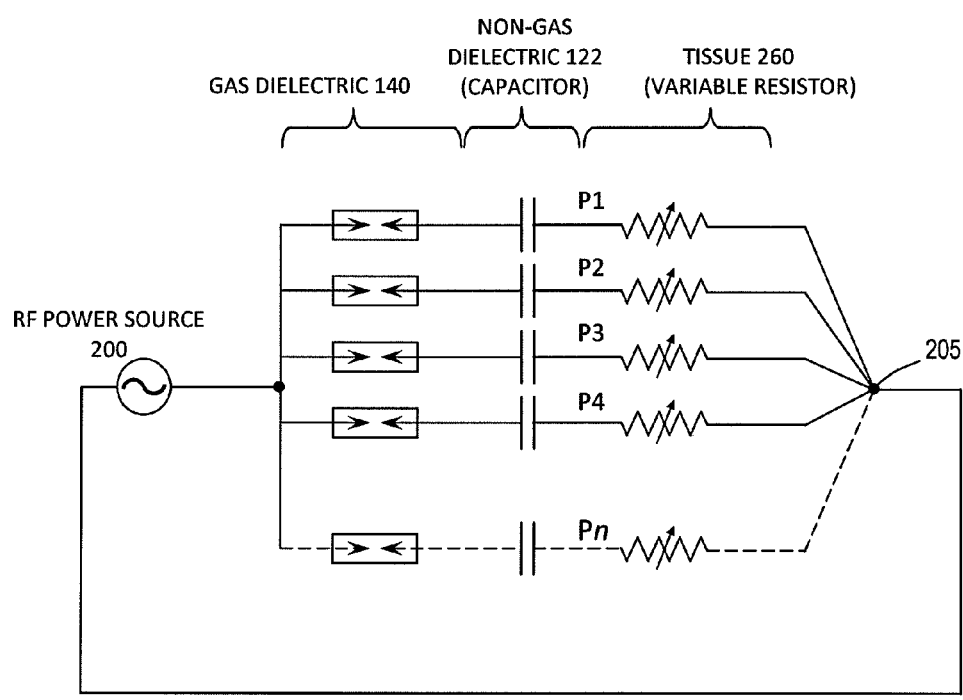
FIG. 10 is a circuit diagram showing the electrical aspects and components of the energy delivery modality.

In one aspect of the invention, FIG. 10 is a circuit diagram representing the steps of the method of FIGS. 9A-9D which explains the discovery that return electrode 205 can have a small surface area and not be subject to significant heating. In FIG. 10, it can be seen that voltage potential can increase until a dielectric breakdown occurs in both the neutral gas 140 and the dielectric structure 122 which cause a high voltage current through path P1 to electrode 205, followed by that path impeding out, thus causing the current to shift to current path P2, then current path P3 ad infinitum to current path indicated at Pn. The tissue 260 in FIG. 10 thus is shown as variable resistor in each current path as the current path is in continual flux based on the path increasing in resistance.

Figure 11A:
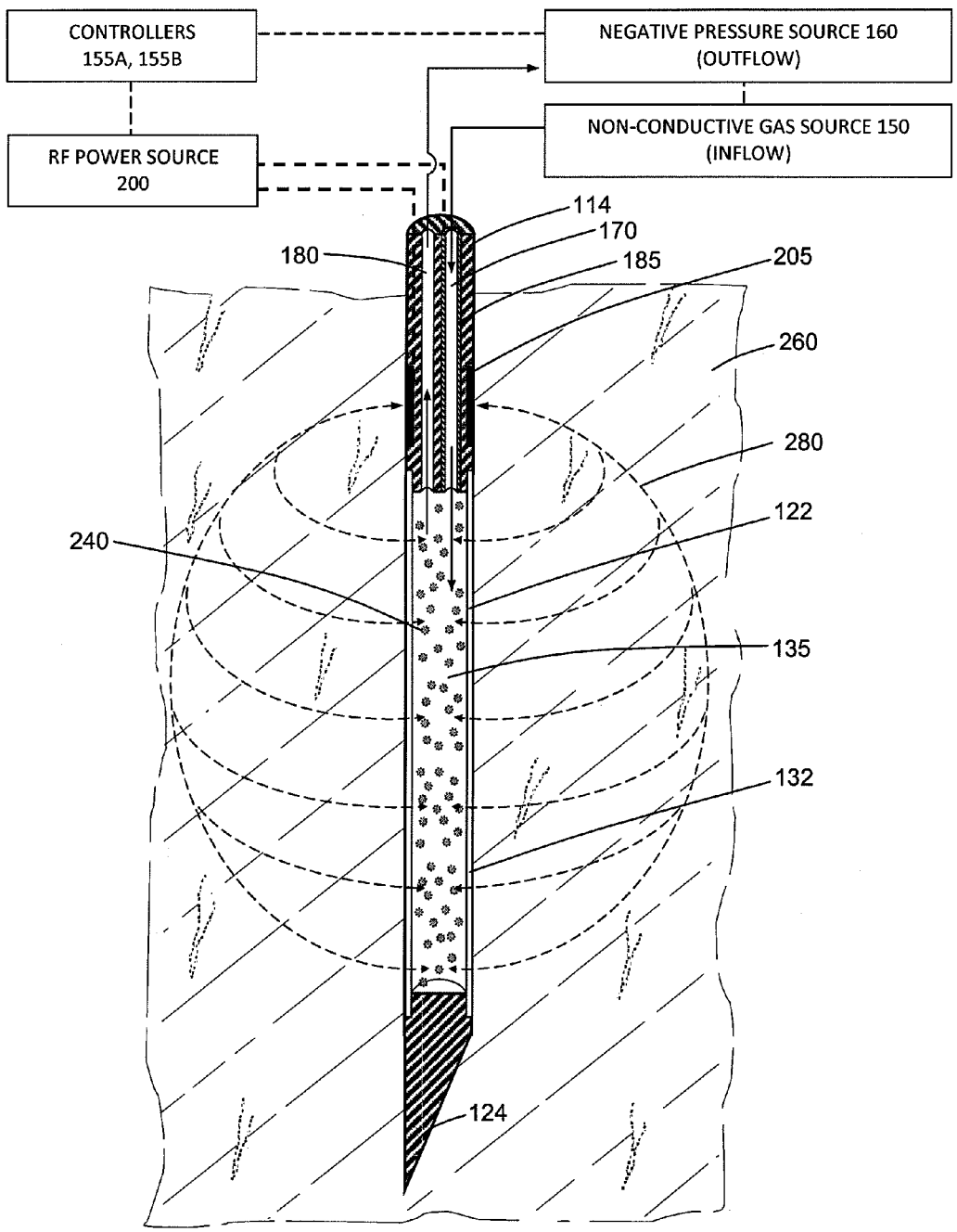
FIG. 11A is a sectional view of the working end of FIG. 3 positioned in tissue illustrating a step in a method of using the working end wherein current is coupled to tissue via an ionized gas and capacitive coupling through a thin wall dielectric structure.
Figure 11B:
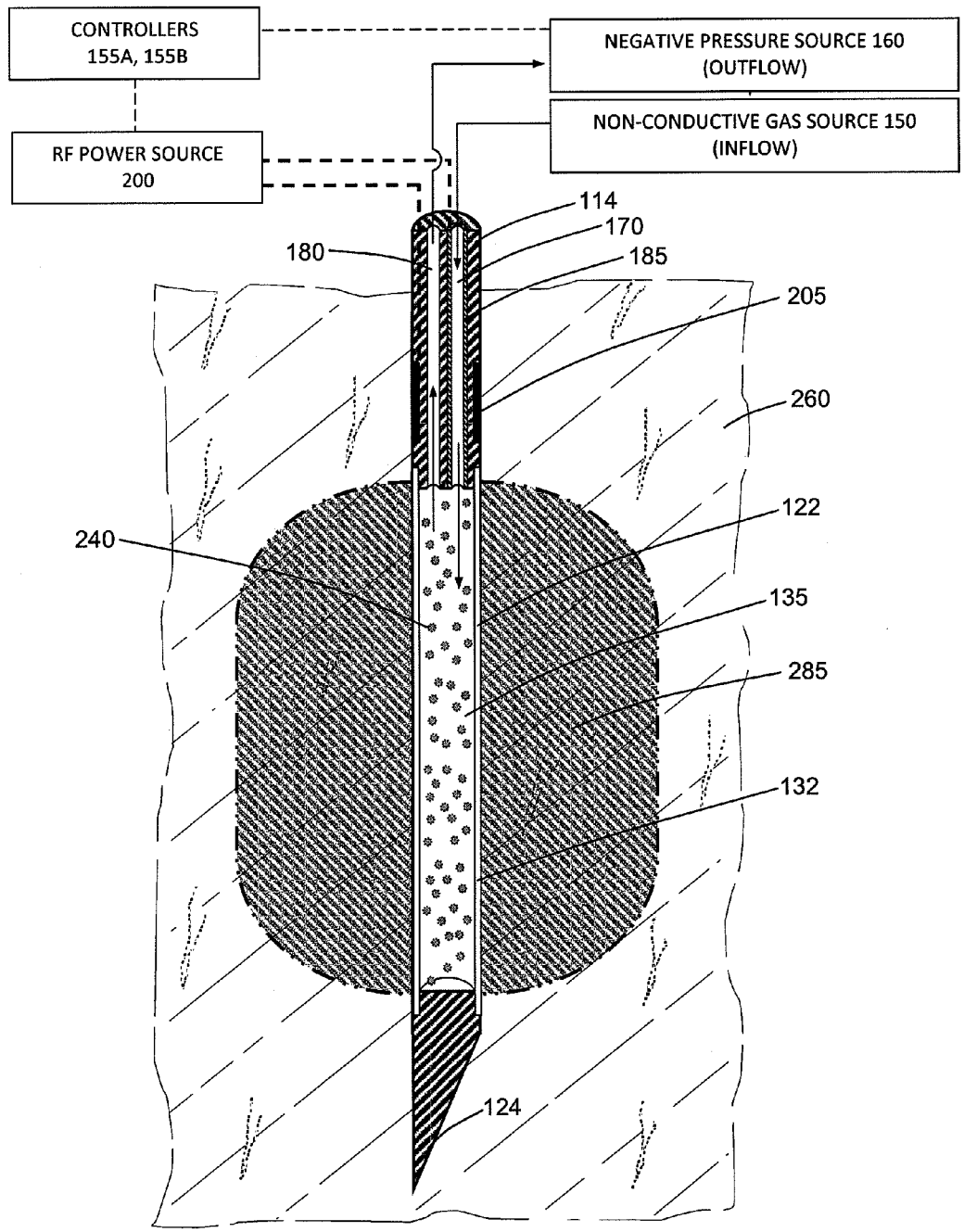
FIG. 11B is a sectional view similar to that of FIG. 11A illustrating another step in the method in which the ablated tissue volume is shown.

FIGS. 11A and 11B are enlarged schematic illustrations of the method of using the embodiment of FIG. 3 to capacitively couple current to tissue with a gas dielectric 140 in interior chamber 135 (i.e., plasma indicated at 240). Referring to FIG. 11A, the system is actuated, for example by a footswitch 208 (FIG. 1) coupled to RF power source 200 and controllers 155A and 155B which initiates a gas flow from source 150 to provide circulating flow through the first (inflow) channel 170, interior chamber 135 and the second (outflow) channel 180. For convenience, the embodiments utilizing such a circulating gas flow will be described herein as using one preferred gas, which is argon. In one embodiment, the gas flow rate can be in the range of 1 ml/sec to 50 ml/sec, more typically from 5 ml/sec to 30 ml/sec. In FIG. 11A, the working end 120 of the probe is introduced into tissue 260, for example to ablate a tumor as in FIGS. 2A-2B. The dielectric structure 122 is positioned in a desired location to ablate tissue adjacent thereto. The actuation of the system contemporaneously applies RF energy to electrode 185 and the gas flow which instantly converts the non-conductive argon 140 to a plasma indicated at 240 in FIG. 11A. The threshold voltage at which the argon becomes conductive (i.e., converted in part into a plasma) is dependent upon a number of factors controlled by the controller, including the pressure of the argon gas, the volume of interior chamber 135, the flow rate of the gas 140, the distance between electrode 185 and interior surfaces of the dielectric surface 122, the dielectric constant of the dielectric structure 122 and the selected voltage applied by the RF power source 200. It should be appreciated that the actuation of the system can cause gas flows for an interval of 0.1 to 5 seconds before the RF generator powers on to insure circulatory gas flows.

FIG. 11A schematically depicts current indicated at 280 being capacitively coupled through the wall 132 of the dielectric structure 122 to tissue 260, with the electric field lines indicating that high energy densities do not occur about electrode 205. Rather, as described above, the high resistance developed in tissue about the current path dielectric structure 122 causes rapidly changing current paths and ohmic heating. In one aspect of the invention, the capacitive coupling allows for rapid, uniform ablation of tissue adjacent the dielectric structure. FIG. 11B schematically depicts the tissue after the RF energy delivery is terminated resulting in the ablated tissue indicated at 285.

Figure 12:
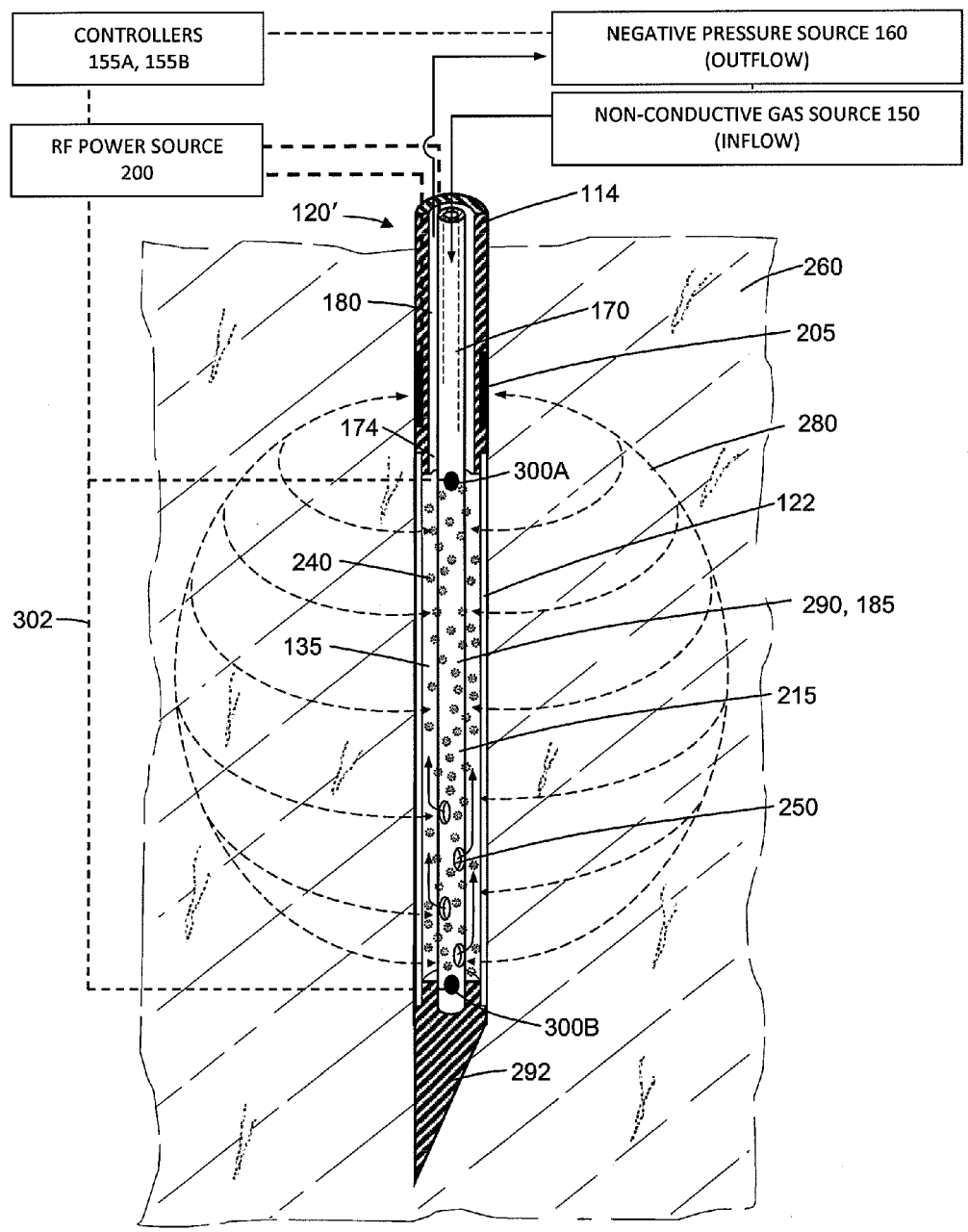
FIG. 12 is a sectional view of an alternate working end similar to that of FIG. 3 in a method of use, the dielectric structure having a central support member functioning as (i) an electrode and as (ii) a gas flow directing means.

Now turning to FIG. 12, an alternate working end 120' is shown in a method of use. In this embodiment, the dielectric structure 122 is similar to that of FIG. 3 except the working end 120' includes a central support member 290 that extends from extension member 214 to a distal tip portion 292. In this embodiment, the central support member 290 can comprise, or carry, a conductive electrode surface indicated at 295 to delivery energy to the gas 140 in interior chamber 135 for creating the plasma. The embodiment of FIG. 12 also includes concentric gas inflow and outflow channels, 170 and 180, wherein the first (inflow) channel 170 comprises a lumen in support member 290 that communicates with a plurality of flow outlets 250 in a distal portion of interior chamber 135. The gas outflow port 174 is again disposed in a proximal portion of interior chamber 135. The placement of gas inflow and outflow ports in opposing ends of interior chamber allows for effective gas circulation which assists in maintaining a predetermined plasma quality. In FIG. 12, the ablative currents and ohmic heating in tissue are indicated at 200.

In another aspect of the invention, FIG. 12 illustrates that at least one temperature sensor, for example thermocouples 300A and 300B, are provided within or adjacent to interior chamber 135 to monitor the temperature of the plasma. The temperature sensors are coupled to controllers 155A and 155B to thus allow feedback control of operating parameters, such a RF power delivered, neutral gas inflow rate, and negative pressure that assists outflow. By measuring the mass average temperature of the media in chamber 135, the degree of ionization of the ionized gas 240 can be determined. In one aspect of the invention, the measured temperature within chamber 135 during operation can provide feedback to gas circulation controller to thereby modulate the flow of neutral gas to maintain a degree of ionization between 0.01% and 5.0%. In another aspect of the invention, the measured temperature within chamber 135 during operation can provide feedback to modulate flow of neutral gas to maintain a temperature of less than 200° C., 180° C., 160° C., 140° C., 120° C., or 100° C. In several embodiments of polymeric dielectric structures, it is important to maintain a cold or technological plasma to prevent damage to the dielectric. In another aspect of invention, the system operating parameters can be modulated to maintain the mass average temperature within a selected range, for example a 5° C. range, a 10° C. range or a 20° C. range about a selected temperature for the duration of a tissue treatment interval. In another aspect of invention, the system operating parameters can be modulated to maintain a degree of ionization with less than 5% variability, less than 10% variability or less than 20% variability from a selected "degree of ionization" target value for a tissue treatment interval. While FIG. 12 shows thermocouples within interior chamber 135, another embodiment can position such temperature sensors at the exterior of the wall 132 of the dielectric structure to monitor the temperature of the wall. It also should be appreciated that multiple electrodes can be provided in the interior chamber to measure impedance of the gas media to provide an additional from of feedback signals.

In another embodiment similar to FIG. 12, the working end or flow channel in communication with the interior chamber 135 can carry at least one pressure sensor (not shown) and pressure measurement can provide feedback signals for modulating at least one operational parameter such as RF power delivered, neutral gas inflow rate, negative pressure that assists outflow, degree of ionization of the plasma, or temperature of the plasma. In another aspect of invention, the system operating parameters can be modulated to maintain a pressure within chamber 135 less than 5% variability, less than 10% variability or less than 20% variability from a selected target pressure over a tissue treatment interval.

In general, FIG. 13 represents the steps of a method corresponding to one aspect of the invention which comprises containing a non-conductive gas in an interior of an enclosure having a thin dielectric wall, engaging and external surface of the dielectric wall in contact with a target region of tissue, and applying a radiofrequency voltage across the gas and the dielectric wall wherein the voltage is sufficient to initiate a plasma in the gas and capacitively couple current in the gas plasma across the dielectric wall and into the engaged tissue. This method includes the use of a first polarity electrode in contact with the gas in the interior of the thin dielectric wall and a second polarity electrode in contact with the patient's tissue.

Figure 14:
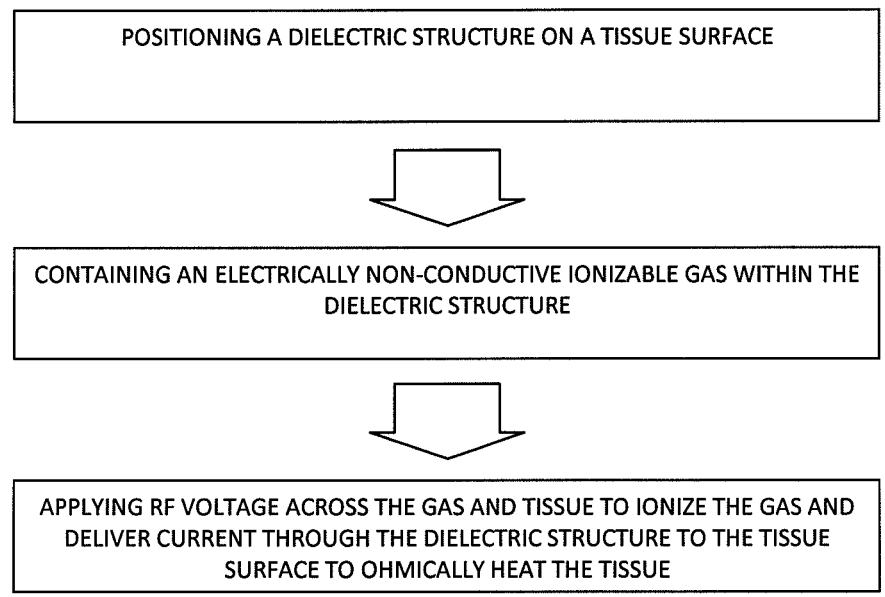
FIG. 14 is a block diagram of another method corresponding to the invention.

FIG. 14 represents aspects of a related method corresponding to the invention which comprises positioning a dielectric structure on a tissue surface, containing a non-conductive, ionizable gas within the dielectric structure, and applying RF voltage across the gas and tissue to ionize the gas and deliver current through the dielectric structure to the tissue to ohmically heat the tissue.

In general, FIG. 15 represents the steps of a method corresponding to another aspect of the invention which comprises providing an electrosurgical working end or applicator with a first gas dielectric and a second non-gas dielectric in a series circuit, engaging the non-gas dielectric with tissue, and applying sufficient RF voltage across the circuit to cause dielectric breakdown in the gas dielectric to thereby apply ablative energy to the tissue. The step of applying ablative energy includes capacitively coupling RF current to the tissue through the second non-gas dielectric media.

FIG. 16 represents steps of another aspect of the invention which comprises positioning a dielectric structure enclosing an interior chamber in contact with targeted tissue, providing a gas media in the interior chamber having a degree of ionization of at least 0.01%, and applying RF current through the gas media to cause capacitive coupling of energy through the dielectric structure to modify the tissue. In this aspect of the invention, it should be appreciated that an ionized gas can be provided for inflow into chamber 135, for example with a neutral gas converted to the ionized gas media prior to its flow into chamber 135. The gas can be ionized in any portion of a gas inflow channel intermediate the gas source 150 and the interior chamber 135 by an RF power source, a photonic energy source or any other suitable electromagnetic energy source.

Figure 17:
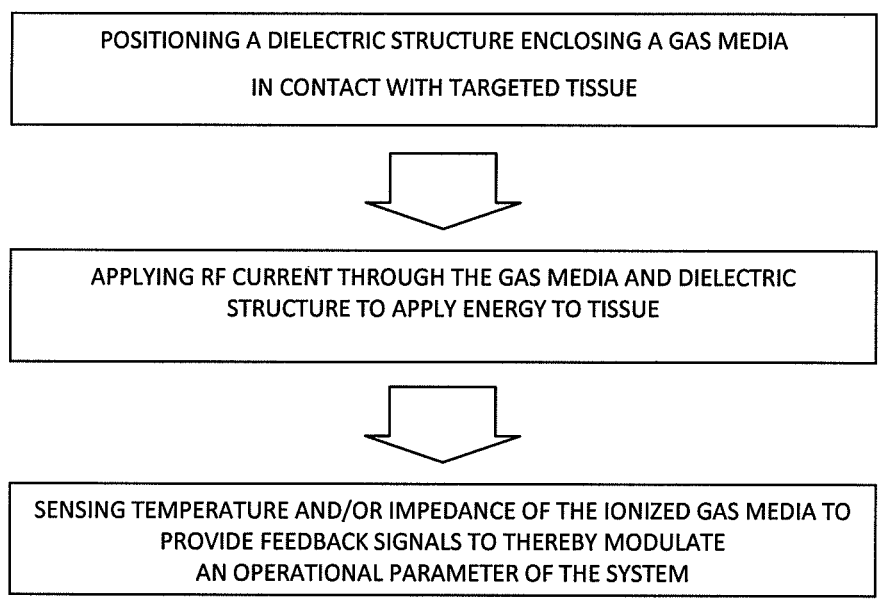
FIG. 17 is a block diagram of another method corresponding to the invention.
Figures 18A, 18B:
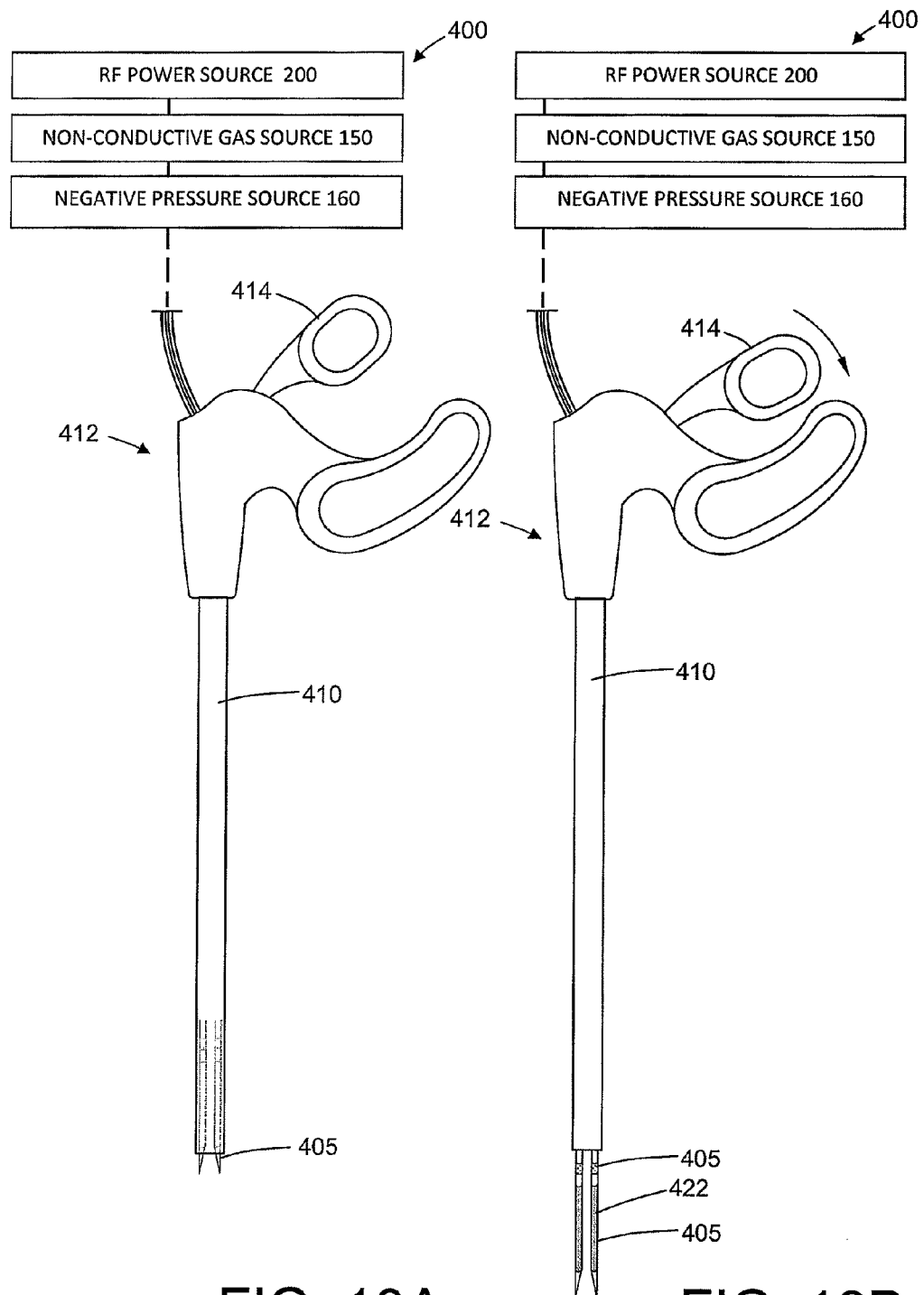
FIG. 18A is plan view of an alternate ablation probe that carries a plurality of extendable needle-like ablation elements from a sheath, each element having a dielectric structure with varied dielectric parameters for directional control of capacitive coupling and thus directional control of ablation.
FIG. 18B is another view of the ablation probe of FIG. 18A with the plurality of extendable needle ablation elements extended from the sheath.

FIG. 17 represents the steps of another method of the invention which comprises positioning a dielectric structure enclosing a gas media in contact with targeted tissue, and applying RF current through the gas media and dielectric structure to apply energy to tissue, and sensing temperature and/or impedance of the ionized gas media to provide feedback signals to thereby modulate a system operational parameter, such as RF power delivered, neutral gas inflow rate, and/or negative pressure that assists gas outflows.

Figure 19:
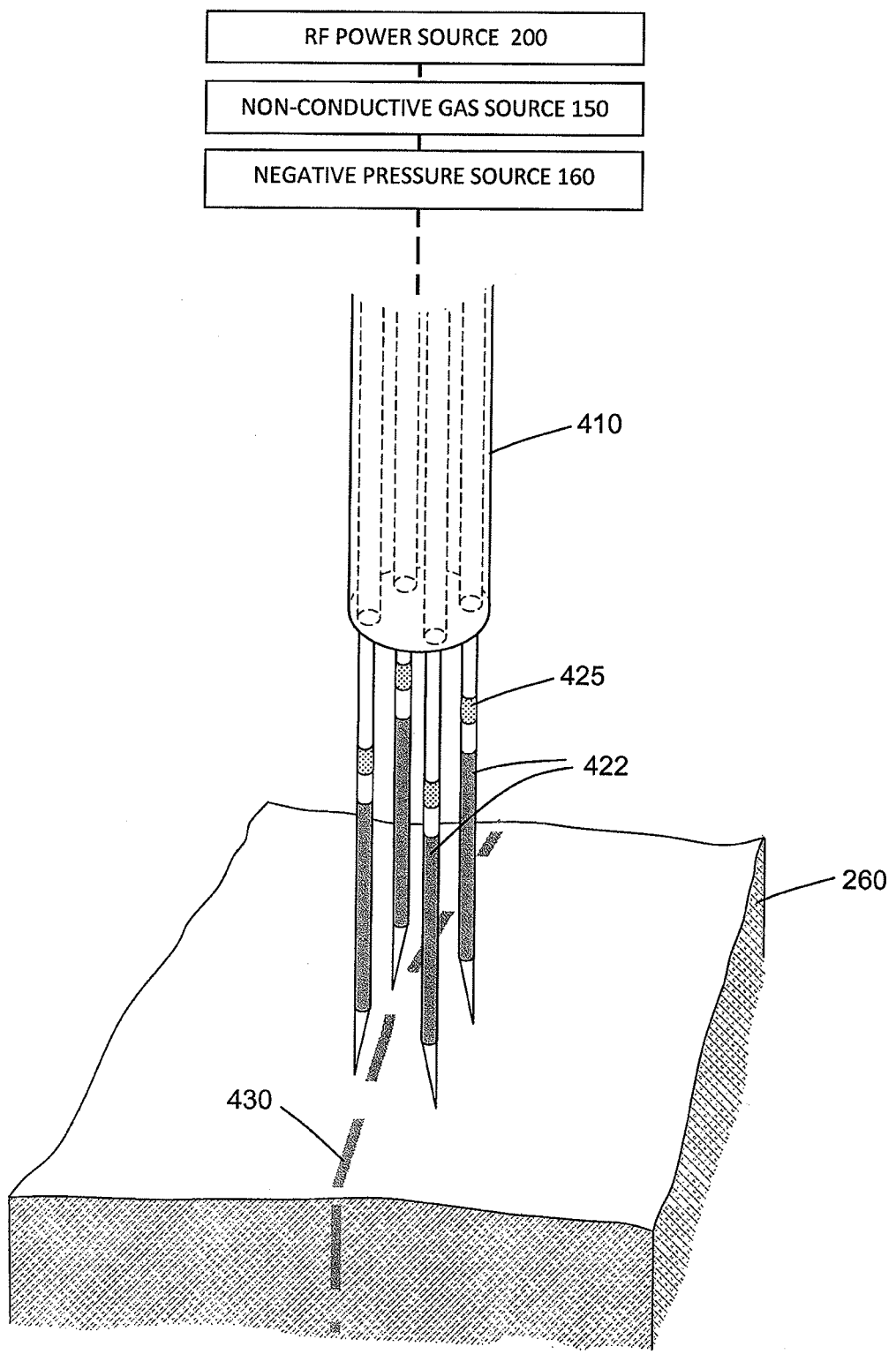
FIG. 19 is an enlarged view of a working end of the ablation probe of FIGS. 18A-18B with a tissue volume targeted for ablation and resection.
Figure 20:
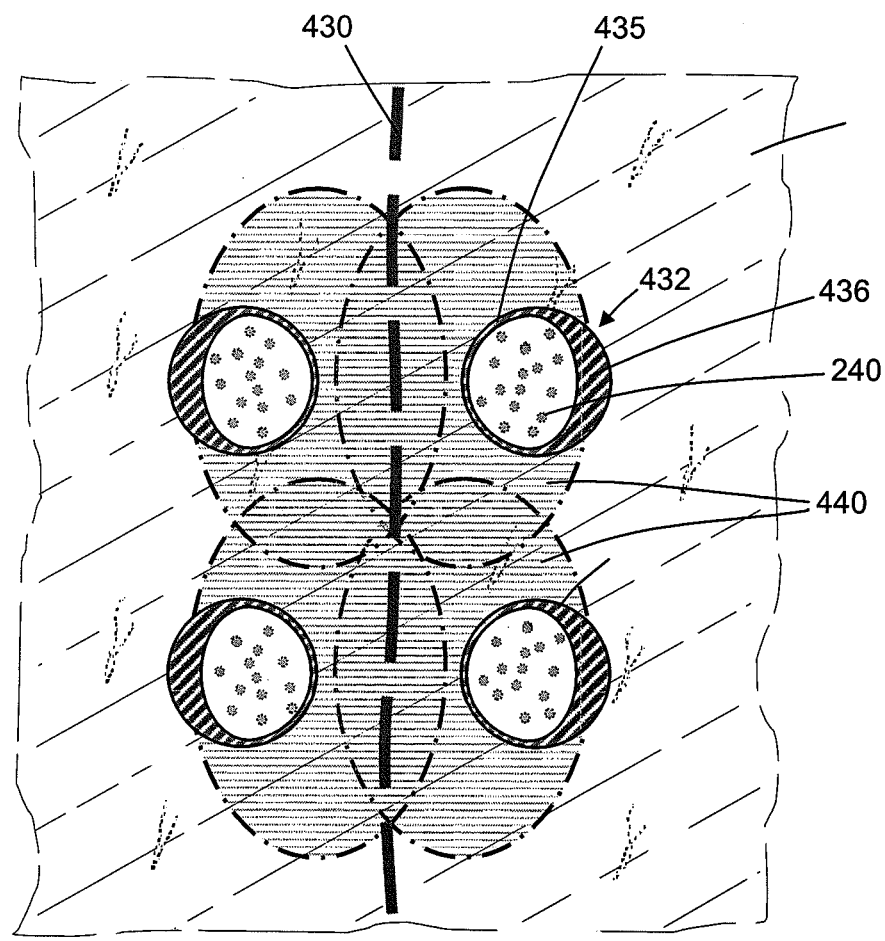
FIG. 20 is a sectional view of ablated tissue using the working end of FIG. 19 showing the directed capacitive coupling and directed ablation.

Now turning to FIGS. 18A-22, other embodiments of electrosurgical working ends are shown that adapted to apply energy to tissue as described above, except that the dielectric structures have differing dielectric portions each having a different relative permittivity to thus cause differential effects (greater or lesser capacitive coupling) in tissue regions in contact with the different portions of the dielectric structure. In one probe embodiment 400 shown in FIGS. 18A-18B, a working end carries multiple tissue-penetrating elements 405 that are similar to the needle-like working end 120 of FIGS. 1-3. The tissue-penetrating elements 405 can be extendable from a shaft 410 of an endoscopic instrument 412 by actuation of lever 414. Each tissue-penetrating elements 405 has a working end with a dielectric structure 422 as described above and one or more return electrodes indicated at 425. As can be seen in FIG. 19, the tissue-penetrating elements 405 are adapted for penetrating tissue 260, such as a liver, on either side of a target line 430 that is to be a resection line or plane. Thus, the tissue-penetrating elements 405 can coagulate tissue on either side of line 430, and thereafter the tissue can be cut and bleeding will be prevented or reduced. Such an instrument 412 can be used in liver resections, lung resections and the like. FIG. 20 illustrates a cross-section of the multiple tissue-penetrating elements 405 of FIG. 19 in tissue wherein it can be seen that the wall 432 of the dielectric structure varies from a thin-wall portion 435 to a thicker wall portion 436 with each portion extending axially along the length of the dielectric structure. As can easily be understood, the thin-wall portion 435 allows a greater coupling of current to adjacent tissue 260 when compared to the thicker wall portion 436. For this reason, the depth of ablated or cauterized tissue regions 440 will vary depending on whether it is adjacent to thin-wall portion 435 or the thicker wall portion 436. Thus, the instrument can control the depth of ablation by varying the volume resistivity of the dielectric wall. For example, the thin-wall portion 435 can have a volume resistivity in the range of $1 \times 10^{14}$ Ohm/cm as described above which can then transition to thicker wall portion 438 having a volume resistivity of 1.5×, 2× or 3× triple the $1 \times 10^{14}$ Ohm/cm range. As depicted in FIG. 20, the energy delivery converges to ablate or cauterize tissue regions 440 inwardly toward line 430 that is targeted for cutting. Outwardly from line 430 there is less collateral damage due to reduced ohmic heating.

Figure 21:
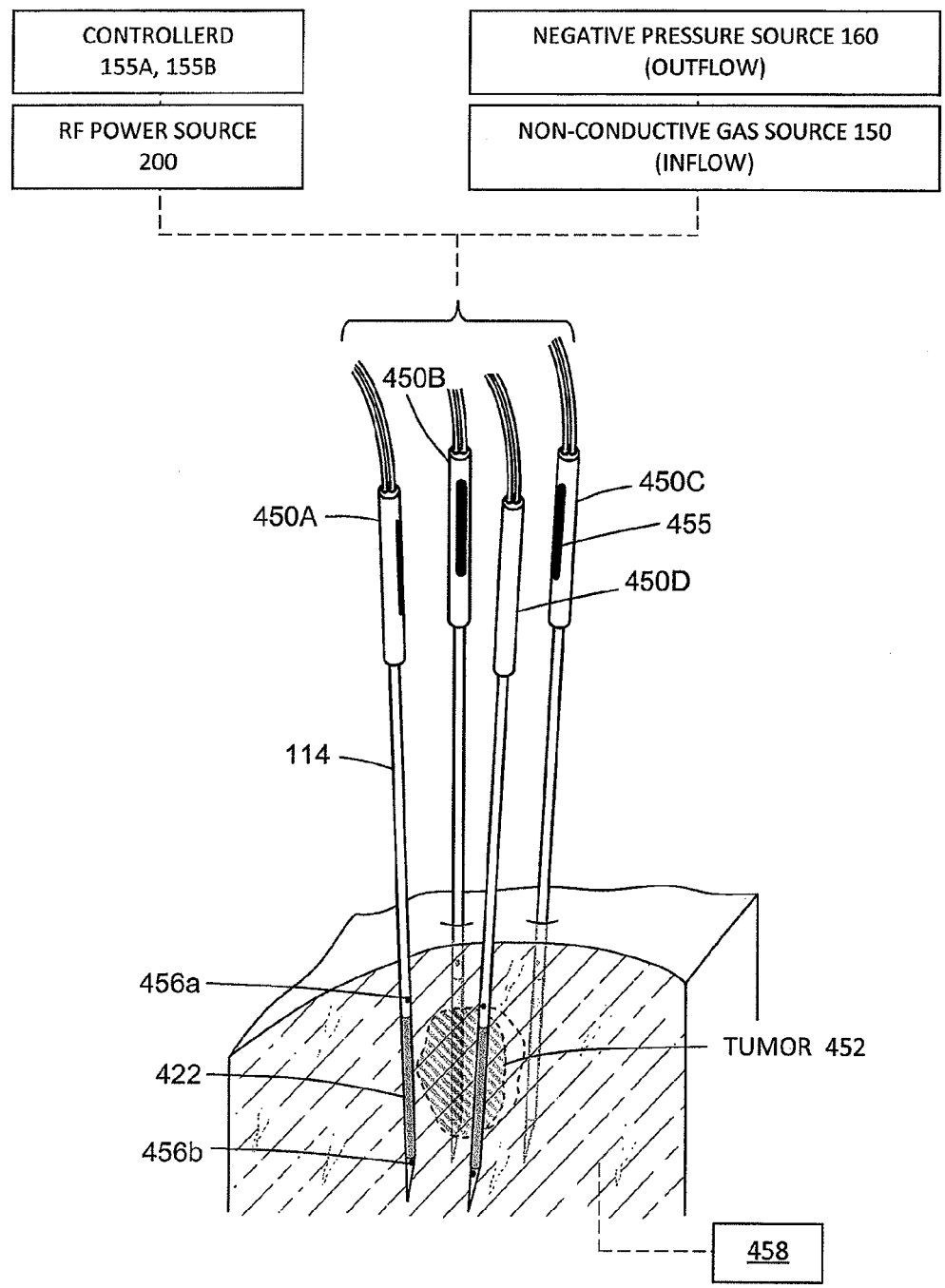
FIG. 21 is a schematic view of a tumor ablation method using a plurality of working ends similar to that of FIGS. 19-20 for directed capacitive coupling and directed ablation.

FIG. 21 illustrate a plurality of probes 450A-450D that demonstrate a similar use of "directional" dielectric structures 422 for directional control of energy delivery to tissue, in this case to provide converging regions of ablation to ablate tumor 452 as in the working ends of the device of FIG. 18A-20. In this embodiment, it can be seen that the probe handles include an indicator mark 455 that indicates the orientation of the thin-wall portion 435 or thick wall portion 436 to thus selectively direct RF energy delivery. In another embodiment, it should be appreciated that the proximal and distal ends of a dielectric structure 422 can be marked with any suitable imageable marker, for example radiopaque markings. In another aspect of the invention shown in FIG. 20, any probe can carry at least one thermocouple, for example thermocouples 456a and 456b, at locations proximal and distal to the dielectric structure 422 to measure tissue temperatures to provide an endpoint for terminating the delivery of energy. The thermocouples provide signal to controllers 155A and 155B to terminate the ablation procedure. The ablation probes 450A-450D can each carry a return electrode as in the working end of FIG. 19, or alternatively there can be a remote return electrode as indicated at 458 in FIG. 21.

Figure 22:
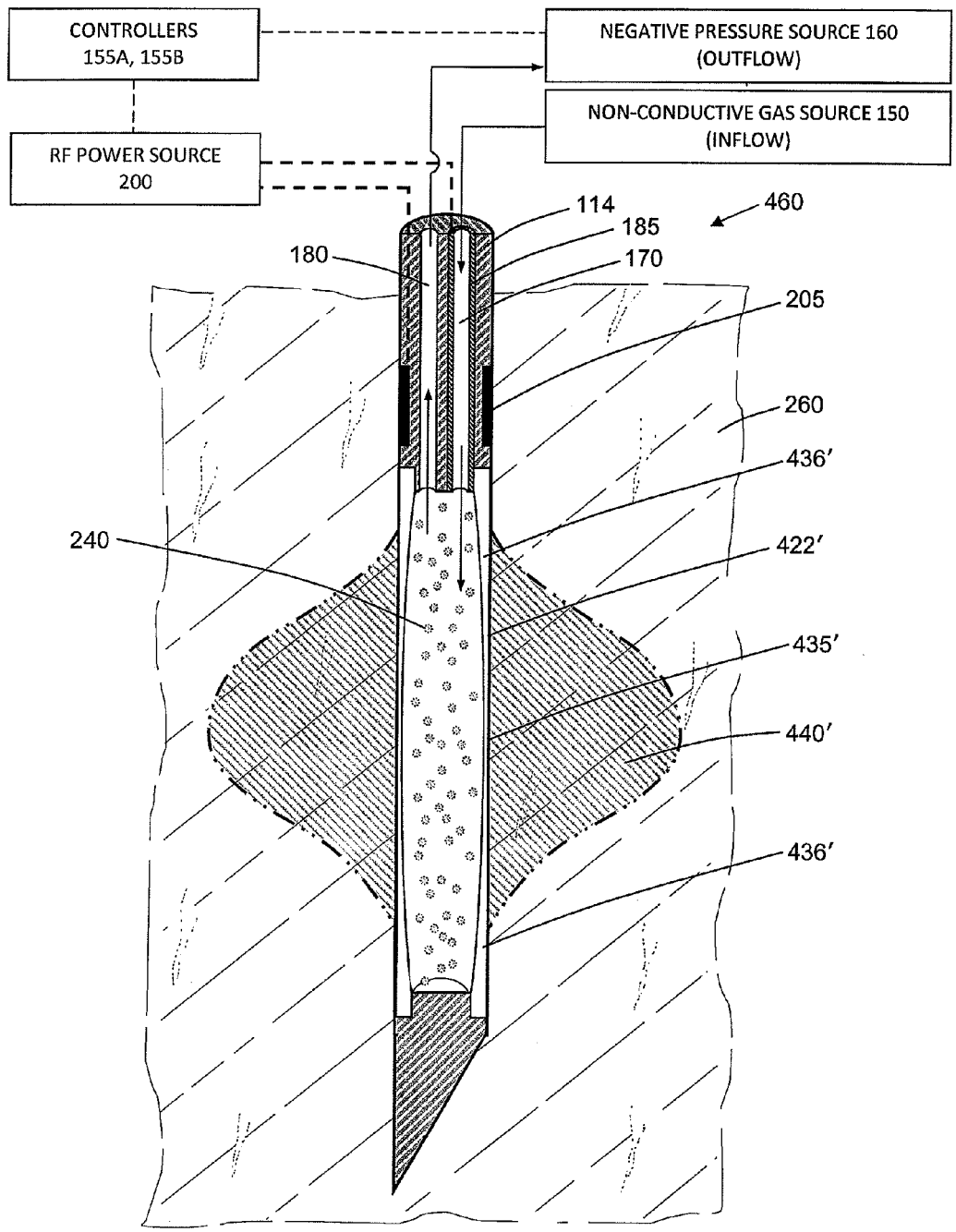
FIG. 22 is a sectional view of an alternate working end similar to that of FIGS. 3 and 12 with a non-uniform thickness dielectric structure for directional control of capacitive coupling and thus directional control of ablation.

FIG. 22 illustrates another embodiment of electrosurgical working end 460 wherein wall 432 of the dielectric structure 422' varies from thin-wall portion 435' to a proximal and distal thicker wall portions 436' with each portion extending radially about the dielectric structure. As can easily be understood as shown in FIG. 22, the central thin-wall portion 435' thus allows a greater coupling of current to adjacent tissue 260 to cause a deeper ablated tissue 440' as compared to the thicker wall portions 436' at the ends of the dielectric structure (cf. ablated tissue in FIG. 11B). In all other respects, the working end 460 operates as previously described embodiments.

Figures 23, 24:
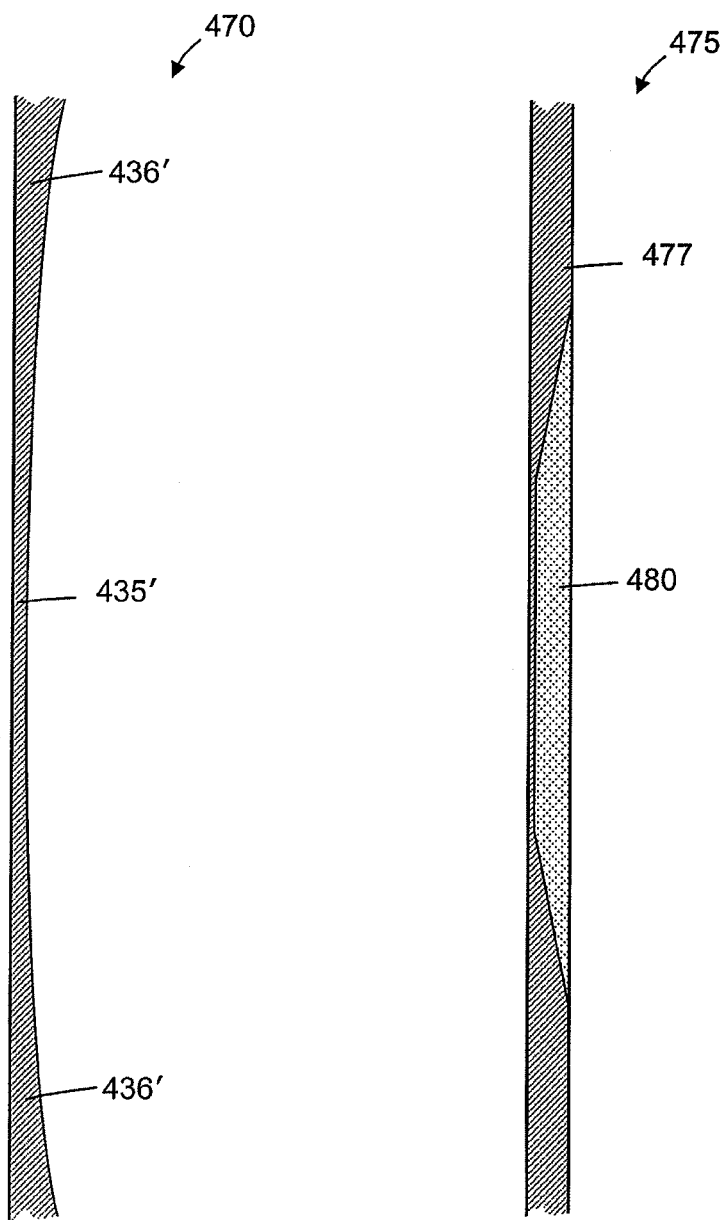
FIG. 23 is a sectional view of a non-uniform thickness dielectric structure for directional control of capacitive coupling to tissue.
FIG. 24 is a sectional view of a uniform thickness dielectric structure with different materials for directional control of capacitive coupling to tissue.

In the electrosurgical ablation working ends of FIGS. 19-21 above, the dielectric structures 422 and 422' provide differential or energy transmissibility by means of varying the thickness of a dielectric such as silicone. A portion of an exemplary dielectric wall 470 with varying thickness portions 435' and 436' is shown in FIG. 23 which represents the dielectric of FIG. 22. In other words, a varied thickness wall with a uniform dielectric constant or volume resistivity of the material can provide varied coupling of RF current to tissue about the surface of the dielectric. It should be appreciated that an objective of the invention is controlled depth of ablation which can be accomplished equally well by having a uniform thickness dielectric but varying the electrical properties of the material. FIG. 24 illustrates a constant thickness dielectric wall 475 with first and second dielectric materials 477 and 480 that provides for higher capacitive coupling through material 480. The number of layers of materials, or material portions, and their dielectric properties can range from two to ten or more. Further, combinations of varying material thickness and dielectric properties can be utilized to control capacitive coupling of current through the dielectric.

Figure 25A:
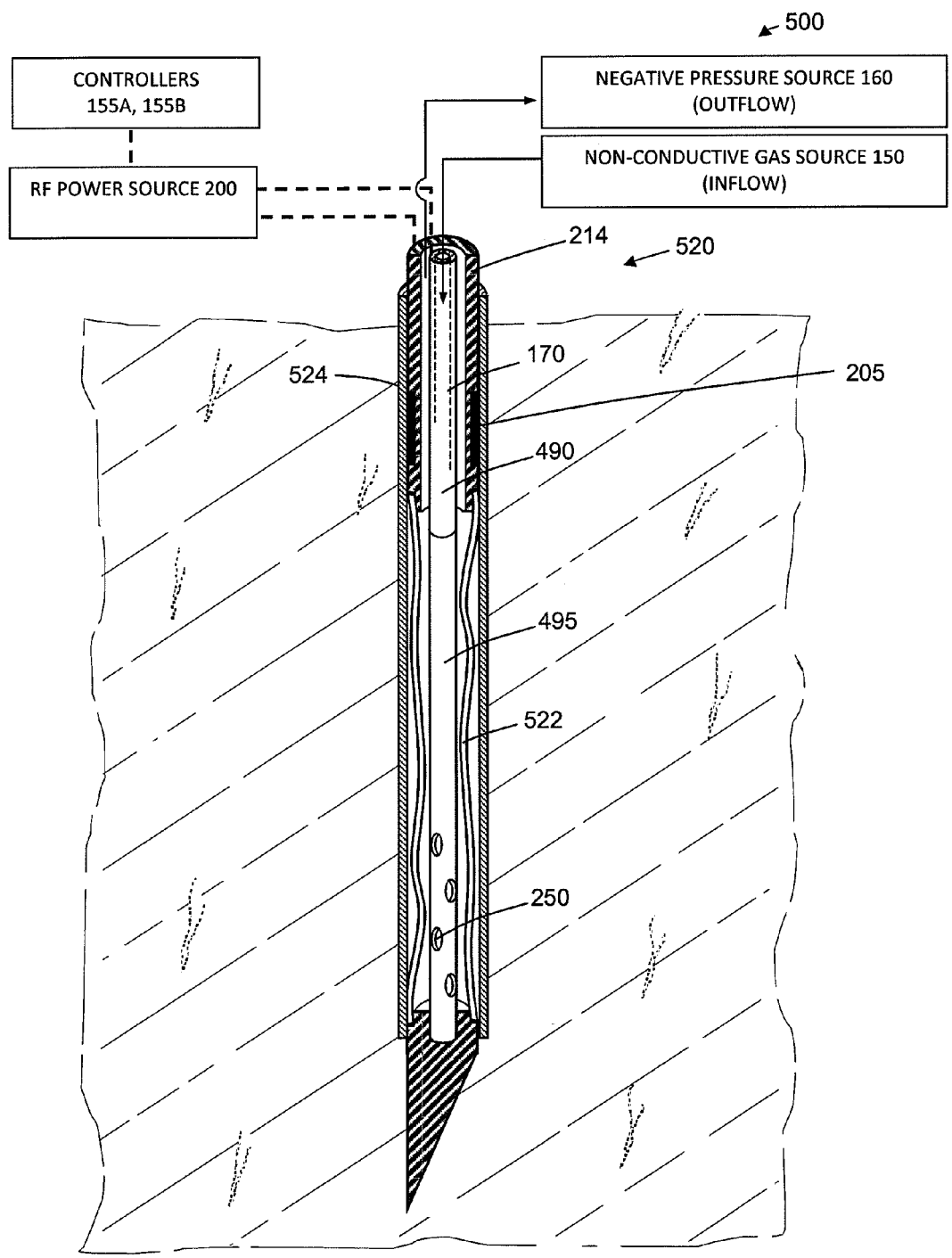
FIG. 25A is a sectional view of a working end of an ablation probe similar to that of FIG. 12 with an expandable thin-wall dielectric structure in a non-extended condition.

FIGS. 25A-25D illustrate another embodiment of electrosurgical system 500 and working end 520 and method of use that is similar to the device of FIG. 12 except that the dielectric structure 522 of FIGS. 25A-25D is fabricated of a thin-wall dielectric that can be moved from a first non-expanded condition to an expanded condition. In FIG. 25A, the working end is shown with a distally-extended sheath 524 that can be of plastic or metal. A first step of a method thus comprises introducing the working end into tissue interstitially or into a body lumen with the sheath protecting the dielectric structure 522. The dielectric structure 522 is then expanded by gas inflows which causes compression of surrounding tissue and increases the surface area of the thin dielectric wall in contact with tissue. As can be seen in FIG. 25A, the expandable dielectric 522 can be fabricated of a distensible or non-distensible material, such as a stretchable silicone or a braided, reinforced non-stretch silicone. The wall thickness of a silicone structure can range from 0.004" to 0.030", and more typically from 0.008" to 0.015" with an interior volume ranging from less that 5 ml to more than 100 ml. The dielectric structure can have any suitable shape such as cylindrical, axially tapered, or flattened with interior baffles or constraints. FIG. 26 depicts a cross-section of the sheath 524 and a non-distensible expandable dielectric 522 with a method of folding the thin dielectric wall.

Figure 25B:
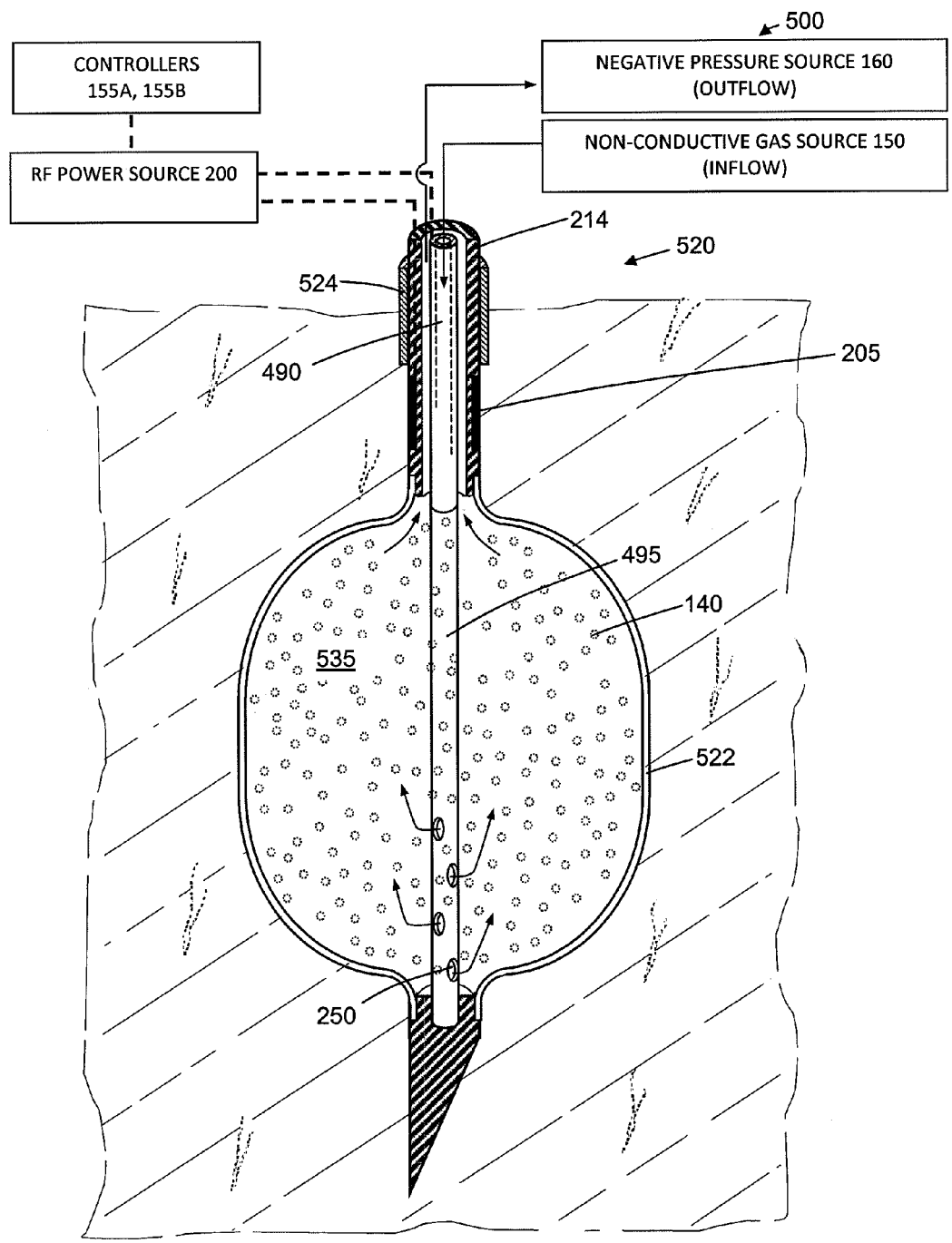
FIG. 25B is a sectional view of the working end of FIG. 25A with the expandable thin-wall dielectric structure in an extended condition in soft tissue, the structure configure for expansion by gas inflation pressure.
Figure 26:
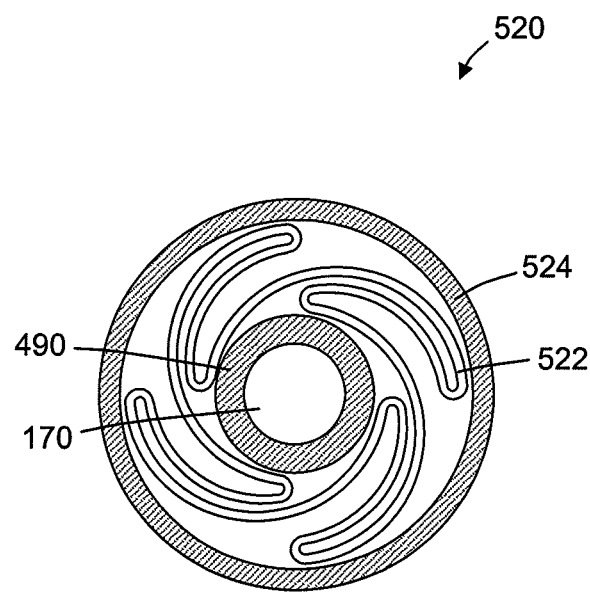
FIG. 26 is another cross-sectional view of the expandable dielectric structure in a non-extended condition folded within a translatable sheath.

FIG. 25B illustrates multiple subsequent steps of the method wherein sheath 524 is retracted and the physician actuates the gas source 150 and controller to expand the expandable dielectric structure 522. The structure 522 or balloon can be expanded to any predetermined dimension or pressure in soft tissue or in any body lumen, cavity, space or passageway. Radiopaque marks on the dielectric structure (not shown) can be viewed fluoroscopically to determine its expanded dimension and location. The gas circulation controller 155A can circulate gas flow after a predetermined pressure is achieved and maintained.

Figure 25C:
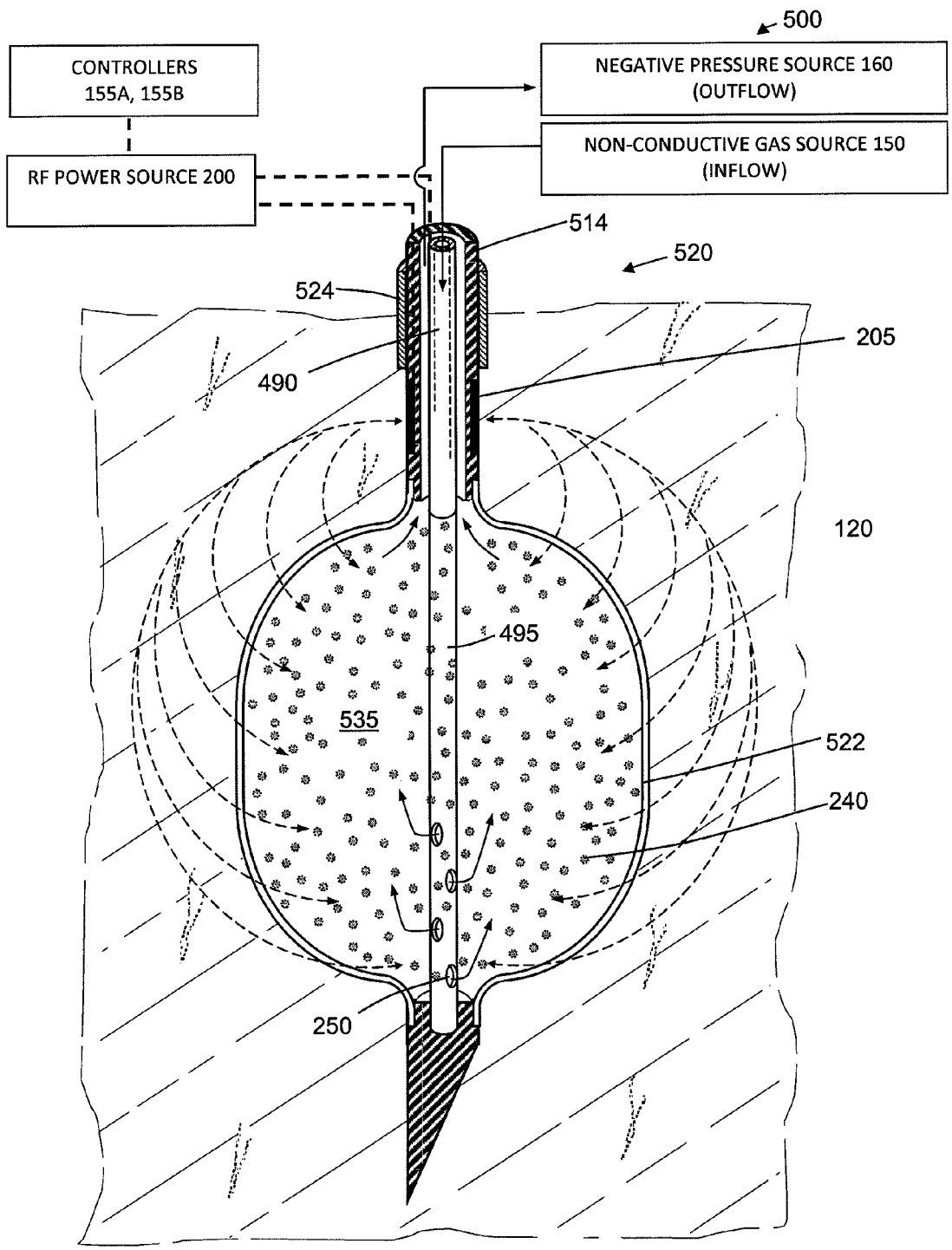
FIG. 25C is another sectional view as in FIG. 25B showing the capacitive coupling of energy to the tissue from a contained plasma in the expandable dielectric structure.
Figure 25D:
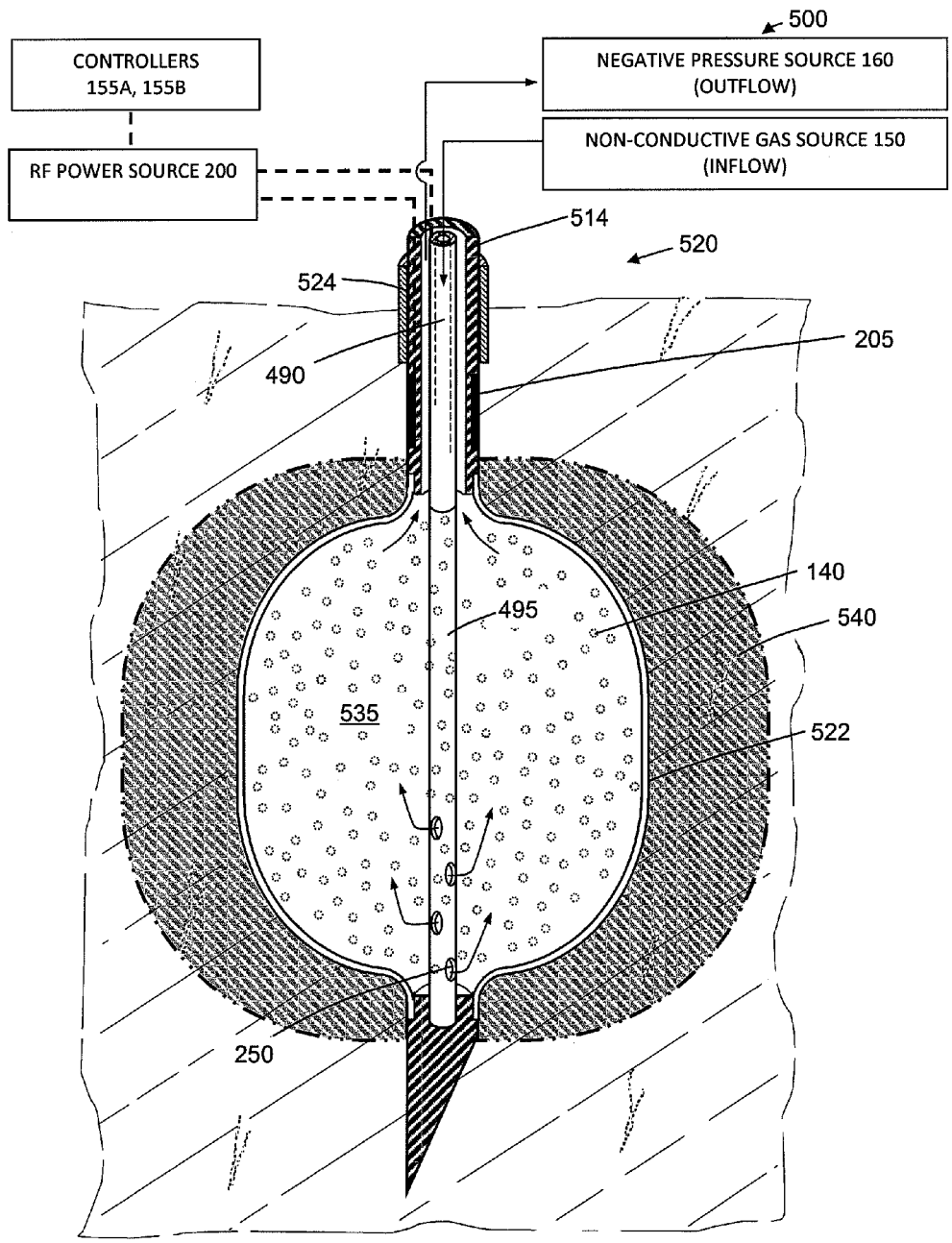
FIG. 25D is another sectional view as in FIG. 25B showing the region of ablated tissue after energy delivery.

FIG. 25C depicts a subsequent step of the method in which the physician actuates the RF power source 200 and controller 155B to develop high voltage potential between central support electrode 295 and return electrode 205 which, as described previously, can cause a voltage breakdown in the gas dielectric 140 (FIG. 25B) to create plasma 240 and contemporaneously capacitively couple current to tissue 260 as indicated by current flows 530. FIG. 25D depicts the termination of RF energy delivery so that the voltage breakdown and resulting plasma is extinguished—leaving uniform ablated tissue 540 similar to that shown in FIG. 11B.

In one embodiment, the dielectric structure 522 was made from NuSil MED-6640 silicone material commercially available from NuSil Technology LLC, 1050 Cindy Lane, Carpinteria, Calif. 93013. The dielectric structure 522 was fabricated by dipping to provide a length of 6 cm and a uniform wall thickness of 0.008" thereby providing a relative permittivity in the range of 3 to 4. The structure ends were bonded to a shaft having a diameter of approximately 4 mm with the expanded structure having an internal volume of 4.0 cc's. The gas used was argon, supplied in a pressurized cartridge available from Leland Limited, Inc., Post Office Box 466, South Plainfield, N.J. 07080. The argon was circulated at a flow rate ranging between 10 ml/sec and 30 ml/sec. Pressure in the dielectric structure was maintained between 14 psia and 15 psia with zero or negative differential pressure between gas inflow source 150 and negative pressure (outflow) source 160. The RF power source 200 had a frequency of 480 KHz, and electrical power was provided within the range of 600 Vrms to about 1200 Vrms and about 0.2 Amps to 0.4 Amps and an effective power of 40 W to 80 W.

Figure 27:
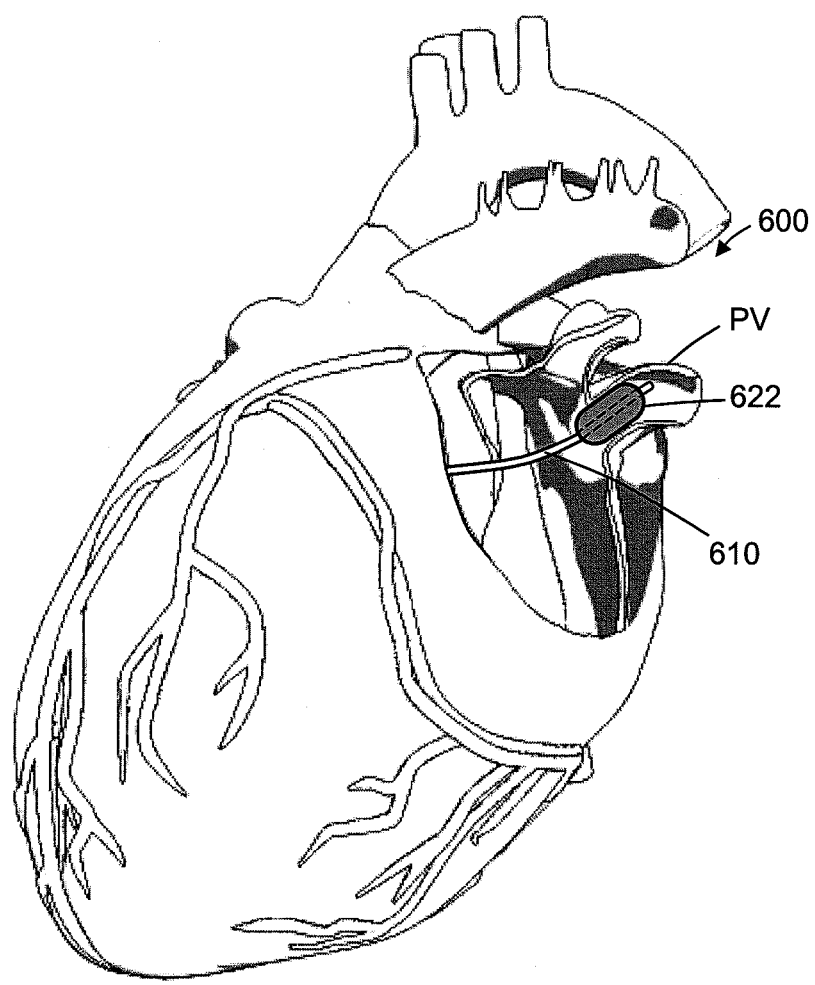
FIG. 27 is a cut-away schematic view of a heart and a working end of another ablation probe similar to that of FIG. 25A with an expandable thin-wall dielectric structure configured for ablating about a pulmonary vein to treat atrial fibrillation, with the structure configure for expansion by gas inflation pressure.
Figure 28:
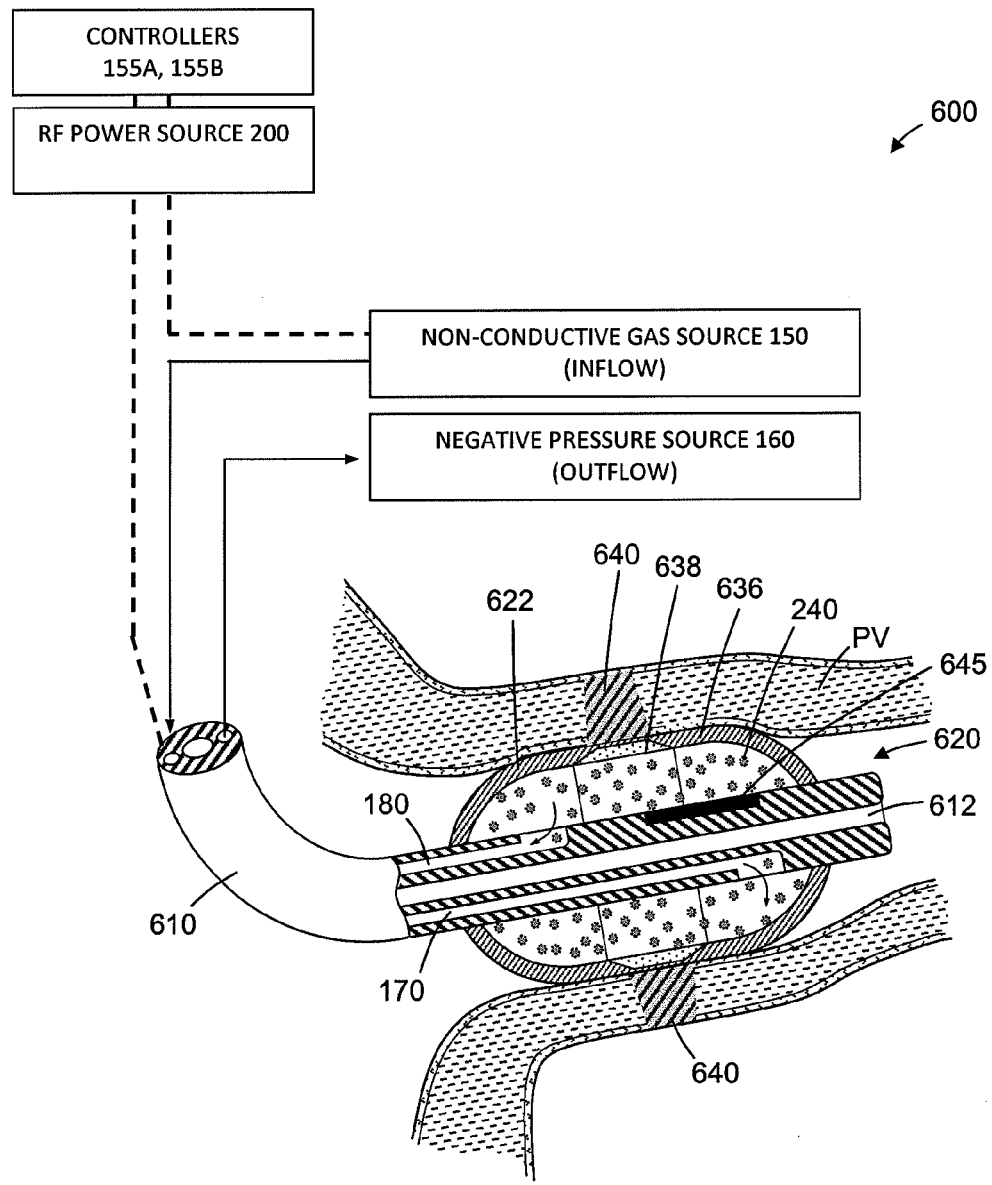
FIG. 28 is an enlarged sectional schematic view of the working end of FIG. 27 ablating a pulmonary vein.

FIGS. 27 and 28 illustrate another embodiment of electrosurgical system 600 that comprises a catheter having working end 610 for treating atrial fibrillation by means of ablation about pulmonary veins PV. Various methods of using conventional RF catheters for such treatments are known. Catheter 610 is configured with a guidewire channel 612 and can be navigated to a site shown in FIGS. 27-28. The catheter working end 620 included an expandable dielectric structure 622 similar to that of FIGS. 25A-25D that can be expanded to apply pressure between the balloon wall and the tissue to thereafter create a circumferential lesion in a pulmonary vein PV. FIG. 28 is a schematic illustration that again shows gas source 150 and gas circulation controller 155A that can expand chamber 635 in the thin-wall dielectric structure 622 to engage the wall of the pulmonary vein PV. In the embodiment of FIG. 28, it can be seen that the wall of dielectric 622 includes a first (lesser) energy-transmissible region 636 and a second (greater) energy-transmissible region 638 thus allowing a focused circumferential ablation wherein the dielectric has a lesser cross-section as disclosed in co-pending U.S. patent application Ser. No. 12/541,043 filed on Aug. 13, 2009. Thereafter, the RF power source 200 and controller 155B can be actuated to convert the neutral gas flow to plasma 240 and contemporaneously ablate tissue indicated at 640. In this embodiment, a first polarity electrode 645 is provided on the catheter shaft in chamber 635 that can cooperate with a second polarity electrode on the catheter shaft remote from balloon 622 or any other type of ground pad may be used (not shown). In all other respects, the method of the invention for ablation of cardiac tissue follows the steps described above. The balloon can have radiopaque markings, and the system can be operated by an algorithm to expand the dielectric structure 622 or balloon to a pre-determined pressure, then delivery RF energy and terminate delivery automatically. It should be appreciated that additional electrodes can be provided in the balloon surface (not shown) for mapping conduction in the cardiac tissue.

While FIG. 27-28 illustrate an expandable dielectric 622 for treating cardiac tissue, it should be appreciate that the scope of the invention includes using a similar apparatus and method to controllably apply ablative RF energy to any body lumen, vessel, body cavity or space such as in a stomach, gall bladder, esophagus, intestine, joint capsule, airway, sinus, a blood vessel, an arteriovascular malformation, heart, lung, uterus, vaginal canal, bladder or urethra.

Figure 29:
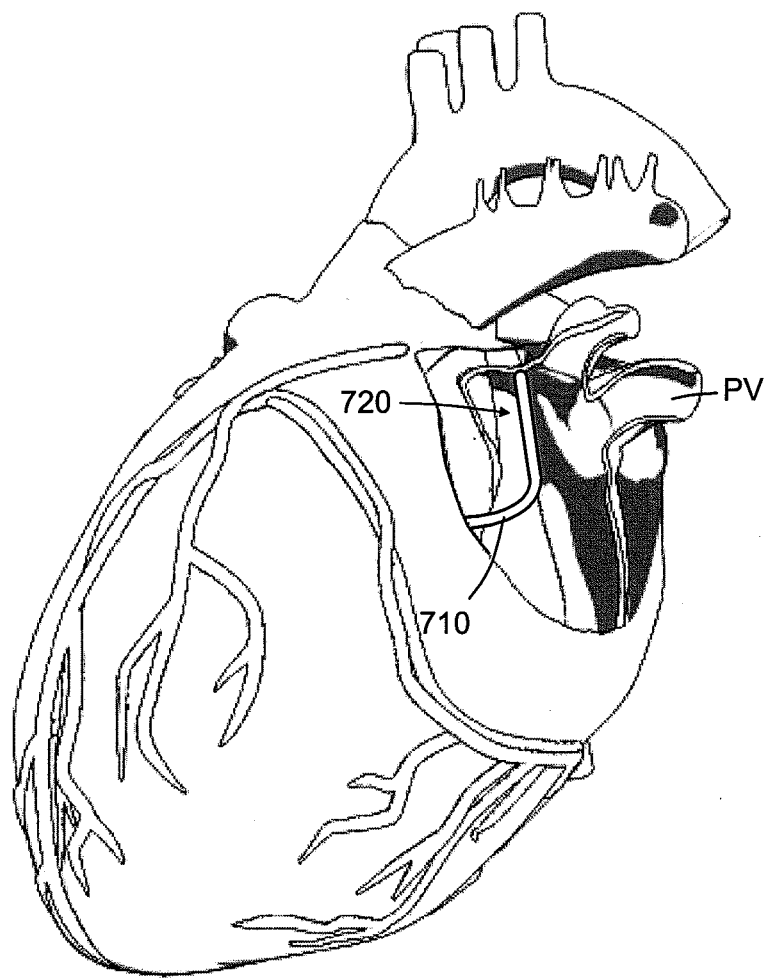
FIG. 29 is a cut-away schematic view of a heart and deflectable working end of another ablation probe configured for ablating a linear lesion to treat atrial fibrillation.
Figure 30:
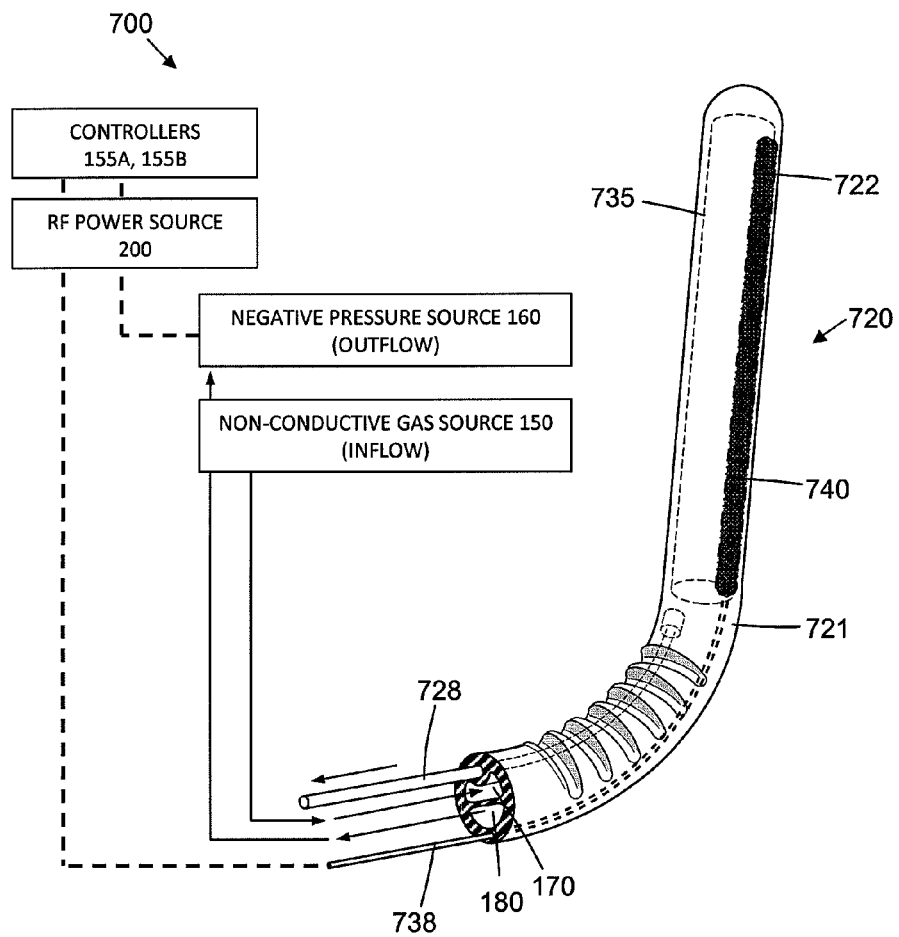
FIG. 30 is a schematic perspective view of the deflectable working end of FIG. 29 illustrating an elongate dielectric structure.
Figure 31:
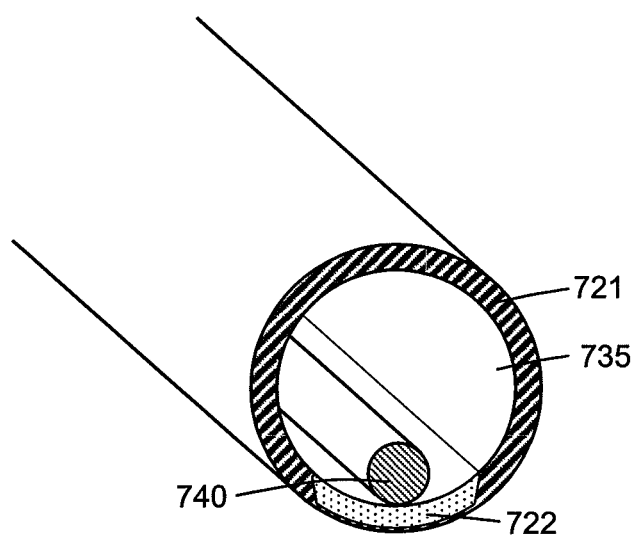
FIG. 31 is a cross-sectional view of the deflectable working end and dielectric structure of FIG. 30 illustrating an interior electrode.

FIGS. 29-31 schematically illustrate another embodiment of electrosurgical system 700 and catheter having working end 710 for treating atrial fibrillation with linear lesions within a heart chamber to block aberrant conduction pathways. Catheter 710 can have a guidewire channel (not shown) and can be navigated to perform an elongated ablation in a heart chamber as in FIG. 20. In this embodiment, the catheter working end 720 has a flexible shaft portion 721 that included an axially-extending thin-wall dielectric 722 in one surface for engaging tissue to provide a linear lesion as depicted in FIG. 31. The catheter shaft 721 is deflectable by means of a pull-wire 728 that can be actuated from a catheter handle. FIG. 30 is another schematic illustration that shows the gas source 150 and gas circulation controller 155A that can provide gas circulation within interior chamber 735 interior of the thin-wall dielectric 722. The RF power source 200 is coupled to a lead 738 and elongated first polarity electrode 740 in the interior chamber 735. The RF power source 200 and controller 155B can be actuated to convert the neutral gas flow to a plasma and contemporaneously ablate tissue engaged by dielectric 722 as described above. The second polarity electrode can be provided on the catheter shaft remote from dielectric 722 or any type of ground pad may be used (not shown). In all other respects, the method of the invention for ablation of cardiac tissue follows the steps described above. The working end can have radiopaque markings, and the system can be operated in accordance with algorithms. It should be appreciated that additional electrodes can be provided in the catheter working end (not shown) for mapping conduction in the heart pre- and post ablation.

Figure 32:
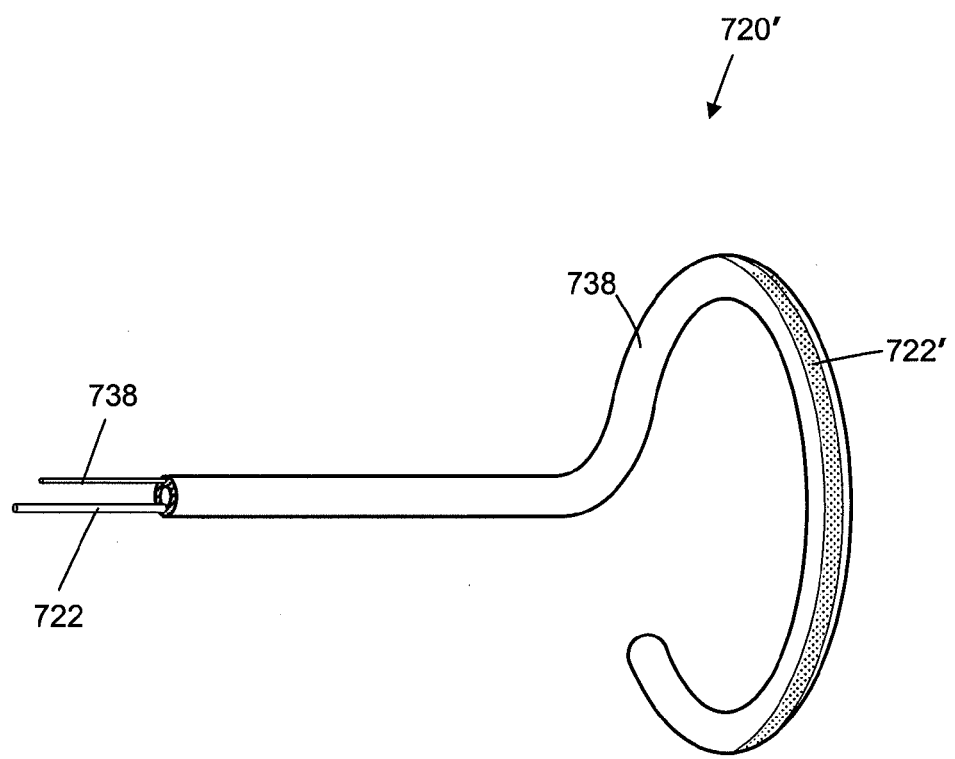
FIG. 32 is a perspective view of another deflectable working end similar to that of FIGS. 30-31 for creating a circumferential lesion to treat atrial fibrillation.

FIG. 32 illustrates another catheter working end 720' that is similar to that of FIGS. 29-31 that is deflectable by a pull-wire 738 to provide all or part of circumferential lesion in a pulmonary vein (see FIGS. 28-29). In this embodiment, the thin-wall dielectric 722' extends around the exterior surface of the articulated working end.

Figure 33:
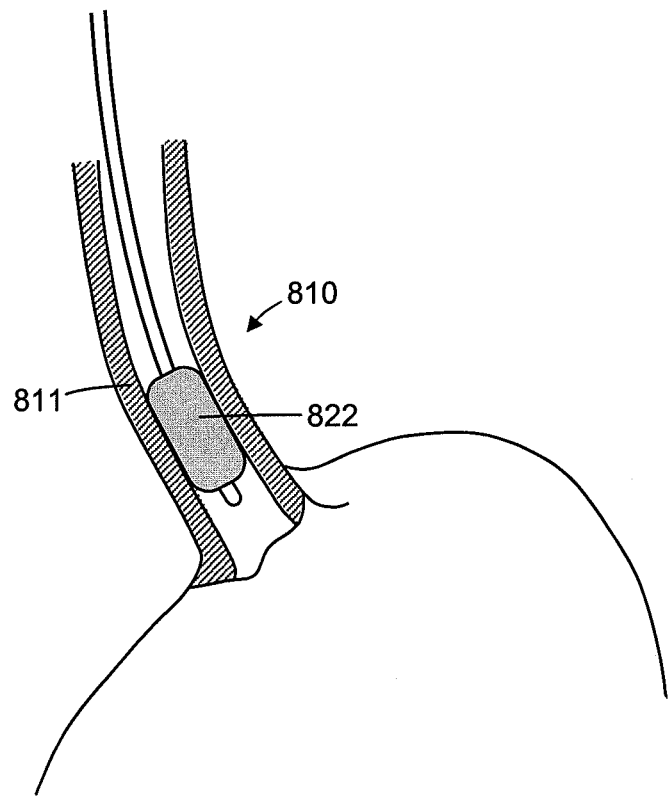
FIG. 33 is a cut-away schematic view of a esophagus and working end of another ablation probe similar to that of FIG. 27 with an expandable thin-wall dielectric structure configured for expansion by an interior skeletal framework.
Figure 34:
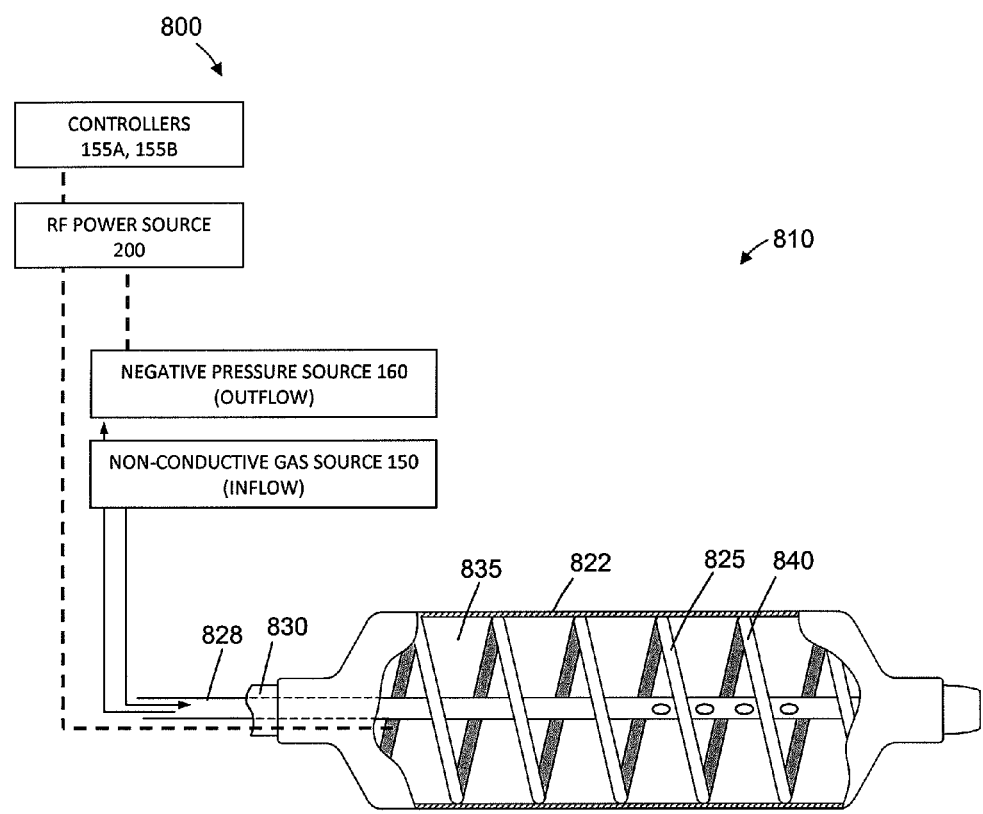
FIG. 34 is a cut-away view of the expandable thin-wall dielectric structure of FIG. 33 showing the interior skeletal support frame that optionally functions as an electrode.

FIGS. 33 and 34 illustrate another embodiment of electrosurgical system 800 that comprises a catheter having working end 810 for treating an esophagus 811, for example to ablate Barrett's esophagus, to apply energy to lower esophageal sphincter or for other disorders. The system operates as previously described in FIGS. 25A-28 in embodiments that have an expandable dielectric structure. In the dielectric structure 822 of FIGS. 33-34, the expansion of the structure is provided by a skeletal support member such as an interior spring-like member, with an optional pull-cable actuation mechanism. As can be seen in FIG. 34, a helical support member 825 is provided that is capable of a contracted cross-section (axially-stretched) or an expanded cross-section in chamber 835 which is assisted by pulling central cable 828 in catheter shaft 830. In this embodiment, the dielectric can again comprise a thin-wall silicone as described above. In this embodiment, it has been found that the support member 825 can be of a conductive metal and coupled to RF power source to function as a first polarity electrode 840. The second polarity electrode (not shown) can be located elsewhere on the catheter is a location in contact with tissue, or a ground pad can be used.

Figure 35:
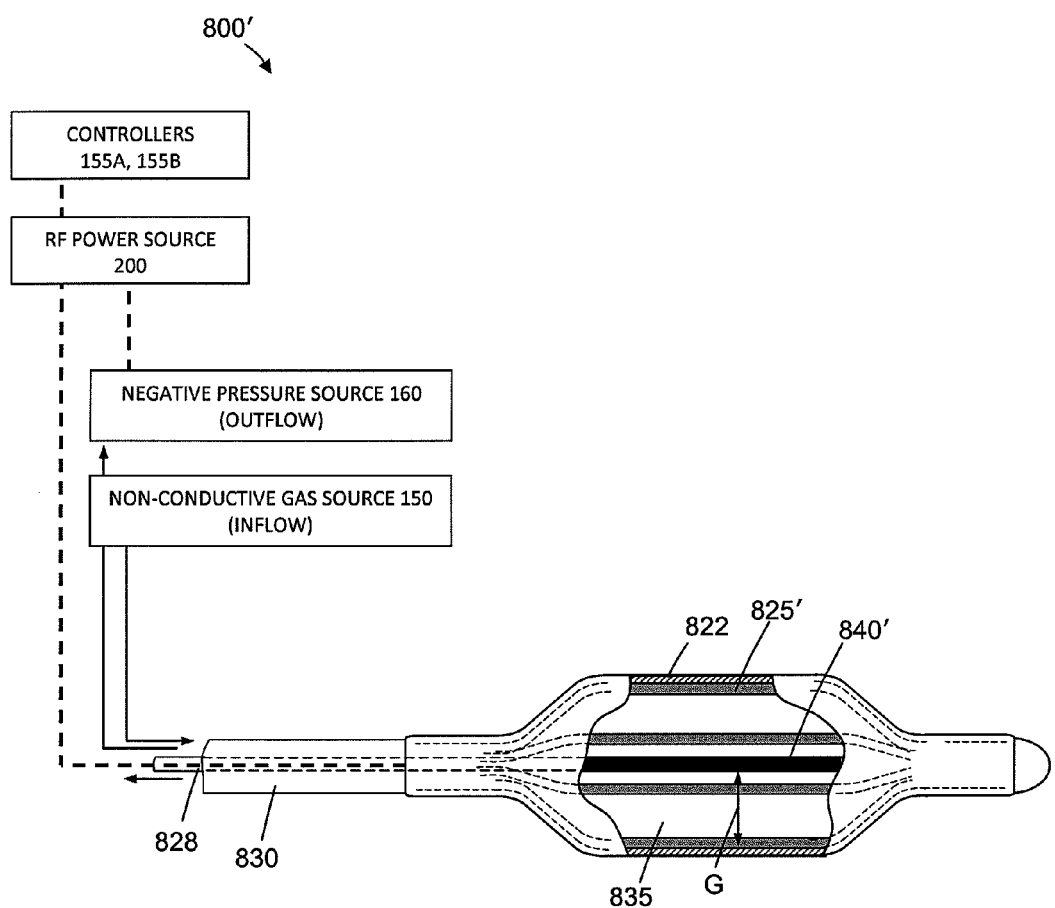
FIG. 35 is a cut-away view of another expandable dielectric structure similar to FIG. 34 showing an alternative interior skeletal support frame.

FIG. 35 illustrates another embodiment of electrosurgical system 800' that is similar to that of FIG. 34 with a dielectric structure 822 that is supported in an expanded condition by a plurality of bowed-out skeletal support members 825' that are assisted by pull-cable 828. In this embodiment, the portion of the pull-cable within chamber 835 functions as a first polarity electrode 840'. In operation in any of the embodiments above, it has been found that the first polarity electrode can provide sufficient voltage to create a substantially uniform plasma in an interior chamber (see FIGS. 2, 8, 11A, 28, 30, 33, 35) of a non-expandable or expandable dielectric when the surface of the electrode is less than 15 mm, less than 10 mm or less than 5 mm from the interior wall of the dielectric. This maximum dimension from the dielectric wall to the electrode 840' is indicated at gap G in FIG. 35. In has also been found that, in operation, the first polarity electrode can provide voltage to create a substantially uniform plasma in an interior chamber of a non-expandable or expandable dielectric wall when the electrode contacts the surface of the dielectric 822 as in FIG. 34, but the electrode surface should engage less than about 10% of the interior surface of the dielectric wall. If the first polarity electrode engages greater than about 10% of the interior surface of the dielectric wall, then the "flux" of energy delivery through tissue as schematically depicted in FIG. 8 will be reduced, a greater capacitive coupling may occur about the regions of the electrode(s) in contact with the wall which can reduce the uniformity of tissue ablation.

Figure 36:
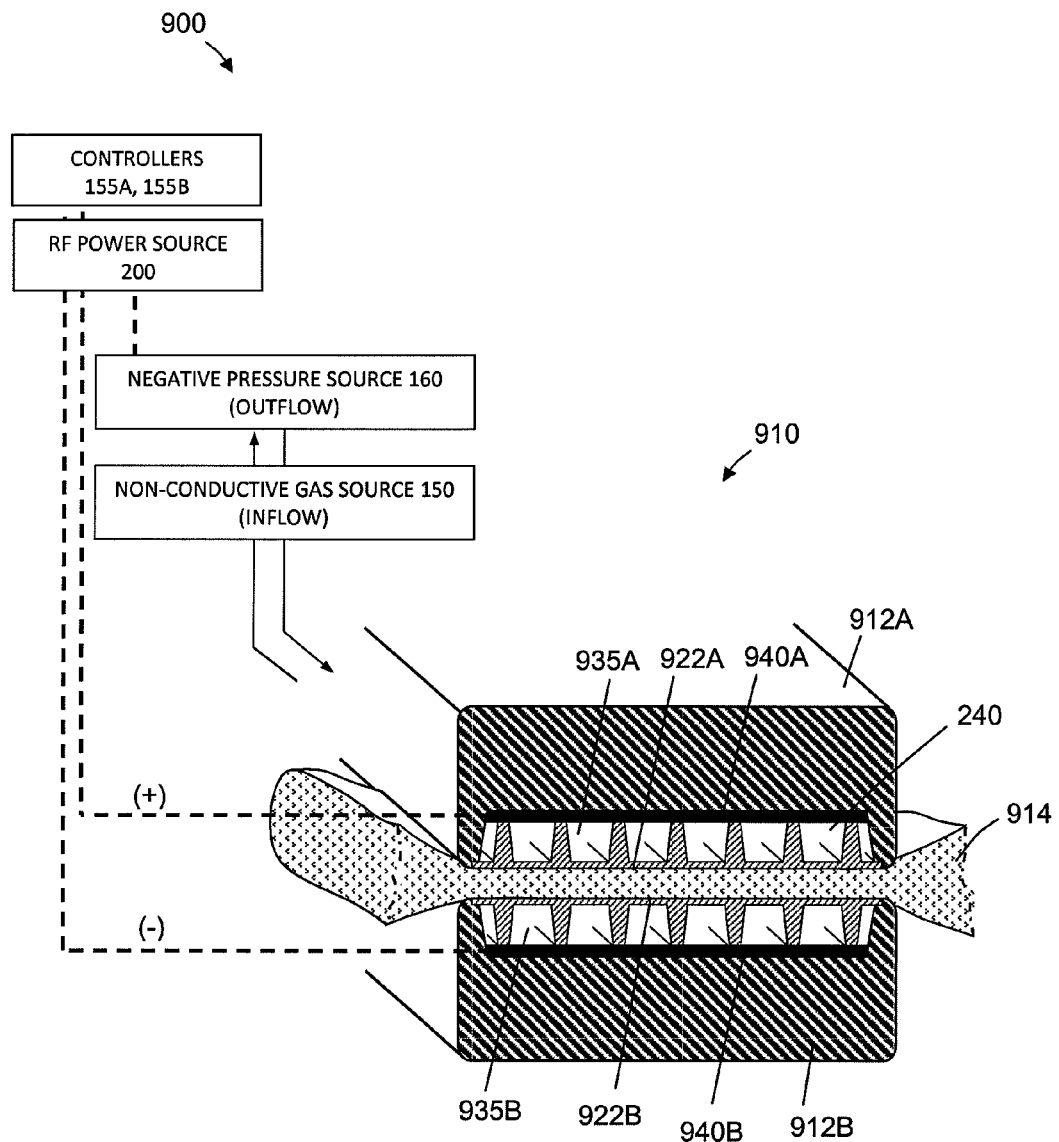
FIG. 36 is a sectional schematic view of a working end of another ablation probe comprising first and second opposing jaws engaging tissue with each jaw engagement surface including a thin-wall dielectric structure, the jaws configured for sealing or coagulating tissue clamped therebetween.

FIG. 36 illustrates another embodiment of electrosurgical system 900 wherein the working end 910 comprises first and second opposable jaws 912A and 912B that are adapted for clamping tissue for coagulation, sealing or welding tissue 914. In one embodiment, both jaws have a tissue-engaging surface that comprises a dielectric structure 922A, 922B that is similar in function to all other such dielectric structures described above. FIG. 36 is a schematic illustration that again shows gas source 150 and gas circulation controller 155A that can deliver gas to chambers 935A, 935B in the jaws. The RF power source 200 and controller 155B can be actuated to convert the neutral gas flows in the chambers 935A, 935B into plasma 240 and contemporaneously to apply energy to engaged tissue 914. In this embodiment, the jaws carry first and second polarity electrodes 945A and 945B, respectively, to thus make jaw function by means of a contained ionized gas and capacitive coupling, which differs from previous embodiments. It should be appreciated that one jaw can comprise a single electrode surface, as opposed to the plasma-initiated capacitive coupling system of FIG. 36. The dielectric structures of FIG. 36 are of the type described in FIGS. 4B and 5A wherein the thin-wall dielectric material is supported by support columns, posts, channels of the like.

Figure 37:
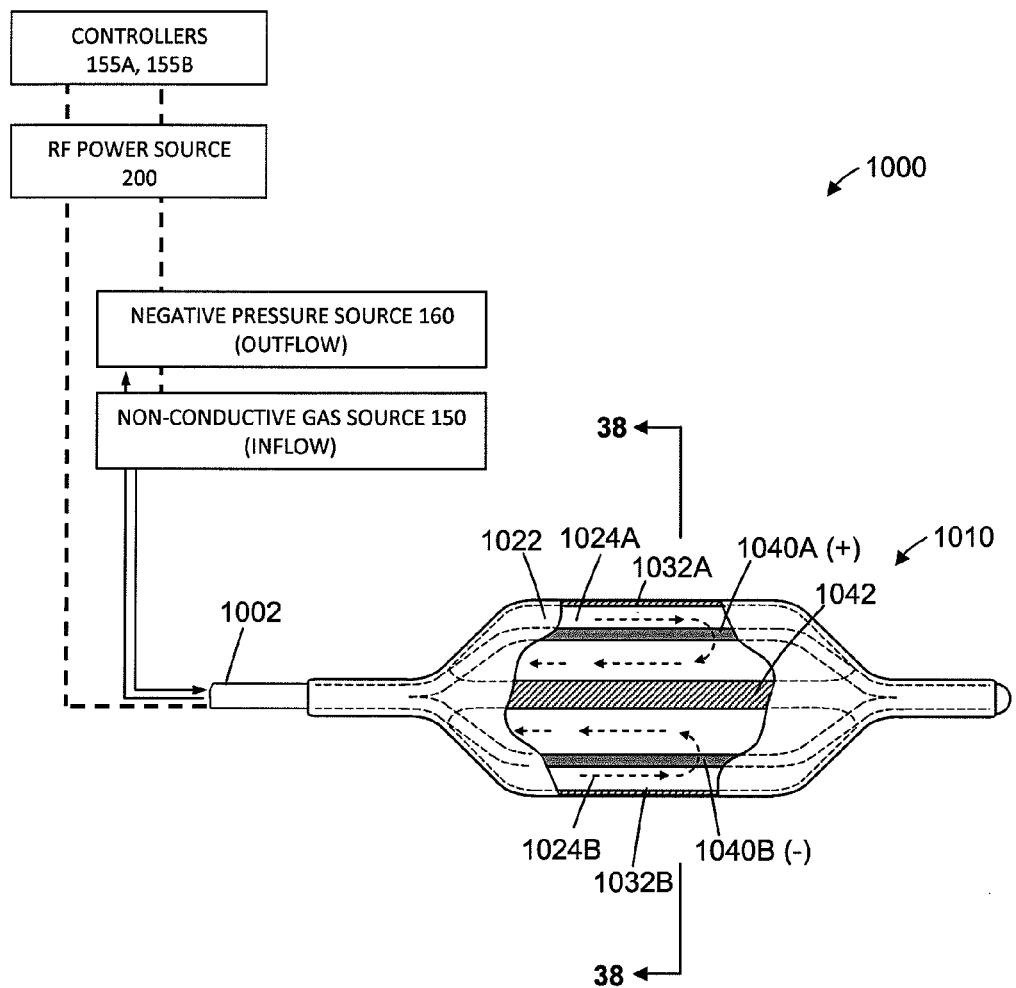
FIG. 37 is a schematic view of the working end of another embodiment with an expandable thin dielectric walled structure with a plurality of plasma-carrying chambers for performing another form of bi-polar ablation.
Figure 38:
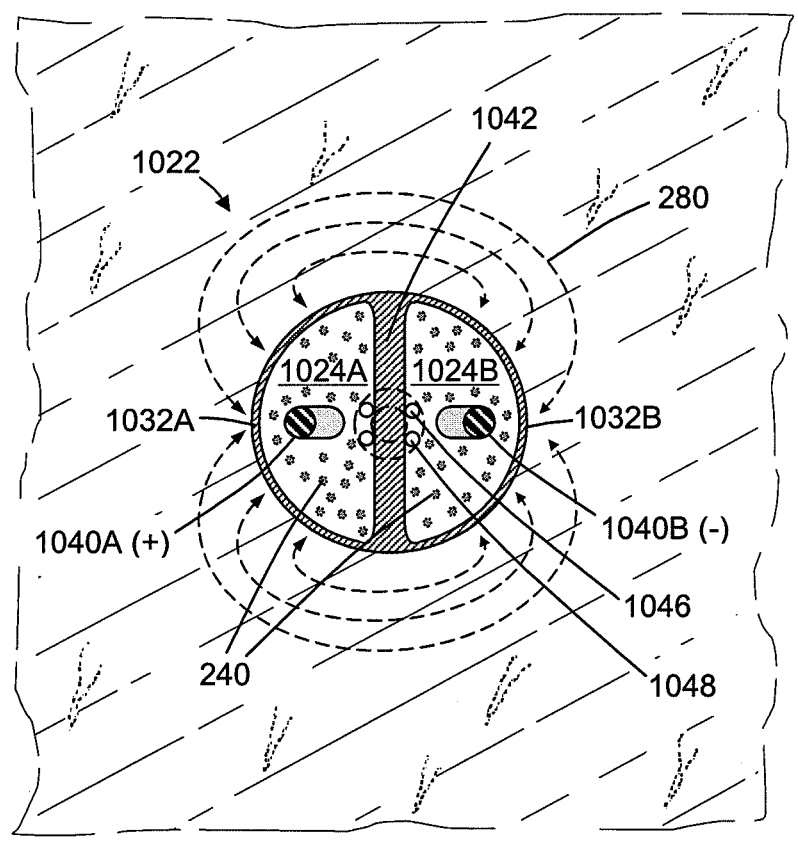
FIG. 38 is a transverse sectional schematic view of the working end of FIG. 30 taken along line 38-38 of FIG. 37 rotated 90° showing the current flow in tissue.

FIGS. 37 and 38 illustrate another embodiment of electrosurgical system 1000 again includes a catheter or probe shaft 1002 extending to a working end 1010 that carries an expandable dielectric structure 1022. In this embodiment, the dielectric structure 1022 includes a plurality of interior chambers, for example first and second chambers 1024A and 1024B. The expansion of the dielectric structure 1022 can be provided by skeletal support members such as interior spring-like members as described above or by expansion by fluid pressure of gas inflows or a combination thereof. Each chamber is configured to carry a flexible interior electrode, with adjacent chambers having opposing polarity interior electrodes, such as electrodes 1040A and 1040B indicated at (+) and (−) polarities in FIGS. 37 and 38, to allow another form a bi-polar ablation. In this embodiment, the electrodes and support members can comprise the same members. As can be seen in FIG. 37, the external wall of dielectric structure 1022 has thin wall portions 1032A and 1032B for capacitively coupling energy to tissue, and a thicker wall portion 1042 that insulates and separates the first and second chambers 1024A and 1024B. The flexible electrodes 1040A and 1040B are operatively coupled to RF power source 200. The gas inflow source 150 and negative pressure source 160 are coupled to in inflow and outflow channels communicating with each interior chamber, 1024A and 1024B, independently. In the transverse sectional view of FIG. 31, the open terminations 1046 and 1048 of the inflow and outflow channels can be seen in each interior chamber, 1024A and 1024B. Thus, each chamber is provided with a circulating gas flow (indicated by arrows in FIG. 37) similar to that described in previous embodiments with respect to single chamber working ends.

FIG. 38 is a schematic sectional view of the dielectric structure 1022 deployed in a targeted tissue 1050. It can be understood that the system can be actuated to circulate gas in chambers 1024A and 1024B which then is converted to a plasma 240 in each chamber as described previously. In this embodiment and method of use, the capacitive coupling occurs through the thin dielectric walls 1032A and 1032B in paths of current flow indicated at 280 in FIG. 38. Whereas the previous embodiments illustrated a single chamber containing a plasma that capacitively coupled current to a non-gas electrode, the embodiment of FIGS. 37 and 38 depicts the use of at least two contained plasma electrodes and capacitive coupling therebetween. It should be appreciated that the number of adjacent chambers carrying opposing polarity electrodes can be utilized in a thin-wall dielectric structure, for example 2 to 10 or more, with the chambers having any suitable dimensions or orientations relative to one another.

In another aspect of the invention, depicted schematically in FIGS. 39-41B, the electrosurgical system and working end 1200 and methods include generating and controlling the plasma filaments or streamers 1210 as depicted in FIGS. 8 to 9C. Such plasma streamers discharge electrical potential and can be described functionally as a dielectric barrier discharge. Such plasma streamers are generated through a dielectric barrier that couples RF current from an electrode to the dielectric and allowing for momentary lines of electrostatic flux in a thin-wall dielectric to deliver current across the dielectric to tissue. As used herein, the term dielectric barrier discharge describes a specific type of high-voltage, alternating current, gaseous discharge that can be created in an atmospheric or near-atmospheric pressure range. This near-atmospheric pressure gas can be provided in an enclosed space with a circulating gas flow as described in embodiments above.

Figure 39:
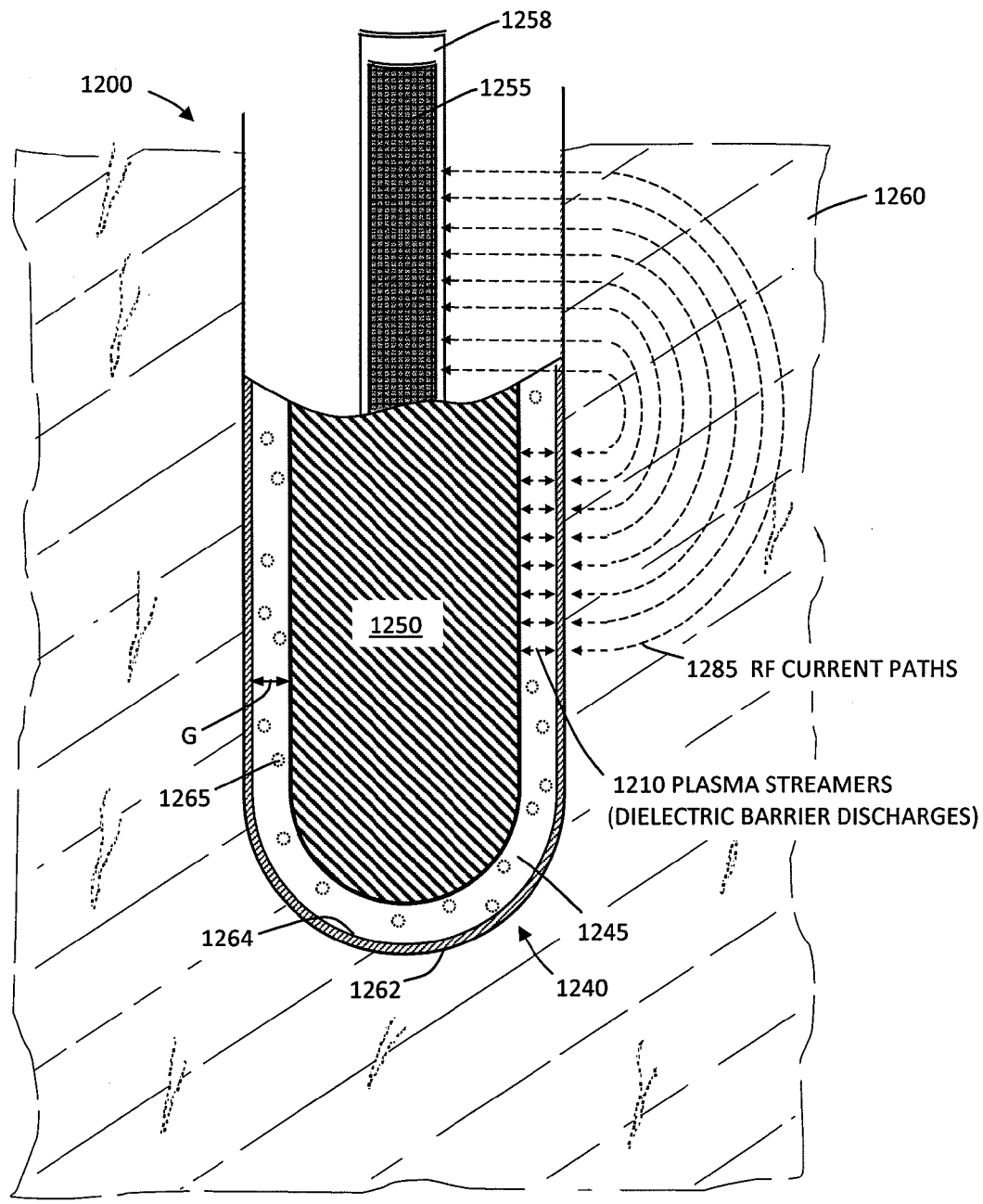
FIG. 39 is a cut-away view of an alternative working end with a thin-wall dielectric construct enclosing an interior chamber.

FIG. 39 schematically illustrates one embodiment of electrosurgical working end 1200 with a dielectric structure 1240 comprising a thin-wall structure or construct 1244 enclosing an interior chamber 1245. The thin-wall construct 1244 is a dielectric such as silicone or an other material as described above with a support frame (see FIG. 34) or other supports (see FIG. 4A) that are not shown for convenience. The thin-wall construct also can comprise a rigid material such as a glass or ceramic. A first polarity electrode 1250 is within interior chamber 1245 and a second polarity electrode 1255 is exterior of the chamber 1245 and in one embodiment is mounted on a portion of the dielectric wall 1244. The second polarity electrode 1255 can be mounted on a thin insulative substrate 1258 so that electrode 1255 is not in direct contact with the dielectric wall 1244. The interior chamber 1245 again is configured for gas flows therethrough during operation as described in previous embodiments.

FIG. 39 depicts a first surface 1262 of the dielectric wall 1244 or dielectric barrier that contacts tissue 1260. The second surface 1264 of the dielectric wall interfaces with the neutral gas 1265 in the interior chamber 1245. FIG. 39 further depicts discharges in the form of plasma filaments or plasma streamers 1210 that occur between the surface of electrode 1250 and the second surface 1264 of the dielectric wall 1244.

Figure 40A:
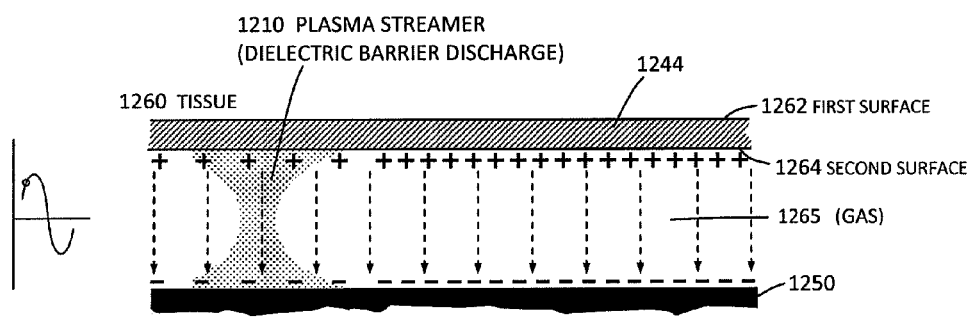
FIGS. 40A-40B are schematic views of the dielectric surface of FIG. 29 showing the charge distribution on low charge mobility surfaces that permits dielectric barrier discharges to form a substantially stable pattern.
Figure 40B:
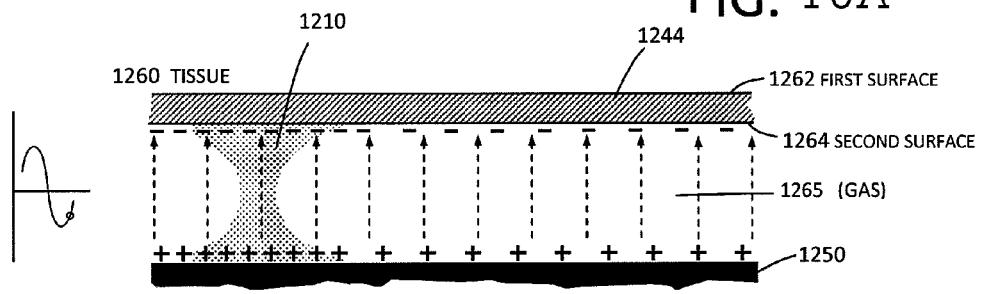

FIGS. 40A and 40B are enlarged schematic views of a portion of the dielectric wall 1244 of FIG. 32 that illustrate how the plasma streamers 1210 can be generated to limit or control the spatiotemporal chaos of such streamers. The low charge mobility of the dielectric wall 1244 makes it impossible for charges generated in the gas 1265 to immediately cross the dielectric to conduct to the electrode 1255 positioned at the exterior of the interior chamber 1245 (see FIG. 29). Referring to FIGS. 40A-40B, with each half-cycle of the driving oscillation, the voltage applied across the gas can exceed that required for breakdown thus resulting in the formation of narrow discharges or plasma streamers 1210 that initiate the conduction of electrons toward the more positive electrode. As charge accumulates on the dielectric layer at the end of each plasma streamer PS, the voltage drop across the plasma streamer diminishes and falls below a discharge-sustaining level and the discharge is thus extinguished. The low charge mobility on the dielectric 1244 results in the self-arresting aspect of such plasma streamers and also limits the lateral region over which the gap voltage is diminished. At certain selected voltages, a discharge deposits charges on the dielectric surfaces, which sets up an electric field that opposes the applied field resulting in an abruptly lowered field in a localized region of the dielectric wall 1244 (see FIGS. 40A-40B). When voltage is reversed, the field is reinforced by the charge deposited during the preceding half-cycle—which can result in the next discharge to occur in the location of a previous streamer resulting in spatial control of such plasma streamers 1210. This aspect of dielectric barrier discharges in the form of such plasma streamers permits neighboring, somewhat parallel, plasma streamers to be created. Further, the plasma streamers form in close proximity to one another and can form a substantially stable spatiotemporal pattern. It should be appreciated that the electrode 1250 can be parallel or non-parallel relative to the dielectric wall 1244 and such plasma streamer patterns and spacing can be substantially stable when coupling energy to a tissue volume having uniform electrical parameters.

Figure 41A:
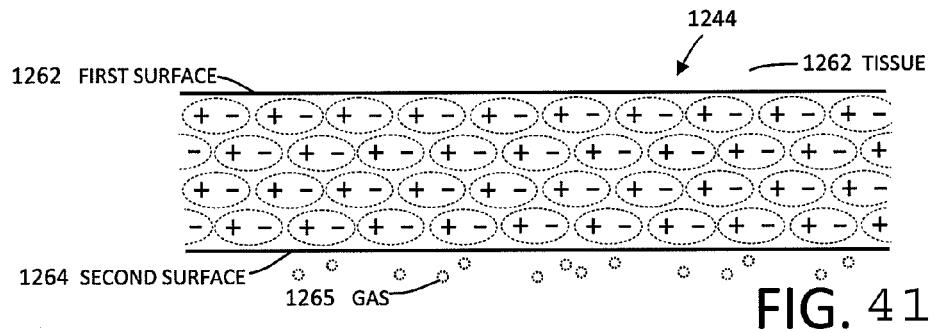
FIGS. 41A-41E are enlarged schematic views of the dielectric surface of FIGS. 40A-40B illustrating the method of creating momentary lines of electrostatic flux to controllably couple RF energy to tissue.
Figure 41B:
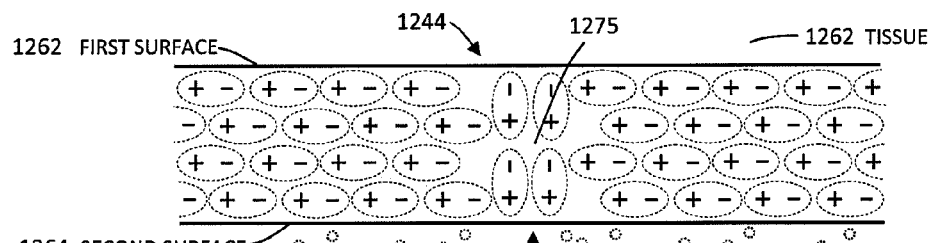
Figure 41C:
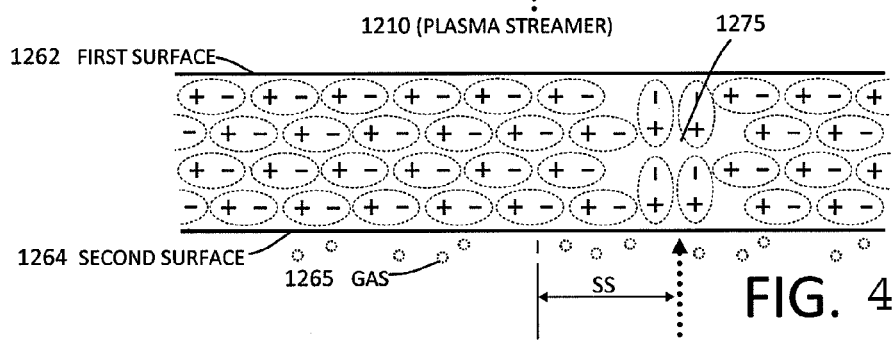
Figure 41D:
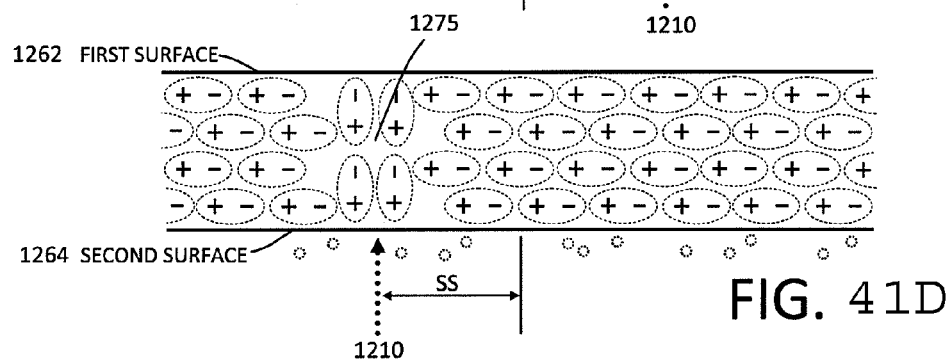
Figure 41E:
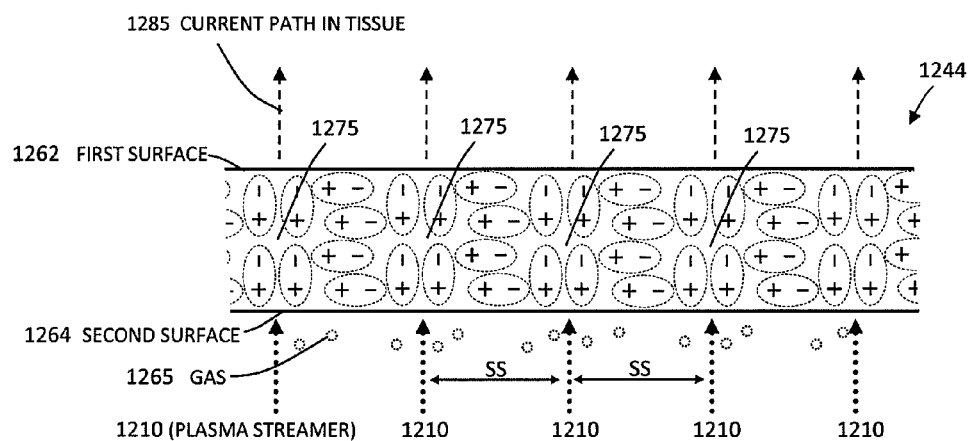

In another aspect of the invention relating to the energy-delivery surface of FIGS. 40A-40B, the arrangement of electrode 1250, enclosed gas volume 1265 and dielectric wall 1244 allows dielectric-barrier discharges to be utilized to thereby create and momentarily concentrate electrostatic lines of flux in the thin-wall dielectric to allow RF current to cross the dielectric to the tissue. FIGS. 41A-41E are further enlarged schematic views of the wall dielectric 1244 at different stages of interaction with a pattern of plasma streamers 1210 that are spaced apart by streamer spacing SS (FIG. 41E). FIG. 41A shows the dielectric wall 1244 at rest. FIGS. 41B-41D depict an initial interval that may range from nanoseconds to milliseconds or more after initiation of energy delivery in which the applied voltage causes chaotic plasma streamers 1210 to form. After an initial energy delivery interval, the plasma streamers can settle into a substantially stable pattern with streamer spacing SS as depicted in FIG. 41E. In order for the discharges to occur, the local regions of the dielectric structure are subjected to momentary concentrations of electrostatic lines of flux 1275 or electron permeability as depicted in FIGS. 41B-41E. The RF current thus is capable of coupling across the concentrations of electrostatic lines of flux 1275 in the dielectric wall 1244.

At some applied voltages, there is complete spatiotemporal chaos among the dielectric barrier discharges. By experimentation, it has been found that control of several system parameters can reduce the spatiotemporal disorder or chaos of the discharges, and control of certain parameters can substantially eliminate such spatiotemporal chaos and create spatially repetitive locations of plasma streamers 1210 and repetitive spacing between streamers when applying energy to tissue. Chart A below lists the several system parameters and ranges thereof that enable the energy delivery methods of the invention.

CHART A

| | Actual | Min-Max |
|---|---|---|
| Dielectric constant (Relative static permittivity) | 3.0-3.5 | 1-10,000 |
| Gap (G) between interior chamber electrode and inner surface of dielectric wall | 0-0.5 mm | 0-5 mm |
| Surface area of dielectric (Energy-delivery surface) | 5-17.5 cm$^2$ | 0.1-30 cm$^2$ |
| Dielectric wall thickness | 0.005"-0.010" | 0.001"-0.020" |
| Gas flow (replacement volume/time) | 0.5-1 slpm | 0.1-2 slpm |
| Frequency of alternating current | 480 kHz | 100 kHz-20 MHz |
| Gas pressure | 760 Torr | 10 Torr-1000 Torr |
| Field strength | 0.3 MV/m-8 MV/m | 50,000 V/m-1600 MV/m |

In one aspect of the invention, a method of applying energy to tissue comprises contacting tissue with an energy-delivery surface and creating substantially stable patterns of plasma streamers adjacent a dielectric barrier that couple RF current to, and across, the energy-delivery surface to the engaged tissue. The pattern of plasma streamers is created in a gas-filled chamber that is at least partly bounded by the dielectric energy-delivery surface.

In another aspect of the invention, a method of reducing or substantially eliminating spatiotemporal chaos of plasma streamers comprises providing and controlling a plurality of system parameters listed in Chart A, consisting of (i) controlling the dielectric constant of the dielectric wall, (ii) controlling the "gap" or spacing G between electrode 1250 in plasma reaction chamber 1245 and dielectric wall 1244 (FIG. 39), (iii) controlling the surface area of dielectric wall in tissue contact, (iv) controlling the thickness of the dielectric wall, (v) controlling the circulation of neutral gas through the interior chamber, (vii) controlling the frequency of the current, (viii) controlling the pressure in the interior chamber, and (ix) controlling the field strength which relates to voltage and spacing between electrode 1250 and dielectric wall 1244.

Figure 42:
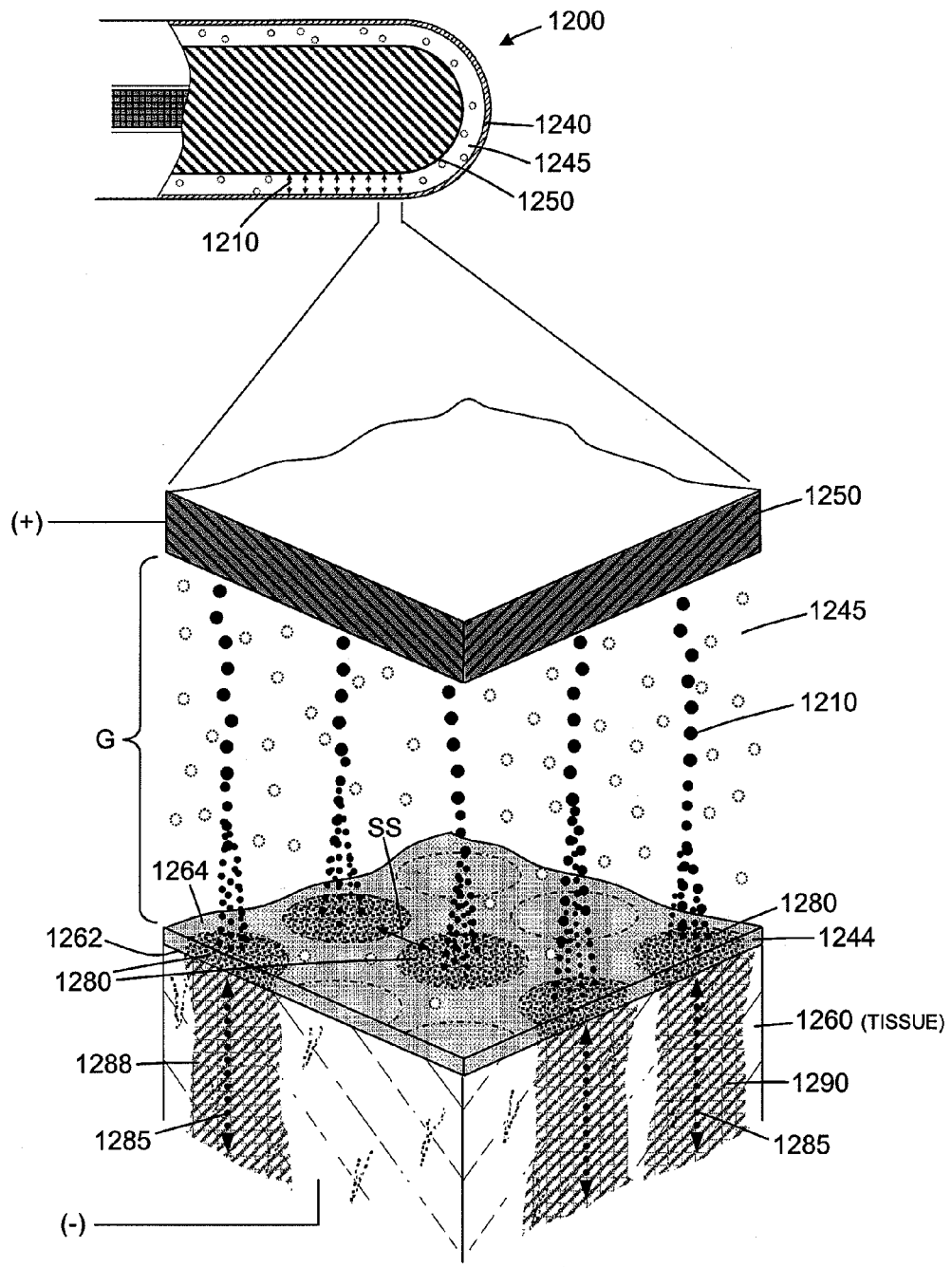
FIG. 42 is a greatly enlarged cut-away schematic view of a portion of a working end of FIG. 39 illustrating spatiotemporal switching of transitory plasma streamers and further illustrating the method of Joule heating of tissue.

FIG. 42 illustrates an enlarged schematic view of working end 1200 of FIG. 39 wherein the energy-delivery structure or construct 1240 comprises a thin dielectric wall 1244 enclosing interior chamber 1245 and electrode 1250 in which plasma streamers 1210 can be created to apply energy to tissue 1260 in the manner as schematically depicted previously in FIGS. 41A-41E. In the greatly enlarged view of FIG. 42, it can be seen that a first energy-delivery surface 1262 of dielectric wall 1244 contacts tissue 1260 and transitory plasma streamers 1210 cross the space between the surface of electrode 1250 to a second (inner) surface 1264 of the dielectric wall 1244. FIG. 42 illustrates schematically that a number of plasma streamers 1210 over a time interval are spaced apart by spacing SS if the electrical parameters of tissue 1260 remain substantially uniform during a treatment interval. FIG. 42 also shows schematically that discrete local regions or focal points 1280 of the dielectric wall 1244 are briefly modified as the plasma streamers 1210 and current paths 1285 in the tissue cause the electron-permeability of such focal points 1280 of wall 1244. The system and method thus cause spatiotemporal switching of the focal points 1280 of energy application about the dielectric surface by coupling energy to said points with transitory plasma streamers 1210, which are self-arresting so that the high temperature, high-intensity plasma does not measurably damage or degrade the dielectric wall.

In the embodiment schematically depicted in FIG. 42, the tissue regions 1288 that are indicated with hatching represent regions that are affected by Joule heating about the current paths 1285. This Joule heating of tissue is similar to that depicted in FIGS. 9A-9D above. In one working end embodiment 1200 as depicted in FIG. 42, it has been found that controlling the parameters in Chart A above can provide plasma streamers 1210 and current paths 1285 that cause transitory electron-permeability in the dielectric wall 1244 and which limit heating of focal points 1280 of the dielectric wall 1244. The embodiment of FIG. 42 schematically illustrates a system that optimizes and maximizes Joule heating of the engaged tissue. In this embodiment, at least the dielectric constant of wall 1244, the wall thickness, gap dimension G, gas flow and electric field strength in the plasma streamers are selected within ranges to provide an electrical impedance across the gap G that is less than the impedance of the contacted tissue 1260, or less than twice the impedance of the contacted tissue or less than three times the impedance of the contacted tissue 1260. In a system embodiment having such characteristics, the effects in tissue will be substantially caused by Joule heating of tissue—and not conductive heating from the surface of the dielectric wall 1244. In other words, greater Joule heating, and lesser conductive heating, will be provided when the impedance across the plasma in gap G is less than the impedance across the tissue 1260. In general, a lower impedance plasma can be provided by lower gap G dimensions, high dielectric constants of the dielectric wall and high field strengths.

Figure 43:
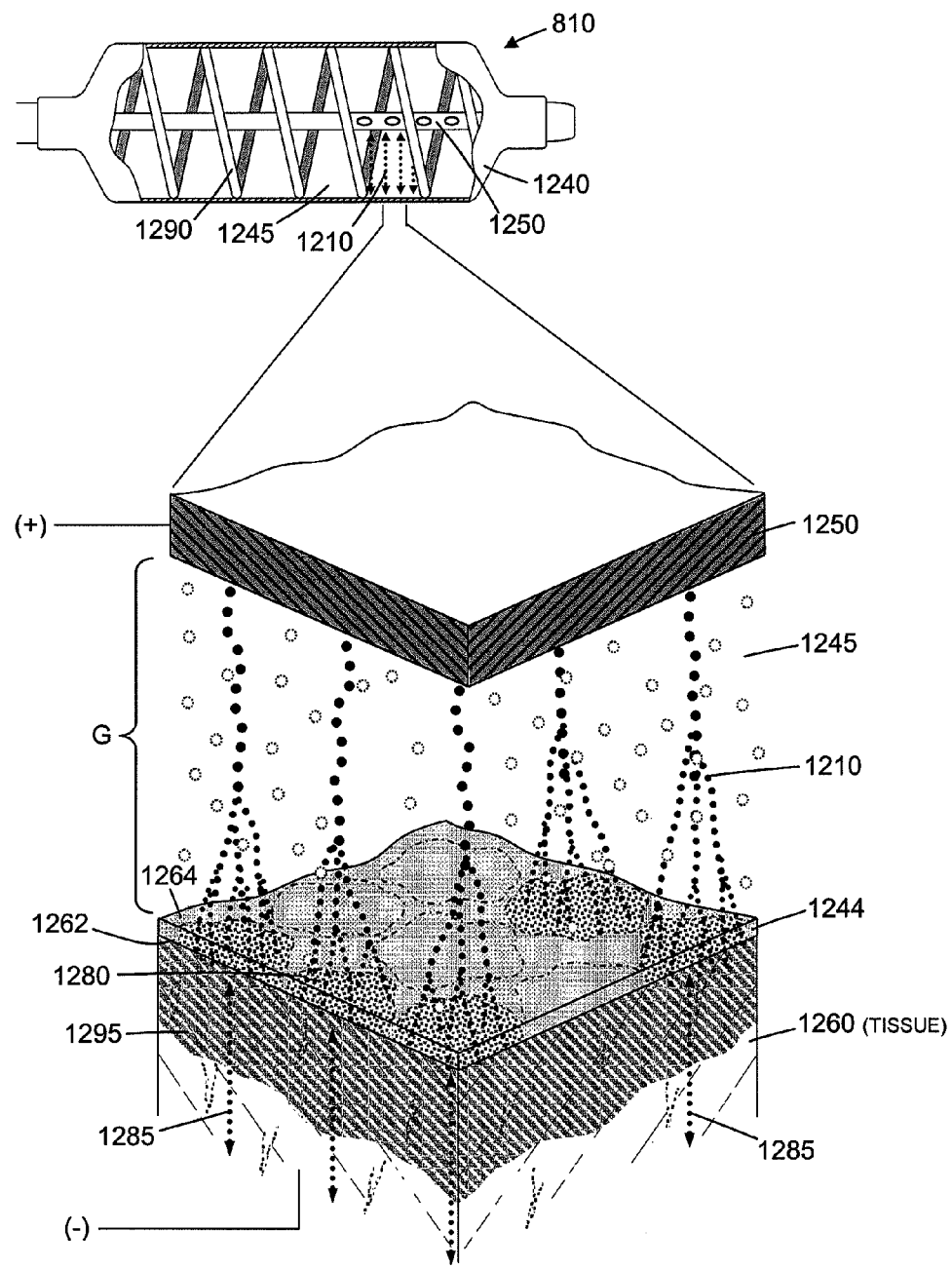
FIG. 43 is a greatly enlarged cut-away view of a portion of a working end FIG. 34 illustrating spatiotemporal switching of plasma streamers and further illustrating the method of heating the wall to thereafter conduct heat to tissue.

FIG. 43 illustrates an enlarged schematic view of the working end 810 of FIG. 34 wherein the energy-delivery construct 1240 comprises a thin-wall, distensible dielectric material 1244 supported by frame 1290. The interior chamber 1245 is configured with a central electrode member 1250 and neutral gas flows are provided through the central electrode member 1250 as described above in the text accompanying FIG. 34. In the embodiment of FIG. 43, the plasma streamers 1210 again are formed between the electrode 1250 and second surface 1264 of dielectric wall 1244 in the same general manner as in the embodiment of FIG. 42. In one system embodiment, referring to FIG. 43, it has been found that the parameters in Chart A can be adjusted within the indicated ranges to provide plasma streamers 1210 that maximize heating of the focal points 1280 while at the same minimizing Joule heating of tissue along the current paths 1285 in tissue 1260. The embodiment of FIG. 43 thus uses the dielectric wall 1244 as a heat applicator in which the heated focal points 1280 passively conduct heat to tissue adjacent each focal point, which indicated as conductively heated region 1295 of the tissue. In this aspect of the invention, it has been found that a high plasma resistance, compared to the tissue resistance, can result in streamers 1210 coupling energy to the focal points 1280 of the wall 1244 without coupling as much energy through the electron-permeable regions to cause Joule heating of the tissue. In this aspect of the invention, utilizing a dielectric wall 1244 with a lower dielectric constant will provide for greater passive tissue heating from the heated material of focal points 1280 and lesser Joule heating along current paths 1285 in tissue. Further, a system embodiment that has a greater dimension gap G, in general, will be conducive to greater passive tissue heating from the heated dielectric wall 1244 lesser Joule heating in adjacent tissue. In one embodiment configured for conductive heating of tissue from a heated energy-delivery surface can have a dielectric wall 1244 with an electrical permittivity ranging from about 1 to 20, a gap G ranging from about 1 mm to 10 mm, and other parameters within the ranges indicated in Chart A.

Another aspect of the invention can be seen schematically in comparing FIGS. 42 and 43, wherein the plasma streamers 1210 have somewhat different characteristics when the discharge is across a lower resistance plasma (and higher dielectric constant wall 1244) rather than a higher resistance plasma. In a lower resistance plasma, the plasma streamers 1210 are focused with fewer branching filaments at the interface (second surface) 1264 of the dielectric wall 1244, as indicated schematically in FIG. 42. In a higher resistance plasma, the plasma streamers 1210 are more branched and irregular and interface with the second surface 1264 of the dielectric wall 1244 more broadly, as indicated schematically in FIG. 43. Experimentation has shown that higher resistance plasmas as depicted in FIG. 43 are suited for heating the dielectric wall to create a heat applicator surface for passive heating of adjacent tissue. In the embodiment of FIG. 43, the focal points 1280 that are heated by the plasma streamers are believed to larger in a high resistance plasma, while such streamers 1210 still remain spaced apart in repetitive locations as described above. In one embodiment configured for maximizing Joule heating of tissue, the dielectric wall 1244 has an electrical permittivity ranging from about 20 to 10,000, a gap G that is less than about 5 mm, and other parameters within the ranges indicated in Chart A.

In another aspect of the invention, the plasma streamers 1210 can be created with a duty cycle in which voltage is applied to initiate the plasma in on/off intervals wherein each "on" interval is at least long enough to create a discharge across gap G which can be greater than 1 millisecond, 100 milliseconds or 500 milliseconds. In such a duty cycle, the "off" intervals can be at least 1 millisecond, 100 milliseconds or 500 milliseconds. In one system embodiment, the duty cycle can configured to cooperate with the thermal relaxation time of dielectric material of the thin-wall enclosure that interfaces with the plasma streamers. For example, referring to FIG. 43, if the plasma streamers 1210 heat the focal points to about 200° C. in a voltage "on" interval, and the dielectric material relaxes in temperature back to 50° C. in 0.25 seconds, then the duty cycle can have "off" intervals of approximately 0.25 seconds to insure that the dielectric wall does not overheat which can extend the life of the dielectric structure.

In general, referring to FIGS. 39-43, the system of the invention for applying energy to tissue comprises a probe having an energy-delivery surface configured for spatiotemporal switching of focal points of energy application 1280 about the surface in contact with tissue, a gas-filled chamber 1245 interior of the energy-delivery surface and a voltage source configured for creating transitory plasma streamers 1210 in the gas to thereby provide spatial and temporal switching of energy coupling to the focal points. FIG. 44 illustrates the steps of a method of the invention comprising contacting tissue with a thin-wall energy-delivery construct, and causing spatiotemporal switching of focal points of energy application about the construct by coupling energy to said focal points with transitory plasma streamers, which thereby distributes energy application over the area of the contacted tissue to cause uniform tissue ablation. The energy-delivery surface comprises a thin wall dielectric material. The system includes a first electrode 1250 within the interior chamber 1245 and coupled to the voltage source. Further, the system includes a second electrode carried on the shaft of the probe or proximate to, but electrically insulated from, the energy-delivery surface 1262. As described above, the system also includes a gas source configured for providing a flow of a neutral gas through the interior chamber 1245.

In another aspect of the invention, a method comprises causing the spatiotemporal switching of plasma streamers between first and second electrodes positioned respectively at an interior and exterior of dielectric wall 1244 and a surface 1262 in contact with tissue. Further, the temporal aspect of the switching step occurs within less than milliseconds. Also, the spatial aspect of the switching step moves the focal points 1280 apart from one another a minimum distance. The method of energy delivery can be utilized in an interstitial application or the energy-delivery surface can be deployed in a body lumen, space or cavity.

Figure 45:
FIG. 45 is a block diagram of another method corresponding to the invention.
Figure 46:
FIG. 46 is a block diagram of another method corresponding to the invention.

Another aspect of a method of the invention is shown in FIG. 45 which comprises contacting tissue with a wall 1244 having an energy-delivery surface 1262, coupling energy through the wall by providing electron-permeable focal points 1280 wherein the transitory plasma streamers 1210 and current paths 1285 in tissue result in Joule heating of tissue about the current paths 1285. Another method invention is shown in FIG. 46 which comprises contacting tissue with a wall 1244 having energy-delivery surface 1262 and coupling energy to focal points 1280 within the surface by transitory plasma streamers 1210 thereby heating the focal points 1280 and thereafter causing conductive heating of tissue adjacent the focal points.

In another aspect of the invention, as can be understood from FIGS. 42-43, the material of wall 1244, the thickness of the wall 1244, its dielectric constant, the gap G and other parameters can be selected to provide a desired ratio of passive conductive heating of tissue versus Joule-heating of tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of applying energy to tissue comprising:
   contacting tissue with a thin-wall energy-delivery construct; and
   causing spatiotemporal switching of focal points of energy application about the construct by coupling energy to said focal points with transitory plasma streamers.

2. The method of claim 1 wherein the energy-delivery construct has a first surface interfacing with tissue and a second surface interfacing with the plasma streamers.

3. The method of claim 1 wherein the applied energy includes Joule heating of tissue from current coupled through the construct by the plasma streamers.

4. The method of claim 1 wherein the applied energy includes conductive heating of tissue adjacent the first surface.

5. The method of claim 1 wherein the switching step includes altering the electron-permeability of said construct.

6. The method of claim 2 wherein the switching step includes applying sufficient voltage across a gas to create the plasma streamers.

7. The method of claim 5 wherein the switching step includes providing first and second electrodes positioned respectively at an exterior and interior of the construct and applying voltage between the electrodes to create the plasma streamers.

8. The method of claim 1 wherein the temporal aspect of the switching step occurs within less than milliseconds.

9. The method of claim 1 wherein the spatial aspect of the switching step moves the focal points apart from one.

10. The method of claim 1 wherein the spatial aspect of the switching step moves the focal points to substantially cover the energy-delivery construct in contact with tissue.

11. The method of claim 1 wherein the energy-delivery construct comprises a dielectric.

12. The method of claim 1 wherein contacting step includes deploying the energy-delivery construct interstitially.

13. The method of claim 1 wherein contacting step includes deploying the energy-delivery construct in a body lumen, space or cavity.

14. The method of claim 1 wherein contacting step included expanding an energy-delivery construct from a compacted configuration to an expanded configuration.

15. A method of applying energy to tissue comprising:
contacting tissue with a thin dielectric wall; and
causing spatiotemporal switching of focal points of energy application about the wall by coupling energy to said focal points with transitory plasma streamers;
wherein the focal points apply energy to tissue by Joule heating.

16. A method of applying energy to tissue comprising:
contacting tissue with a thin dielectric wall; and
causing spatiotemporal switching of focal points of energy application about the wall by coupling energy to said focal points with transitory plasma streamers;
wherein the focal points apply energy to tissue by conductive heating.

17. A method of applying electrosurgical energy to tissue comprising:
engaging tissue with first surface of a dielectric barrier; and
coupling RF current to a second surface of the dielectric barrier through a plasma, wherein dielectric material momentarily concentrates electrostatic lines of flux allowing RF current across the dielectric barrier to the tissue.

18. The method of claim 17, wherein coupling RF current to the second surface is accomplished by plasma filaments.

19. The method of claim 18, wherein the plasma filaments extend from at least one electrode to the second surface.

20. The method of claim 19, wherein the plasma filaments are within a gas in an interior chamber surrounded at least in part by the dielectric barrier.

21. The method of claim 17, further comprising utilizing a controller to limit spatiotemporal chaos of the plasma filaments.

22. The method of claim 17, further comprising utilizing a controller to spatiotemporally control the plasma filaments.

23. The method of claim 17, further comprising utilizing a controller to create a spatiotemporally pattern of plasma filaments.

24. The method of claim 23, wherein controlling the plasma filaments further spatiotemporally controls the electrostatic lines of flux.

25. The method of claim 23, wherein the controller controls RF voltage.

26. The method of claim 23, wherein the controller controls a flow of gas in which the plasma filaments occur.

* * * * *